(12) United States Patent
Crowe et al.

(10) Patent No.: US 11,667,719 B2
(45) Date of Patent: Jun. 6, 2023

(54) VHH IMMUNOGLOBULIN CHAIN VARIABLE DOMAIN THAT BINDS TO IL-7R AND METHODS OF USE THEREOF FOR TREATING AUTOIMMUNE AND/OR INFLAMMATORY DISEASES

(71) Applicant: SORRISO PHARMACEUTICALS, INC., San Diego, CA (US)

(72) Inventors: Scott Crowe, Cambridge (GB); Mike West, Cambridge (GB); Kevin Roberts, Cambridge (GB); Tim Carlton, Cambridge (GB); Luana Maggiore, Cambridge (GB); Marion Cubitt, Cambridge (GB); Lurdes Duarte, Cambridge (GB); Martyn Symmons, Cambridge (GB); Keith Ray, Cambridge (GB)

(73) Assignee: SORRISO PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 17/752,710

(22) Filed: May 24, 2022

(65) Prior Publication Data

US 2022/0363769 A1 Nov. 17, 2022

Related U.S. Application Data

(63) Continuation of application No. 17/620,030, filed as application No. PCT/GB2020/051496 on Jun. 19, 2020.

(30) Foreign Application Priority Data

Jun. 21, 2019 (EP) .................................. 19181868

(51) Int. Cl.
*C07K 16/28* (2006.01)

(52) U.S. Cl.
CPC ...... *C07K 16/2866* (2013.01); *C07K 2317/22* (2013.01); *C07K 2317/24* (2013.01); *C07K 2317/33* (2013.01); *C07K 2317/569* (2013.01); *C07K 2317/76* (2013.01); *C07K 2317/92* (2013.01)

(58) Field of Classification Search
CPC ............ C07K 16/2866; C07K 2317/76; C07K 2317/92
See application file for complete search history.

(56) References Cited

U.S. PATENT DOCUMENTS

| | | | |
|---|---|---|---|
| 3,300,077 A | 1/1967 | David et al. | |
| 5,780,028 A | 7/1998 | Graham | |
| 8,399,188 B2 | 3/2013 | Zhao et al. | |
| 9,080,157 B2 | 7/2015 | Convents et al. | |
| 9,527,925 B2 | 12/2016 | Gschwind et al. | |
| 9,932,412 B2 | 4/2018 | Kim et al. | |
| 10,633,438 B2 | 4/2020 | Crowe et al. | |
| 10,772,839 B2 | 9/2020 | Crowe et al. | |
| 10,980,748 B2 | 4/2021 | Crowe et al. | |
| 2004/0041867 A1 | 3/2004 | Lapstun et al. | |
| 2005/0147612 A1 | 7/2005 | Yayon et al. | |
| 2006/0034833 A1 | 2/2006 | Beirnaert | |
| 2006/0034845 A1 | 2/2006 | Silence et al. | |
| 2006/0057197 A1 | 3/2006 | Han et al. | |
| 2006/0138181 A1 | 6/2006 | Thom et al. | |
| 2007/0020267 A1 | 1/2007 | Fuh et al. | |
| 2007/0042399 A1 | 2/2007 | Wright et al. | |
| 2007/0077249 A1 | 4/2007 | Silence et al. | |
| 2007/0178082 A1 | 8/2007 | Silence et al. | |
| 2007/0237769 A1 | 10/2007 | Silence et al. | |
| 2008/0031770 A1 | 2/2008 | Heselton et al. | |
| 2008/0039761 A1 | 2/2008 | Heaton et al. | |
| 2008/0122965 A1 | 5/2008 | Fang | |
| 2008/0145420 A1 | 6/2008 | Simon | |
| 2008/0149143 A1 | 6/2008 | Chou et al. | |
| 2008/0260820 A1 | 10/2008 | Borrelly et al. | |
| 2009/0064457 A1 | 3/2009 | Brustle | |
| 2009/0064460 A1 | 3/2009 | Tang et al. | |
| 2010/0077422 A1 | 3/2010 | Bushinsky | |
| 2010/0137213 A1 | 6/2010 | Fernandez et al. | |
| 2010/0239682 A1 | 9/2010 | Andremont et al. | |
| 2010/0260857 A1 | 10/2010 | Fallon et al. | |
| 2011/0028695 A1 | 2/2011 | Revets et al. | |
| 2011/0098518 A1 | 4/2011 | Minoux et al. | |
| 2011/0109365 A1 | 5/2011 | Mai | |
| 2011/0112229 A1 | 5/2011 | Nagaoka et al. | |
| 2011/0229476 A1 | 9/2011 | Liu et al. | |
| 2012/0130872 A1 | 5/2012 | Baughman et al. | |

(Continued)

FOREIGN PATENT DOCUMENTS

| EP | 2275443 A1 | 1/2011 |
|---|---|---|
| EP | 2275443 B1 | 12/2015 |

(Continued)

OTHER PUBLICATIONS

Paul, WE (1993) Fundamental Immunology, 3rd ed. Raven Press, NY, Chap. 9, pp. 292-295.*

(Continued)

*Primary Examiner* — Robert S Landsman

(74) *Attorney, Agent, or Firm* — Wilson Sonsini Goodrich & Rosati

(57) ABSTRACT

There are provided inter alia polypeptides capable of inhibiting IL-7 and/or L-TSLP binding to IL-7R (IL-7R), as well as to constructs and pharmaceutical compositions comprising these polypeptides.

16 Claims, 19 Drawing Sheets

Specification includes a Sequence Listing.

(56) References Cited

U.S. PATENT DOCUMENTS

| | | |
|---|---|---|
| 2012/0151199 A1 | 6/2012 | Shriver |
| 2013/0173687 A1 | 7/2013 | Tuchman et al. |
| 2014/0030049 A1 | 1/2014 | Imai et al. |
| 2014/0044730 A1 | 2/2014 | Yancopoulos et al. |
| 2014/0141152 A1 | 5/2014 | Sostek et al. |
| 2014/0170212 A1 | 6/2014 | Ortenzi et al. |
| 2014/0186365 A1 | 7/2014 | Robinson et al. |
| 2014/0294826 A1 | 10/2014 | Shoemaker |
| 2014/0377287 A1 | 12/2014 | Govindan et al. |
| 2015/0017183 A1 | 1/2015 | Seidah et al. |
| 2015/0058173 A1 | 2/2015 | Schmeling et al. |
| 2015/0147318 A1 | 5/2015 | Bergeron et al. |
| 2015/0176031 A1 | 6/2015 | Streffer |
| 2015/0337035 A1 | 11/2015 | Anderson et al. |
| 2016/0060338 A1 | 3/2016 | Barrett et al. |
| 2016/0156465 A1 | 6/2016 | Vaikuntanathan et al. |
| 2016/0264659 A1 | 9/2016 | Heavner et al. |
| 2017/0002069 A1 | 1/2017 | Crowe et al. |
| 2017/0022271 A1 | 1/2017 | Hoffman et al. |
| 2017/0260266 A1 | 9/2017 | Ahmed et al. |
| 2018/0009881 A1 | 1/2018 | Crowe et al. |
| 2018/0037639 A1 | 2/2018 | Crowe et al. |
| 2018/0100008 A1 | 4/2018 | Crowe et al. |
| 2018/0100009 A1 | 4/2018 | Crowe et al. |
| 2019/0008778 A1 | 1/2019 | Crowe et al. |
| 2019/0040156 A1 | 2/2019 | Demarest et al. |
| 2019/0092855 A1 | 3/2019 | Crowe et al. |
| 2019/0307891 A1 | 10/2019 | Crowe et al. |
| 2020/0079844 A1 | 3/2020 | Beirnaert |
| 2020/0317769 A1 | 10/2020 | Crowe et al. |
| 2021/0198345 A1 | 7/2021 | Crowe et al. |
| 2021/0317195 A1 | 10/2021 | Crowe et al. |
| 2022/0242945 A1 | 8/2022 | Crowe et al. |

FOREIGN PATENT DOCUMENTS

| | | |
|---|---|---|
| EP | 2955196 A1 | 12/2015 |
| WO | WO-9102078 A1 | 2/1991 |
| WO | WO-9201047 A1 | 1/1992 |
| WO | WO-9300077 A1 | 1/1993 |
| WO | WO-9404678 A1 | 3/1994 |
| WO | WO-9425591 A1 | 11/1994 |
| WO | WO-9508562 A1 | 3/1995 |
| WO | WO-9634103 A1 | 10/1996 |
| WO | WO-9923221 A2 | 5/1999 |
| WO | WO-0212502 A2 | 2/2002 |
| WO | WO-0248382 A2 | 6/2002 |
| WO | WO-03035694 A2 | 5/2003 |
| WO | WO-2004009776 A2 | 1/2004 |
| WO | WO-2004037205 A2 | 5/2004 |
| WO | WO-2004041862 A2 | 5/2004 |
| WO | WO-2004041863 A2 | 5/2004 |
| WO | WO-2004041865 A2 | 5/2004 |
| WO | WO-2004041867 A2 | 5/2004 |
| WO | WO-2006122786 A2 | 11/2006 |
| WO | WO-2006122787 A1 | 11/2006 |
| WO | WO-2006138181 A2 | 12/2006 |
| WO | WO-2007005955 A2 | 1/2007 |
| WO | WO-2007025977 A2 | 3/2007 |
| WO | WO-2007027714 A2 | 3/2007 |
| WO | WO-2007048022 A2 | 4/2007 |
| WO | WO-2007070948 A1 | 6/2007 |
| WO | WO-2007104529 A2 | 9/2007 |
| WO | WO-2008020079 A1 | 2/2008 |
| WO | WO-2008031770 A2 | 3/2008 |
| WO | WO-2008039761 A2 | 4/2008 |
| WO | WO-2008049897 A1 | 5/2008 |
| WO | WO-2008101985 A2 | 8/2008 |
| WO | WO-2008101985 A3 | 10/2008 |
| WO | WO-2008122965 A2 | 10/2008 |
| WO | WO-2008124170 A2 | 10/2008 |
| WO | WO-2008144753 A2 | 11/2008 |
| WO | WO-2008124170 A3 | 12/2008 |
| WO | WO-2008149143 A2 | 12/2008 |
| WO | WO-2009021754 A2 | 2/2009 |
| WO | WO-2008149143 A3 | 4/2009 |
| WO | WO-2009046168 A1 | 4/2009 |
| WO | WO-2009064457 A2 | 5/2009 |
| WO | WO-2009064460 A2 | 5/2009 |
| WO | WO-2009068627 A2 | 6/2009 |
| WO | WO-2009147248 A2 | 12/2009 |
| WO | WO-2010020811 A1 | 2/2010 |
| WO | WO-2010045506 A2 | 4/2010 |
| WO | WO-2010056550 A1 | 5/2010 |
| WO | WO-2010045506 A3 | 7/2010 |
| WO | WO-2010077422 A2 | 7/2010 |
| WO | WO-2010085643 A1 | 7/2010 |
| WO | WO-2010115998 A2 | 10/2010 |
| WO | WO-2011009365 A1 | 1/2011 |
| WO | WO-2011083175 A1 | 7/2011 |
| WO | WO-2011094259 A2 | 8/2011 |
| WO | WO-2011098518 A2 | 8/2011 |
| WO | WO-2011104687 A1 | 9/2011 |
| WO | WO-2011112229 A2 | 9/2011 |
| WO | WO-2011135026 A1 | 11/2011 |
| WO | WO-2011135040 A1 | 11/2011 |
| WO | WO-2011139269 A1 | 11/2011 |
| WO | WO-2011139629 A2 | 11/2011 |
| WO | WO-2012007880 A2 | 1/2012 |
| WO | WO-2011139629 A3 | 4/2012 |
| WO | WO-2012055030 A1 | 5/2012 |
| WO | WO-2012078878 A2 | 6/2012 |
| WO | WO-2012130872 A1 | 10/2012 |
| WO | WO-2012131053 A1 | 10/2012 |
| WO | WO-2012151199 A1 | 11/2012 |
| WO | WO-2012175741 A2 | 12/2012 |
| WO | WO-2013024059 A2 | 2/2013 |
| WO | WO-2013056984 A1 | 4/2013 |
| WO | WO-2013058833 A1 | 4/2013 |
| WO | WO-2013064701 A2 | 5/2013 |
| WO | WO-2013087857 A2 | 6/2013 |
| WO | WO-2013087874 A1 | 6/2013 |
| WO | WO-2013091103 A1 | 6/2013 |
| WO | WO-2013173687 A1 | 11/2013 |
| WO | WO-2013184871 A1 | 12/2013 |
| WO | WO-2014030049 A2 | 2/2014 |
| WO | WO-2014058875 A3 | 6/2014 |
| WO | WO-2014141152 A2 | 9/2014 |
| WO | WO-2015009996 A1 | 1/2015 |
| WO | WO-2015058173 A1 | 4/2015 |
| WO | WO-2015065987 A1 | 5/2015 |
| WO | WO-2015100409 A2 | 7/2015 |
| WO | WO-2015144852 A1 | 10/2015 |
| WO | WO-2015176031 A2 | 11/2015 |
| WO | WO-2015189302 A1 | 12/2015 |
| WO | WO-2016065323 A2 | 4/2016 |
| WO | WO-2016103093 A1 | 6/2016 |
| WO | WO-2016156465 A1 | 10/2016 |
| WO | WO-2016156466 A1 | 10/2016 |
| WO | WO-2016162537 A1 | 10/2016 |
| WO | WO-2016202411 A1 | 12/2016 |
| WO | WO-2016202414 A1 | 12/2016 |
| WO | WO-2016202415 A1 | 12/2016 |
| WO | WO-2018104483 A1 | 6/2018 |
| WO | WO-2020254826 A1 | 12/2020 |
| WO | WO-2020254827 A1 | 12/2020 |
| WO | WO-2020254828 A1 | 12/2020 |

OTHER PUBLICATIONS

Rudikoff, S et al. (1982) Proc. Natl. Acad. Sci. USA, 79:1979-1983 (doi: 10.1073/pnas.79.6.1979).*

Colman, PM (1994) Research in Immunology, Elsevier, NY, 145(1):33-36.*

Bendig M. M. (1995) Methods: A Companion to Methods in Enzymology, 8:83-93.*

MacCallum et al. (Oct. 11, 1996) J. Mol. Biol., 262(5):732-745. (doi: 10.1006/jmbi.1996.0548).*

Casset et al (2003) Biochemical and Biophysical Research Communications, 307:198-205. (doi:10.1016/S0006-291X(03)01131-8).*

Chen et al. (1995) EMBO J., 14(12):2784-2794. (doi: 10.1002/j.1460-2075.1995.tb07278.x).*

(56) References Cited

OTHER PUBLICATIONS

Markovic I and Savvides SN (Jul. 2020) Frontiers in Immunology. vol. 11 (Article 1557). 19 pages.*
Lee L-F, et al. (Jul. 31, 2012) PNAS 109(31):12674-12679.*
Barata JT, et al. (Dec. 2019) Nature Immunology. (20):1584-1593.*
Corren J, et al. (Sep. 7, 2017) N Engl J Med. (377(10):936-946.*
2005 Drug Bank Data (https://wwwdrugbank.caldrugs/DB00085) for Pancrelipase.
Arbabi-Ghahroudi et al.: Selection and identification of single domain antibody fragments from camel heavy-chain antibodies. FEBS Letters 414(3):521-526 (1997).
Baumgart et al.: Crohn's disease. Lancet 380(9853):1590-1605 (2012).
Bendig. Humanization of Rodent Monoclonal Antibodies by CDR Grafting. Methods A Companion To Methods In Enzymology 8:83-93 (1995).
Biancheri et al. Differential Cleavage of Anti-Tumor Necrosis Factor-Alpha Agents By Matrix Metalloproteinase (MMP)-10 and MMP-12 In Inflammatory Bowel Disease. ECCO, Abstract, 1 page, Dublin (2011).
Biancheri et al.: Proteolytic cleavage and loss of function of biologic agents that neutralize tumor necrosis factor in the mucosa of patients with inflammatory bowel disease. Gastroenterology 149(6):1564-1574 (2015).
Binz et al.: Designing repeat proteins: well-expressed, soluble and stable proteins from combinatorial libraries of consensus ankyrin repeat proteins. J. Mol. Biology 332(2):489-503 (2003).
Bjerkan et al. Multiple Functions of the New Cytokine-Based Antimicrobial Peptide Thymic Stromal Lymphopoietin (TSLP). Pharmaceuticals (Basel) 9(3):E41 (2016).
Blatter et al. New heterobifunctional protein crosslinking reagent that forms an acid-labile link. Biochemistry 24(6):1517-1524 (1985).
Bruno et al.: Basics and recent advances in peptide and protein drug delivery. Ther Deliv. 4(11):1443-1467 (2013).
Caldas et. Humanization of the anti-CD18 antibody 6.7: an unexpected effect of a framework residue in binding to antigen. Mol Immunol. 39(15):941-952 (2003).
Chen et al. Fusion Protein Linkers: Property, Design and Functionality. Adv Drug Deliv Rev 65:1357-1369 (2013). Available online Sep. 29, 2012.
Chomczynski, et al. Single-step method of RNA isolation by acid guanidinium thiocyanate-phenol-chloroform extraction. Anal Biochem. Apr. 1987;162(1):156-9.
Cianferoni et al. Eosinophilic Esophagitis and Gastroenteritis. Curr Allergy Asthma Rep. 15(9):58 (2015).
Colman et al., Effects of amino acid sequence changes on antibody-antigen interactions, Research in Immunology, 1994; 145(1):33-36.
Colombel et al. Adalimumab for maintenance of clinical response and remission in patients with Crohn's disease: the CHARM trial. Gastroenterology 132:52-65 (2007).
Coppieters et al.: Formatted anti-tumor necrosis factor alpha VHH proteins derived from camelids show superior potency and targeting to inflamed joints in a murine model of collagen-induced arthritis. Arthritis Rheum 54(6):1856-1866 (2006).
Corren et al. Tezepelumab in Adults with Uncontrolled Asthma. N Engl J Med. 377(10):936-946 (2017).
Crawley et al. Soluble IL-7R alpha (sCD127) inhibits IL-7 activity and is increased in HIV infection. J Immunol. 184(9):4679-4687 (2010).
Crowe et al.: Gastrointestinal Stability and Tissue Penetration of V565: a Novel Orally Administered Anti-TNFa VorabodyTM. Poster from 10th Annual Proteins and Antibodies Congress [1] (2017).
Crowe et al.: Gastrointestinal Stability and Tissue Penetration of V565: A Novel Orally Administered Anti-TNFa VorabodyTm. Vhsquared, Poster from PEGS Europe Protein and Antibody Engineering Summit, Lisbon, Portugal [1] (2017).
Crowe et al.: Oral Delivery of a Novel Engineered Anti TNFa Domain Antibody (VorabodyTM) for the Treatment of Intestinal Bowel Disease. PEGS Europe Protein & Antibody Engineering Summit [1] (2017).
Crowe et al.: Preclinical Assessment of a Novel Anti-TNFa VorabodyTM as an Oral Therapy for Crohn's Disease. 18th International Congress of Mucosal Immunology, Washington D.C. [1] (2017).
Crowe et al: Preclinical Development of a Novel, Orally-Administered Anti-Tumour Necrosis Factor Domain Antibody for the Treatment of Inflammatory Bowel Disease. Scientific Reports 8:4941 [1-13] (2018).
Croxford et al. IL-23: one cytokine in control of autoimmunity. Eur J Immunol. 42:2263-2273 (2012).
Danese: New therapies for inflammatory bowel disease: from the bench to the bedside. Gut 61(6):918-932 (2012).
Deschacht et al.: A novel promiscuous class of camelid single-domain antibody contributes to the antigen-binding repertoire. J. Immmunol 184(10):5696-5704 (2010).
Desmet et al. Structural basis of IL-23 antagonism by an Alphabody protein scaffold. Nature Communications 5:5237 (2014).
Desmyter et al.: Neutralization of Human Interleukin 23 by Multivalent Nanobodies Explained by the Structure of Cytokine-Nanobody Complex. Front Immunol. 8:884 (2017).
Dooms. Interleukin-7: Fuel for the autoimmune attack. J Autoimmun. 45:40-48 (2013).
Ebersbach et al.: Affilin-novel binding molecules based on human gamma-B-crystallin, an all beta-sheet protein. J. Molecular Biology 372(1):172-185 (2007).
Eken et al. Interleukin 23 in Crohn's disease. Inflamm Bowel Dis. 20:587-595 (2014).
Ellis et al. Anti-IL-7 receptor α monoclonal antibody (GSK2618960) in healthy subjects—a randomized, double-blind, placebo-controlled study. Br J Clin Pharmacol. 85(2):304-315 (2019).
Fadda et al.: Physiological bicarbonate buffers: stabilisation and use as dissolution media for modified release systems. Int. J. Pharm. 382(1-2):56-60 (2009).
Faisst et al.: Isolation of a fully infectious variant of parvovirus H-1 supplanting the standard strain in human cells. Journal of Virology 69(7):4538-4543 (1995).
Fields et al. Dual-attribute continuous monitoring of cell proliferation/cytotoxicity. Am Biotechnol Lab 11(4):48-50 (1993).
Fornasa et al. Dichotomy of short and long thymic stromal lymphopoietin isoforms in inflammatory disorders of the bowel and skin. J Allergy Clin Immunol. 136(2):413-422 (2015).
Frenken et al. Isolation of antigen specific llama VHH antibody fragments and their high level secretion by *Saccharomyces cerevisiae*. J Biotechnol 78(1):11-21 (2000).
Fry et al. Interleukin-7: from bench to clinic. Blood 99(11):3892-3904 (2002).
Fry et al. The many faces of IL-7: from lymphopoiesis to peripheral T cell maintenance. J Immunol. 174(11):6571-6576 (2005).
Furfaro et al. IL-23 Blockade for Crohn s disease: next generation of anti-cytokine therapy. Expert Rev Clin Immunol. 13:457-467 (2017).
Garbacz et al.: A dynamic system for the simulation of fasting luminal pH-gradients using hydrogen carbonate buffers for dissolution testing of ionisable compounds. Eur J Pharm Sci. 51:224-231 (2014).
Giusti et al. Somatic diversification of S107 from an antiphosphocholineto an anti-DNA autoantibody is due to a single base change in its heavy chain variable region. PNAS USA 84(9):2926-30 (1987).
Goldberg et al.: Engineering a targeted delivery platform using Centyrins. Protein Eng Des Sel. 29(12):563-572 (2016).
Goldberg et al. The unusual suspects—innate lymphoid cells as novel therapeutic targets in IBD. Nat Rev Gastroenterol Hepatol (5):271-283 (2015).
Gomes et al., Comparison of yeasts as hosts for recombinant protein production. Microorganisms 6(2):38 [1-23] (2018).
Goyanes et al.: Gastrointestinal release behaviour of modified-release drug products: dynamic dissolution testing of mesalazine formulations. Int. J. Pharm. 484(1-2):103-108 (2015).
Grabulovski et al. A novel, non-immunogenic Fyn SH3-derived binding protein with tumor vascular targeting properties. J Biol Chem. 282(5):3196-3204 (2007).

(56) References Cited

OTHER PUBLICATIONS

Griffiths et al.: Shark Variable New Antigen Receptor (VNAR) Single Domain Antibody Fragments: Stability and Diagnostic Applications. Antibodies 2(1):66-81 (2013).
Grundstrom et al.: Oligonucleotide-directed mutagenesis by microscale 'shot-gun' gene synthesis. Nucleic Acids Research 13(9):3305-3316 (1985).
Guerra et al.: Management of inflammatory bowel disease in poor responders to infliximab. Clin Exp Gastroenterol 7:359-367 (2014).
Hafler et al. Risk alleles for multiple sclerosis identified by a genomewide study. N Engl J Med. 357(9):851-862 (2007).
Hamers-Casterman et al. Naturally occurring antibodies devoid of light chains. Nature 363(6428):446-8 (1993).
Hanauer et al. Human anti-tumor necrosis factor monoclonal antibody (adalimumab) in Crohn's disease: the CLASSIC-I trial. Gastroenterology 130:323-333 (2006).
Hanauer et al., Maintenance infliximab for Crohn's disease: the ACCENT I randomized trial. Lancet 359:1541-1549 (2002).
Harmsen et al.: Effect of a pmr 1 disruption and different signal sequences on the intracellular processing and secretion of Cyamopsis tetragonoloba alpha-galactosidase by *Saccharomyces cerevisiae*. Gene 125(2):115-123 (1993).
Harmsen et al. Properties, production, and applications of camelid single-domain antibody fragments. Appl. Microbiol. Biotechnol. 77:13-22 (2007).
Harmsen et al.: Selection and Optimization of Proteolytically Stable Llama Single-Domain Antibody Fragments for Oral Immunotherapy. Applied Microbiology and Biotechnology 72(3):544-551 (2006).
Hashimoto et al.: Effects of signal sequences on the secretion of hen lysozyme by yeast: construction of four secretion cassette vectors. Protein Engineering 11(2):75-77 (1998).
Hendrickson et al.: Clinical aspects and pathophysiology of inflammatory bowel disease. Clinical Microbiology Reviews 15(1):79-94 (2002).
Henikoff et al. Amino acid substitution matrices from protein blocks. PNAS USA 89(22):10915-10919 (1992).
Heninger et al. IL-7 abrogates suppressive activity of human CD4+CD25+FOXP3+ regulatory T cells and allows expansion of alloreactive and autoreactive T cells. J Immunol. 189(12):5649-5658 (2012).
Hoefman et al.: Pre-Clinical Intravenous Serum Pharmacokinetics of Albumin Binding and Non-Half-Life Extended Nanobodies(R). Antibodies 4(3):141-156 (2015).
Hoogenboom et al. Multi-subunit proteins on the surface of filamentous phage: methodologies for displaying antibody (Fab) heavy and light chains. Nucleic Acids Res. 19(15):4133-4137 (1991).
Horwitz et al.: Secretion of functional antibody and Fab fragment from yeast cells. Proc. Natl. Acad. Sci. U.S.A. 85(22):8678-8682 (1988).
Hu et al., A phylogenomic approach to reconstructing the diversification of serine proteases in fungi. J Evol Biol. 17(6):1204-1214 (2004).
Humphreys et al.: Modes of L929 cell death induced by TNF-alpha and other cytotoxic agents. Cytokine 11(10):773-782 (1999).
Huse et al. Generation of a large combinatorial library of the immunoglobulin repertoire in phage lambda. Science 246(4935):1275-1281 (1989).
Hussack et al.: A V(L) single-domain antibody library shows a high-propensity to yield non-aggregating binders. Protein Eng Des Sel. 25(6):313-318 (2012).
Hussack et al. Chapter 14: Isolation and characterization of Clostridium difficile toxin-specific single-domain antibodies. Methods Mol Biol. 911:211-239 (2012).
Hussack et al. Engineered Single-Domain Antibodies with High Protease Resistance and Thermal Stability. PLoS One. 6(11):e28218 (2011).
Hussack et al.: Neutralization of Clostridium difficile toxin A with single-domain antibodies targeting the cell receptor binding domain. J. Biol. Chem. 286(11):8961-8976 (2011).
Hussack et al.: Protease-resistant single-domain antibodies inhibit Campylobacter jejuni motility. Protein Eng Des Sel. 27(6):191-198 (2014).
Hussack et al.: Single-domain Antibody Inhibitors of Clostridium difficile Toxins. Thesis submitted to the Faculty of Graduate and Postdoctoral Studies, Dept. of Biochemistry, Microbiology and Immunology [1-227] (2011).
Hussack: Single-domain Antibody Inhibitors of Clostridium difficule Toxins. Universite d'Ottawa website [1-3] https://ruor.uottawa.ca/handle/10393/20362 (2013).
Hussan et al. A review on recent advances of enteric coating. IOSR J Pharm 2(6):5-11 (2012).
Johnson et al.: Sensitive affimer and antibody based impedimetric label-free assays for c-reactive protein. Analytical Chemistry 84(15):6553-6560 (2012).
Jones et al.: Targeted localized use of therapeutic antibodies: a review of non-systemic, topical and oral applications. Crit Rev Biotechnol 36(3):506-520 (2015).
Kabat et al. Sequences of proteins of immunological interest. NIH Publ. No. 91-3242 1:647-669 (1991).
Kamm et al.: Practical application of anti-TNF therapy for luminal Crohn's disease. Inflammatory Bowel Diseases. 17(11):2366-2391 (2011).
Karlin, et al. Applications and statistics for multiple high-scoring segments in molecular sequences. PNAS USA 90:5873-5877 (1993).
Khantasup et al. Design and Generation of Humanized Single-chain Fv Derived from Mouse Hybridoma for Potential Targeting Application. Monoclon Antib Immunodiagn Immunother. 34(6):404-17 (2015).
Kim et al. A Dual Target-directed Agent against Interleukin-6 Receptor and Tumor Necrosis Factor α ameliorates experimental arthritis. Scientific Reports 6:20150 (2015).
Kim et al.: Antibody light chain variable domains and their biophysically improved versions for human immunotherapy. Mabs. 6(1):219-235 (2014).
Knezevic et al. Quantitation of affinity, avidity, and binding kinetics of protein analytes with a dynamically switchable biosurface. J Am Chem Soc 134(37):15225-15228 (2012).
Kohler et al. Continuous cultures of fused cells secreting antibody of predefined specificity. Nature 256(5517):495-497 (1975).
Koide et al. Monobodies: antibody mimics based on the scaffold of the fibronectin type III domain. Methods in Molecular Biology 352:95-111 (2007).
Krehenbrink et al.: Artificial binding proteins (Affitins) as probes for conformational changes in secretin PuID. J Mol Biol. 383(5):1058-1068 (2008).
Ling et al.: Approaches to DNA Mutagenesis: An Overview. Analytical Biochemistry 254(2):157-178 (1997).
Lipovsek: Adnectins: engineered target-binding protein therapeutics. Protein Engineering, Design & Selection 24(1-2):3-9 (2011).
Liu et al. Crucial role of interleukin-7 in T helper type 17 survival and expansion in autoimmune disease. Nat Med. 16(2):191-197 (2010) (retraction in: Nat Med. 2013 19(12):1673).
Liu et al.: Targeting TNF-alpha with a tetravalent mini-antibody TNF-TeAb. Biochemical Journal 406(2):237-246 (2007).
Liu. Thymic stromal lymphopoietin: master switch for allergic inflammation. J Exp Med 203(2):269-273 (2006).
Lopes et al.: Mechanism of high-copy-number integration of pMIRY-type vectors into the ribosomal DNA of *Saccharomyces cerevisiae*. Gene. 105(1):83-90 (1991).
Mccoy et al.: Neutralisation of HIV-1 cell-cell spread by human and llama antibodies. Retrovirology 11:83 doi:10.1186/s12977-014-0083-y [1-15] (2014).
Mcgovern et al. The IL23 axis plays a key role in the pathogenesis of IBD. Gut 56:1333-1336 (2007).
Merchant et al.: Predicting the gastrointestinal behaviour of modified-release products: utility of a novel dynamic dissolution test apparatus involving the use of bicarbonate buffers. Int. J. Pharm. 475(1-2):585-591 (2014).
Merchlinksy et al.: Construction of an infectious molecular clone of the autonomous parvovirus minute virus of mice. Journal of Virology 47(1):227-232 (1983).

(56) References Cited

OTHER PUBLICATIONS

Michael. The role of digestive enzymes in orally induced immune tolerance. Immunol Invest. 18(9-10):1049-1054 (1989) (Abstract).
Miethe et al.: Production of Single Chain Fragment Variable (scFv) Antibodies in *Escherichia coli* Using the LEX TM Bioreactor. Journal of Biotechnology 163(2):105-111 (2012).
Molhoj et al. CD19-/CD3-bispecific antibody of the BiTE class is far superior to tandem diabody with respect to redirected tumor cell lysis. Mol Immunol. 44(8):1935-43 (2007).
Muszewska et al., Fungal lifestyle reflected in serine protease repertoire. Sci Rep. 7(1):9147 [1-12] (2017).
Muyldermans. Nanobodies: natural single-domain antibodies. Annu Rev Biochem 82:775-797 (2013).
Muyldermans et al. Sequence and structure of VH domain from naturally occurring camel heavy chain immunoglobulins lacking light chains. Protein Engineering 7(9):1129-1133 (1994).
Nambiar, et al. Total synthesis and cloning of a gene coding for the ribonuclease S protein. Science 223(4642):1299-301 (1984).
Nelson et al.: Nonoclonal antibodies. Molecular Pathology 53(3):111-117 (2000).
Nguyen et al. Functional heavy-chain antibodies in Camelidae. Adv Immunol 79:261-296 (2001).
Nixon et al. Engineered protein inhibitors of proteases. Curr Opin Drug Discov Devel. 9(2):261-268 (2006).
Nogi et al.: Nucleotide sequence of the transcriptional initiation region of the yeast GAL7 gene. Nucleic Acid Research 11(24):8555-8568 (1983).
Noti et al. Thymic stromal lymphopoietin-elicited basophil responses promote eosinophilic esophagitis. Nat Med. 19(8):1005-1013 (2013).
Nurbhai et al.: Measured and Modelled Data Suggest That Oral Administration of V565, A Novel Domain Antibody to TNF-alpha, Could Be Beneficial in the Treatment of IBD. 13th Congress of ECCO, Vienna, Austria, 1 page (2018).
Nurbhai et al.: Oral Anti-Tumour Necrosis Factor Domain Antibody V565 Provides High Intestinal Concentrations, and Reduces Markers of Inflammation in Ulcerative Colitis Patients. Sci Rep. 9(1):14042 (2019).
Nygren. Alternative binding proteins: affibody binding proteins developed from a small three-helix bundle scaffold. FEBS J. 275(11):2668-2676 (2008).
Ordas et al.: Anti-TNF monoclonal antibodies in inflammatory bowel disease: pharmacokinetics-based dosing paradigms. Clin Pharmacol Ther. 91(4):635-646 (2012).
Ortonne. Recent developments in the understanding of the pathogenesis of psoriasis. British Journal of Dermatology 140(Suppl 54):1-7 (1999).
Padlan. Anatomy of the Antibody Molecule. Mol Immunol 31(3):169-217 (1994).
Patnaik et al. Penicillin fermentation: mechanisms and models for industrial-scale bioreactors. Crit Rev Biotechnol 20:1-15 (2015).
Paul. Fundamental Immunology. 3rd Edition, pp. 292-295, Raven Press (1993).
PCT/EP2016/057021 International Search Report and Written Opinion dated Aug. 8, 2016.
PCT/EP2016/057022 International Search Report and Written Opinion dated Jun. 14, 2016.
PCT/EP2016/057024 International Search Report and Written Opinion dated Jun. 16, 2016.
PCT/EP2016/057032 International Search Report and Written Opinion dated Aug. 4, 2016.
PCT/EP2016/057034 International Search Report and Written Opinion dated Aug. 3, 2016.
PCT/EP2017/057775 International Search Report and Written Opinion dated Jul. 7, 2017.
PCT/GB2020/051495 International Search Report and Written Opinion dated Sep. 30, 2020.
PCT/GB2020/051496 International Search Report and Written Opinion dated Oct. 20, 2020.
PCT/GB2020/051497 International Search Report and Written Opinion dated Sep. 17, 2020.
PCT/MT2017/000001 International Search Report and Written Opinion dated Oct. 20, 2017.
Peters et al. Innate lymphoid cells in inflammatory bowel diseases. Immunol Lett. 172:124-131 (2015).
Rimoldi et al. Intestinal immune homeostasis is regulated by the crosstalk between epithelial cells and dendritic cells. Nat Immunol. 6(5):507-514 (2005).
Robinson et al.: A Protease-Resistant Oral Domain Antibody to TNFa Delivers High Concentrations of Active Compound in Ileal Fluid of Subjects with an Ileostomy. 25th United European Gastroenterology Week, Barcelona, Spain [1] (2017).
Rose et al. Identification and biochemical characterization of human plasma soluble IL-7R: lower concentrations in HIV-1-infected patients. J Immunol. 182(12):7389-7397 (2009).
Rose-John: IL-6 trans-signaling via the soluble IL-6 receptor: importance for the pro-inflammatory activities of IL-6. Int. J. Biol. Sci. 8(9):1237-1247 (2012).
Roux et al.: Structural analysis of the nurse shark (new) antigen receptor (NAR): molecular convergence of NAR and unusual mammalian immunoglobulins. PNAS USA 95(20):11804-11809 (1998).
Rudikoff et al. Single amino acid substitution altering antigen-binding Specificity. PNAS USA 79:1979-1983 (1982).
Saerens et al. Identification of a universal VHH framework to graft non-canonical antigen-binding loops of camel single-domain antibodies. J Mol Biol. 352(3):597-607 (2005).
Sakmar et al.: Total synthesis and expression of a gene for the alpha-subunit of bovine rod outer segment guanine nucleotide-binding protein (transducin). Nucleic Acids Research 16(14A):6361-6372 (1988).
Sandborn et al. Certolizumab pegol for the treatment of Crohn's disease. N Engl J Med. 357:228-238 (2007).
Schreiber et al. Maintenance therapy with certolizumab pegol for Crohn's disease. N Engl J Med. 357:239-250 (2007).
Shaji, et al. Protein and Peptide drug delivery: oral approaches. Indian J Pharm Sci. May-Jun.;70(3):269-77 (2008).
Shealy et al.: Characterization of golimumab, a human monoclonal antibody specific for human tumor necrosis factor a. MAbs 2(4):428-439 (2010).
Silverman et al., Multivalent avimer proteins evolved by exon shuffling of a family of human receptor domains. Nat. Biotechnol. 23 (12):1556-1561 (2005).
Siontorou: Nanobodies as novel agents for disease diagnosis and therapy. Int J Nanomedicine 8:4215-4227 (2013).
Skerra: Alternative binding proteins: anticalins—harnessing the structural plasticity of the lipocalin ligand pocket to engineer novel binding activities. FEBS J. 275(11):2677-2683 (2008).
Skerra et al. Assembly of a functional Immunoglobulin Fv fragment in *Escherichia coli*. Science 240(4855):1038-1041 (1988).
STIC report (2019).
Suderman et al.: Development of polyol-responsive antibody mimetics for single-step protein purification. Protein Expr Purif. 134:114-124 (2017).
Tal et al.: Interleukin 7 and thymic stromal lymphopoietin: from immunity to leukemia. Cell Mol Life Sci. 71(3):365-378 (2014).
Tanha et al.: Selection by phage display of llama conventional V(H) fragments with heavy chain antibody V(H)H properties. Journal of Immunological Methods 263(1-2):97-109 (2002).
Teng et al. IL-12 and IL-23 cytokines: from discovery to targeted therapies for immune-mediated inflammatory diseases. Nat Med. 21:719-729 (2015).
Teutsch et al. Identification of 11 novel and common single nucleotide polymorphisms in the interleukin-7 receptor-alpha gene and their associations with multiple sclerosis. Eur J Hum Genet. 11(7):509-515 (2003).
Thomassen et al.: Large-scale production of VHH antibody fragments by *Saccharomyces cerevisiae*. Enzyme and Microbial Technology 30(3):273-278 (2002).
Tsilingiri et al. Thymic Stromal Lymphopoietin: To Cut a Long Story Short. Cell Mol Gastroenterol Hepatol. 3(2):174-182 (2017).

(56) References Cited

OTHER PUBLICATIONS

Ungar et al.: Optimizing Anti-TNF-a Therapy: Serum Levels of Infliximab and Adalimumab Are Associated With Mucosal Healing in Patients With Inflammatory Bowel Diseases. Clin Gastroenterol Hepatol. 14(4):550-557 (2016).
Unger et al.: Selection of nanobodies that block the enzymatic and cytotoxic activities of the binary Clostridium difficile toxin CDT. Scientific Reports 5:7850 [1-10] (2015).
UniProt Database: Uncharacterized protein. Accession No. B5H131, 2 pages (2008) http://www.uniprot.org/uniprot/B5H131.
U.S. Appl. No. 15/273,353 Office Action dated Aug. 16, 2018.
U.S. Appl. No. 15/273,353 Office Action dated Jan. 23, 2018.
U.S. Appl. No. 15/273,353 Office Action dated Jun. 4, 2019.
U.S. Appl. No. 15/717,174 Office Action dated Apr. 22, 2020.
U.S. Appl. No. 15/717,174 Office Action dated Aug. 8, 2019.
U.S. Appl. No. 15/717,174 Office Action dated Mar. 6, 2019.
U.S. Appl. No. 15/717,174 Office Action dated Sep. 16, 2020.
U.S. Appl. No. 15/717,230 Office Action dated Jan. 21, 2020.
U.S. Appl. No. 15/717,230 Office Action dated May 18, 2020.
U.S. Appl. No. 15/717,230 Office Action dated Sep. 3, 2019.
U.S. Appl. No. 16/140,843 Office Action dated Nov. 26, 2019.
U.S. Appl. No. 16/988,506 Office Action dated Oct. 6, 2020.
Van Schie et al.: The antibody response against human and chimeric anti-TNF therapeutic antibodies primarily targets the TNF binding region. Ann Rheum Dis. 74(1):311-314 (2015).
Vandenbroucke et al. Orally administered L. *lactis* secreting an anti-TNF nanobody demonstrate efficacy in chronic colitis. Mucosal Immunology 3(1):49-56 (2010).
Vandeventer: Anti-TNF antibody treatment of Crohn's disease. Ann Rheum Dis. 58(Suppl I):I114-I120 (1999).
Verma et al. Modified oligonucleotides: synthesis and strategy for users. Annu Rev Biochem 67:99-134 (1998).
Verstraete et al. Structure and antagonism of the receptor complex mediated by human TSLP in allergy and asthma. Nat Commun. 8:14937 (2017).
Vetter et al. Emerging oral targeted therapies in inflammatory bowel diseases: opportunities and challenges. Therap Adv Gastroenterol. 10(10):773-790 (2017).
Vincke et al. General strategy to humanize a camelid single-domain antibody and identification of a universal humanized nanobody scaffold. J. Biol. Chem. 284(5):3273-3284 (2009).

Volkel et al.: Optimized linker sequences for the expression of monomeric and dimeric bispecific single-chain diabodies. Protein Eng. 14(10):815-823 (2001).
Vossenkamper et al.: A CD3-specific antibody reduces cytokine production and alters phosphoprotein profiles in intestinal tissues from patients with inflammatory bowel disease. Gastroenterology 147(1):172-183 (2014).
Vu et al.: Comparison of llama VH sequences from conventional and heavy chain antibodies. Molecular Immunology 34(16-17):1121-1131 (1997).
Wahlich et al.: Oral Delivery of a Novel Domain Antibody (VorabodyTM) for the Treatment of Chron's Disease. PEGS Europe Protein & Antibody Engineering Summit, Lisbon, Portugal, 1 page (2017).
Walsh. Structural insights into the common γ-chain family of cytokines and receptors from the interleukin-7 pathway. Immunol Rev. 250(1):303-316 (2012).
Ward et al. Binding activities of a repertoire of single immunoglobulin variable domains secreted from *Escherichia coli*. Nature 341(6242):544-546 (1989).
Wells et al. Cassette mutagenesis: an efficient method for generation of multiple mutations at defined sites. Gene 34:315-323 (1985).
West et al.: Predicting intestinal tract luminal concentrations after oral dosing of an anti-TNFa domain antibody engineered for intestinal protease resistance. VHsquared Antibody Engineering & Therapeutics Meeting, San Diego, USA, 1 page (2017).
Winkler et al. Changing the antigen binding specificity by single point mutations of an anti-p24 (HIV-1) antibody. J Immunol. 165(8):4505-4514 (2000).
Yan et al. Construction of a synthetic phage-displayed Nanobody library with CDR3 regions randomized by trinucleotide cassettes for diagnostic applications. Journal of Translational Medicine 12:343 (2014).
Yu et al., Interaction between Bevacizumab and Murine VEGF-A: A Reassessment. Investigative Ophthalmology & Visual Science 49(2):522-527 (2008).
Zabetakis et al. Contributions of the complementarity determining regions to the thermal stability of a single-domain antibody. PLoS One 8(10):e77678 (2013).
U.S. Appl. No. 16/821,287 Office Action dated Oct. 21, 2022.

* cited by examiner

SEQUENCE LISTING

```
<160> NUMBER OF SEQ ID NOS: 89

<210> SEQ ID NO 1
<211> LENGTH: 5
```

```
<212> TYPE: PRT
<213> ORGANISM: Artificial Sequence
<220> FEATURE:
<223> OTHER INFORMATION: Synthetic Sequence

<400> SEQUENCE: 1

Ser Asp Ala Met Gly
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 2

Ala Ile Gly Trp Ser Gly Ala Val Thr His Tyr Ser Asp Ser Val Lys
1               5                   10                  15

Gly

<210> SEQ ID NO 3
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 3

Asp Tyr Asp Thr Asp Val Trp Gln Tyr
1               5

<210> SEQ ID NO 4
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 4

Asp Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser
            20                  25                  30

<210> SEQ ID NO 5
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 5

Trp Phe Arg Gln Ala Pro Gly Lys Glu Leu Glu Phe Leu Ala
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 6

Arg Phe Thr Ile Ser Arg Asp Asn Ala Lys Asn Thr Val Tyr Leu Gln
1               5                   10                  15
```

```
Met Asn Ser Leu Arg Ala Glu Asp Thr Gly Arg Tyr Tyr Cys Ala Glu
            20                  25                  30

<210> SEQ ID NO 7
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 7

Trp Gly Gln Gly Thr Gln Val Thr Val Ser Ser
1               5                   10

<210> SEQ ID NO 8
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 8

Asp Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Leu Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 9
<211> LENGTH: 118
<212> TYPE: PRT
<213> ORGANISM: Lama glama

<400> SEQUENCE: 9

Glu Val Gln Leu Val Glu Ser Gly Gly Gly Leu Val Gln Ala Gly Gly
1               5                   10                  15

Ser Leu Arg Leu Ser Cys Glu Ser Ala Arg Thr Phe Ser Asp Asp
            20                  25                  30

Ala Met Gly Trp Phe Arg Gln Ala Ala Gly Lys Glu Arg Glu Phe Leu
        35                  40                  45

Ala Ala Ile Asn Trp Ser Gly Ala Val Thr His Tyr Gly Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Glu Asp Tyr Asp Thr Asp Val Trp Gln His Trp Gly Gln Gly Thr
            100                 105                 110
```

Gln Val Thr Val Ser Ser
        115

<210> SEQ ID NO 10
<211> LENGTH: 118
<212> TYPE: PRT
<213> ORGANISM: Lama glama

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 11
<211> LENGTH: 118
<212> TYPE: PRT
<213> ORGANISM: Lama glama

<400> SEQUENCE: 11

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 12
<211> LENGTH: 118
<212> TYPE: PRT
<213> ORGANISM: Lama glama

<400> SEQUENCE: 12

Glu Val Gln Leu Val Glu Ser Gly Gly Gly Leu Val Gln Ala Gly Gly
1               5                   10                  15

Ser Leu Arg Leu Ser Cys Glu Ser Ile Gly Thr Phe Ser Ser Asp
            20                  25                  30

Ala Met Gly Trp Phe Arg Gln Ala Pro Gly Lys Glu Arg Glu Phe Leu
            35                  40                  45

Ala Ala Ile Gly Trp Ser Gly Thr Val Thr His Tyr Ser Asp Ser Val
 50                  55                  60

Gln Gly Arg Phe Thr Ile Ser Arg Asp Asn Ala Lys Asn Thr Val Tyr
 65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
                100                 105                 110

Gln Val Thr Val Ser Ser
            115

<210> SEQ ID NO 13
<211> LENGTH: 118
<212> TYPE: PRT
<213> ORGANISM: Lama glama

<400> SEQUENCE: 13

Glu Val Gln Leu Val Glu Ser Gly Gly Gly Leu Val Gln Val Gly Gly
 1               5                  10                  15

Ser Leu Arg Leu Ser Cys Glu Ser Ile Ser Thr Phe Ser Ser Asp
            20                  25                  30

Ala Met Gly Trp Phe Arg Gln Ala Pro Gly Lys Glu Arg Glu Phe Leu
            35                  40                  45

Ala Ala Ile Gly Trp Ser Gly Ala Val Thr His Tyr Ser Asp Ser Val
 50                  55                  60

Gln Gly Arg Phe Thr Ile Ser Arg Asp Asn Ala Lys Asn Thr Val Tyr
 65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
                100                 105                 110

Gln Val Thr Val Ser Ser
            115

<210> SEQ ID NO 14
<211> LENGTH: 118
<212> TYPE: PRT
<213> ORGANISM: Lama glama

<400> SEQUENCE: 14

Glu Val Gln Leu Val Glu Ser Gly Gly Gly Leu Val Gln Ala Gly Gly
 1               5                  10                  15

Ser Leu Arg Leu Ser Cys Glu Ser Ile Ser Thr Phe Gly Ser Asp
            20                  25                  30

Ala Met Gly Trp Phe Arg Gln Ala Pro Gly Lys Glu Arg Glu Phe Val
            35                  40                  45

Ala Ala Thr Gly Trp Ser Gly Ala Val Thr His Tyr Ser Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Ser Glu Asp Thr Gly Tyr Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 15
<211> LENGTH: 118
<212> TYPE: PRT
<213> ORGANISM: Lama glama

<400> SEQUENCE: 15

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Val Thr Asp Val Trp Gln Tyr Trp Gly Gln Gly Thr
            100                 105                 110

Gln Val Thr Val Ser Ser
        115

<210> SEQ ID NO 16
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 16

Glu Val Gln Leu Val Glu Ser Gly Gly Gly Leu Val Gln Ala Gly Gly
1               5                   10                  15

Ser Leu Arg Leu Ser Cys Ala Ser Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 17
<211> LENGTH: 118
<212> TYPE: PRT
<213> ORGANISM: Artificial Sequence
<220> FEATURE:
<223> OTHER INFORMATION: Synthetic Sequence

```
<400> SEQUENCE: 17

Glu Val Gln Leu Val Glu Ser Gly Gly Gly Leu Val Gln Ala Gly Gly
1               5                   10                  15

Ser Leu Arg Leu Ser Cys Ser Ser Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 18
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 18

Glu Val Gln Leu Val Glu Ser Gly Gly Gly Leu Val Gln Ala Gly Gly
1               5                   10                  15

Ser Leu Arg Leu Ser Cys Glu Ala Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 19
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 19

Glu Val Gln Leu Val Glu Ser Gly Gly Gly Leu Val Gln Ala Gly Gly
1               5                   10                  15

Ser Leu Arg Leu Ser Cys Glu Ser Ser Gly Ser Thr Phe Ser Ser Asp
            20                  25                  30

Ala Met Gly Trp Phe Arg Gln Ala Pro Gly Lys Glu Arg Glu Phe Leu
        35                  40                  45
```

Ala Ala Ile Gly Trp Ser Gly Ala Val Thr His Tyr Ser Asp Ser Val
            50                  55                  60

Gln Gly Arg Phe Thr Ile Ser Arg Asp Asn Ala Lys Asn Thr Val Tyr
 65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 20
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 20

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Val Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 21
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 21

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Leu Glu Trp Val
        35                  40                  45

Ser Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr

Gln Val Thr Val Ser Ser
        115

<210> SEQ ID NO 22
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 22

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Leu Glu Trp Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 23
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 23

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 24
<211> LENGTH: 118
<212> TYPE: PRT
<213> ORGANISM: Artificial Sequence
<220> FEATURE:

```
<223> OTHER INFORMATION: Synthetic Sequence

<400> SEQUENCE: 24

Glu Val Gln Leu Val Glu Ser Gly Gly Gly Leu Val Gln Ala Gly Gly
1               5                   10                  15

Ser Leu Arg Leu Ser Cys Glu Ser Ile Ser Thr Phe Ser Ser Asp
            20                  25                  30

Ala Met Gly Trp Phe Arg Gln Ala Pro Gly Lys Glu Leu Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 25
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 25

Glu Val Gln Leu Val Glu Ser Gly Gly Gly Leu Val Gln Ala Gly Gly
1               5                   10                  15

Ser Leu Arg Leu Ser Cys Glu Ser Ile Ser Thr Phe Ser Ser Asp
            20                  25                  30

Ala Met Gly Trp Phe Arg Gln Ala Pro Gly Lys Glu Arg Glu Trp Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 26
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 26

Glu Val Gln Leu Val Glu Ser Gly Gly Gly Leu Val Gln Ala Gly Gly
1               5                   10                  15

Ser Leu Arg Leu Ser Cys Glu Ser Ile Ser Thr Phe Ser Ser Asp
            20                  25                  30

Ala Met Gly Trp Phe Arg Gln Ala Pro Gly Lys Glu Arg Glu Phe Val
```

```
            35                  40                  45
Ala Ala Ile Gly Trp Ser Gly Ala Val Thr His Tyr Ser Asp Ser Val
    50                  55                  60
Gln Gly Arg Phe Thr Ile Ser Arg Asp Asn Ala Lys Asn Thr Val Tyr
65                  70                  75                  80
Leu Gln Met Asn Ser Leu Lys Ser Glu Asp Thr Gly Arg Tyr Tyr Cys
                85                  90                  95
Ala Glu Asp Tyr Asp Thr Asp Val Trp Gln Tyr Trp Gly Gln Gly Thr
            100                 105                 110
Gln Val Thr Val Ser Ser
            115

<210> SEQ ID NO 27
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 27

Glu Val Gln Leu Val Glu Ser Gly Gly Gly Leu Val Gln Ala Gly Gly
1               5                   10                  15
Ser Leu Arg Leu Ser Cys Glu Ser Ser Ile Ser Thr Phe Ser Ser Asp
                20                  25                  30
Ala Met Gly Trp Phe Arg Gln Ala Pro Gly Lys Glu Arg Glu Phe Leu
            35                  40                  45
Ser Ala Ile Gly Trp Ser Gly Ala Val Thr His Tyr Ser Asp Ser Val
    50                  55                  60
Gln Gly Arg Phe Thr Ile Ser Arg Asp Asn Ala Lys Asn Thr Val Tyr
65                  70                  75                  80
Leu Gln Met Asn Ser Leu Lys Ser Glu Asp Thr Gly Arg Tyr Tyr Cys
                85                  90                  95
Ala Glu Asp Tyr Asp Thr Asp Val Trp Gln Tyr Trp Gly Gln Gly Thr
            100                 105                 110
Gln Val Thr Val Ser Ser
            115

<210> SEQ ID NO 28
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 28

Glu Val Gln Leu Val Glu Ser Gly Gly Gly Leu Val Gln Ala Gly Gly
1               5                   10                  15
Ser Leu Arg Leu Ser Cys Glu Ser Ser Ile Ser Thr Phe Ser Ser Asp
                20                  25                  30
Ala Met Gly Trp Phe Arg Gln Ala Pro Gly Lys Glu Arg Glu Phe Leu
            35                  40                  45
Ala Ala Ile Gly Trp Ser Gly Ala Val Thr His Tyr Ser Asp Ser Val
    50                  55                  60
Lys Gly Arg Phe Thr Ile Ser Arg Asp Asn Ala Lys Asn Thr Val Tyr
65                  70                  75                  80
Leu Gln Met Asn Ser Leu Lys Ser Glu Asp Thr Gly Arg Tyr Tyr Cys
                85                  90                  95
```

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 29
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 29

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 30
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 30

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Arg Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 31
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 31

Glu Val Gln Leu Val Glu Ser Gly Gly Gly Leu Val Gln Ala Gly Gly
1               5                   10                  15

Ser Leu Arg Leu Ser Cys Glu Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 32
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 32

Glu Val Gln Leu Val Glu Ser Gly Gly Gly Leu Val Gln Ala Gly Gly
1               5                   10                  15

Ser Leu Arg Leu Ser Cys Glu Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Thr Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 33
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 33

Glu Val Gln Leu Val Glu Ser Gly Gly Gly Leu Val Gln Ala Gly Gly
1               5                   10                  15

Ser Leu Arg Leu Ser Cys Glu Ser Ile Ser Thr Phe Ser Ser Asp
            20                  25                  30

Ala Met Gly Trp Phe Arg Gln Ala Pro Gly Lys Glu Arg Glu Phe Leu
            35                  40                  45

Ala Ala Ile Gly Trp Ser Gly Ala Val Thr His Tyr Ser Asp Ser Val
        50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Ala Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
            115

<210> SEQ ID NO 34
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 34

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Arg Glu Phe Leu
            35                  40                  45

Ala Ala Ile Gly Trp Ser Gly Ala Val Thr His Tyr Ser Asp Ser Val
        50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Val Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
            115

<210> SEQ ID NO 35
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 35

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Arg Glu Phe Leu
            35                  40                  45

Ala Ala Ile Gly Trp Ser Gly Ala Val Thr His Tyr Ser Asp Ser Val
        50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Leu Val Thr Val Ser Ser
        115

<210> SEQ ID NO 36
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 36

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Leu Glu Trp Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 37
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 37

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Leu Glu Trp Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 38
<211> LENGTH: 118
<212> TYPE: PRT

```
<213> ORGANISM: Artificial Sequence
<220> FEATURE:
<223> OTHER INFORMATION: Synthetic Sequence

<400> SEQUENCE: 38

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Trp Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 39

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Leu Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 40

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30
```

Ala Met Gly Trp Phe Arg Gln Ala Pro Gly Lys Gly Leu Glu Trp Leu
            35                  40                  45

Ala Ala Ile Gly Trp Ser Gly Ala Val Thr His Tyr Ser Asp Ser Val
        50                  55                  60

Gln Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
            115

<210> SEQ ID NO 41
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 41

Glu Val Gln Leu Val Glu Ser Gly Gly Gly Leu Val Gln Ala Gly Gly
1               5                   10                  15

Ser Leu Arg Leu Ser Cys Ala Ser Ile Ser Thr Phe Ser Ser Asp
            20                  25                  30

Ala Met Gly Trp Phe Arg Gln Ala Pro Gly Lys Glu Arg Glu Phe Leu
            35                  40                  45

Ala Ala Ile Gly Trp Ser Gly Ala Val Thr His Tyr Ser Asp Ser Val
        50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
            115

<210> SEQ ID NO 42
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 42

Glu Val Gln Leu Val Glu Ser Gly Gly Gly Leu Val Gln Ala Gly Gly
1               5                   10                  15

Ser Leu Arg Leu Ser Cys Glu Ser Ile Ser Thr Phe Ser Ser Asp
            20                  25                  30

Ala Met Gly Trp Phe Arg Gln Ala Pro Gly Lys Gly Leu Glu Trp Leu
            35                  40                  45

Ala Ala Ile Gly Trp Ser Gly Ala Val Thr His Tyr Ser Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ser Glu Asp Thr Gly Arg Tyr Tyr Cys

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 43
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 43

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 44

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 45
<211> LENGTH: 118

```
<212> TYPE: PRT
<213> ORGANISM: Artificial Sequence
<220> FEATURE:
<223> OTHER INFORMATION: Synthetic Sequence

<400> SEQUENCE: 45

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Arg Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 46
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 46

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 47
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 47

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
```

```
                    20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ser Glu Asp Thr Gly Arg Tyr Tyr Cys
                85                  90                  95

Ala Glu Asp Tyr Asp Thr Asp Val Trp Gln Tyr Trp Gly Gln Gly Thr
                100                 105                 110

Gln Val Thr Val Ser Ser
            115

<210> SEQ ID NO 48
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 48

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
                20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Gly Arg Tyr Tyr Cys
                85                  90                  95

Ala Glu Asp Tyr Asp Thr Asp Val Trp Gln Tyr Trp Gly Gln Gly Thr
                100                 105                 110

Gln Val Thr Val Ser Ser
            115

<210> SEQ ID NO 49
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 49

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
                20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80
```

```
Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 50
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 50

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 51
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 51

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 52
```

```
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 52

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 53
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 53

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 54
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 54

Asp Val Gln Leu Val Glu Ser Gly Gly Gly Leu Val Gln Ala Gly Gly
1               5                   10                  15
```

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Leu Glu Trp Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 55
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 55

Asp Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 56
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 56

Asp Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 57

Asp Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ser Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 58

Asp Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

```
<210> SEQ ID NO 59
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 59
```

Asp Val Gln Leu Val Glu Ser Gly Gly Gly Leu Val Gln Ala Gly Gly
1               5                   10                  15

Ser Leu Arg Leu Ser Cys Glu Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

```
<210> SEQ ID NO 60
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 60
```

Asp Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Gly Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

```
<210> SEQ ID NO 61
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 61
```

Asp Val Gln Leu Val Glu Ser Gly Gly Gly Leu Val Gln Ala Gly Gly
1               5                   10                  15

-continued

```
Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 62
<211> LENGTH: 159
<212> TYPE: PRT
<213> ORGANISM: Artificial Sequence
<220> FEATURE:
<223> OTHER INFORMATION: Synthetic Sequence

<400> SEQUENCE: 62

Met Phe Pro Phe Ala Leu Leu Tyr Val Leu Ser Val Ser Phe Arg Lys
 1               5                  10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
 50                  55                  60

Asn Thr Val Ser Cys Ser Asn Arg Pro His Cys Leu Thr Glu Ile Gln
 65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
    130                 135                 140

Gln Gly Leu Trp Arg Arg Phe Asn Arg Pro Leu Leu Lys Gln Gln
145                 150                 155

<210> SEQ ID NO 63
<211> LENGTH: 63
<212> TYPE: PRT
<213> ORGANISM: Artificial Sequence
<220> FEATURE:
<223> OTHER INFORMATION: Synthetic Sequence

<400> SEQUENCE: 63

Met Phe Ala Met Lys Thr Lys Ala Ala Leu Ala Ile Trp Cys Pro Gly
 1               5                  10                  15

Tyr Ser Glu Thr Gln Ile Asn Ala Thr Gln Ala Met Lys Lys Arg Arg
            20                  25                  30

Lys Arg Lys Val Thr Thr Asn Lys Cys Leu Glu Gln Val Ser Gln Leu
```

-continued

```
                35                  40                  45
Gln Gly Leu Trp Arg Arg Phe Asn Arg Pro Leu Leu Lys Gln Gln
     50                  55                  60

<210> SEQ ID NO 64
<211> LENGTH: 369
<212> TYPE: PRT
<213> ORGANISM: Artificial Sequence
<220> FEATURE:
<223> OTHER INFORMATION: Synthetic Sequence

<400> SEQUENCE: 64

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
        275                 280                 285

Arg Ile Pro Thr Leu Lys Asn Leu Glu Asp Leu Val Thr Glu Tyr His
    290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
```

```
                    340                 345                 350
Gln His Ser Pro Tyr Trp Ala Pro Pro Cys Tyr Thr Leu Lys Pro Glu
        355                 360                 365
Thr

<210> SEQ ID NO 65
<211> LENGTH: 439
<212> TYPE: PRT
<213> ORGANISM: Artificial Sequence
<220> FEATURE:
<223> OTHER INFORMATION: Synthetic Sequence

<400> SEQUENCE: 65

Glu Ser Gly Tyr Ala Gln Asn Gly Asp Leu Glu Asp Ala Glu Leu Asp
1               5                   10                  15

Asp Tyr Ser Phe Ser Cys Tyr Ser Gln Leu Glu Val Asn Gly Ser Gln
            20                  25                  30

His Ser Leu Thr Cys Ala Phe Glu Asp Pro Asp Val Asn Thr Thr Asn
        35                  40                  45

Leu Glu Phe Glu Ile Cys Gly Ala Leu Val Glu Val Lys Cys Leu Asn
    50                  55                  60

Phe Arg Lys Leu Gln Glu Ile Tyr Phe Ile Glu Thr Lys Lys Phe Leu
65                  70                  75                  80

Leu Ile Gly Lys Ser Asn Ile Cys Val Lys Val Gly Glu Lys Ser Leu
                85                  90                  95

Thr Cys Lys Lys Ile Asp Leu Thr Thr Ile Val Lys Pro Glu Ala Pro
            100                 105                 110

Phe Asp Leu Ser Val Ile Tyr Arg Glu Gly Ala Asn Asp Phe Val Val
        115                 120                 125

Thr Phe Asn Thr Ser His Leu Gln Lys Lys Tyr Val Lys Val Leu Met
    130                 135                 140

His Asp Val Ala Tyr Arg Gln Glu Lys Asp Glu Asn Lys Trp Thr His
145                 150                 155                 160

Val Asn Leu Ser Ser Thr Lys Leu Thr Leu Leu Gln Arg Lys Leu Gln
                165                 170                 175

Pro Ala Ala Met Tyr Glu Ile Lys Val Arg Ser Ile Pro Asp His Tyr
            180                 185                 190

Phe Lys Gly Phe Trp Ser Glu Trp Ser Pro Ser Tyr Tyr Phe Arg Thr
        195                 200                 205

Pro Glu Ile Asn Asn Ser Ser Gly Glu Met Asp Pro Ile Leu Leu Thr
    210                 215                 220

Ile Ser Ile Leu Ser Phe Phe Ser Val Ala Leu Leu Val Ile Leu Ala
225                 230                 235                 240

Cys Val Leu Trp Lys Lys Arg Ile Lys Pro Ile Val Trp Pro Ser Leu
                245                 250                 255

Pro Asp His Lys Lys Thr Leu Glu His Leu Cys Lys Lys Pro Arg Lys
            260                 265                 270

Asn Leu Asn Val Ser Phe Asn Pro Glu Ser Phe Leu Asp Cys Gln Ile
        275                 280                 285

His Arg Val Asp Asp Ile Gln Ala Arg Asp Glu Val Glu Gly Phe Leu
    290                 295                 300

Gln Asp Thr Phe Pro Gln Gln Leu Glu Glu Ser Glu Lys Gln Arg Leu
305                 310                 315                 320

Gly Gly Asp Val Gln Ser Pro Asn Cys Pro Ser Glu Asp Val Val Ile
                325                 330                 335
```

```
Thr Pro Glu Ser Phe Gly Arg Asp Ser Ser Leu Thr Cys Leu Ala Gly
            340                 345                 350

Asn Val Ser Ala Cys Asp Ala Pro Ile Leu Ser Ser Arg Ser Leu
            355                 360                 365

Asp Cys Arg Glu Ser Gly Lys Asn Gly Pro His Val Tyr Gln Asp Leu
370                 375                 380

Leu Leu Ser Leu Gly Thr Thr Asn Ser Thr Leu Pro Pro Phe Ser
385                 390                 395                 400

Leu Gln Ser Gly Ile Leu Thr Leu Asn Pro Val Ala Gln Gly Gln Pro
            405                 410                 415

Ile Leu Thr Ser Leu Gly Ser Asn Gln Glu Ala Tyr Val Thr Met
            420                 425                 430

Ser Ser Phe Tyr Gln Asn Gln
            435

<210> SEQ ID NO 66
<211> LENGTH: 439
<212> TYPE: PRT
<213> ORGANISM: Artificial Sequence
<220> FEATURE:
<223> OTHER INFORMATION: Synthetic Sequence

<400> SEQUENCE: 66

Glu Ser Gly Tyr Ala Gln Asn Gly Asp Leu Glu Asp Ala Glu Leu Asp
1               5                   10                  15

Asp Tyr Ser Phe Ser Cys Tyr Ser Gln Leu Glu Val Asn Gly Ser Gln
            20                  25                  30

His Ser Leu Thr Cys Ala Phe Glu Asp Pro Asp Val Asn Thr Thr Asn
        35                  40                  45

Leu Glu Phe Glu Ile Cys Gly Ala Leu Val Glu Val Lys Cys Leu Ser
    50                  55                  60

Phe Arg Lys Leu Gln Glu Ile Tyr Phe Ile Glu Thr Lys Lys Phe Leu
65                  70                  75                  80

Leu Ile Gly Lys Ser Asn Ile Cys Val Lys Val Gly Gly Lys Ser Leu
                85                  90                  95

Thr Cys Lys Lys Ile Asp Leu Thr Thr Ile Val Lys Pro Glu Ala Pro
            100                 105                 110

Phe Asp Leu Ser Val Ile Tyr Arg Glu Gly Ala Asn Asp Phe Val Val
        115                 120                 125

Thr Phe Asn Thr Ser His Leu Gln Lys Lys Tyr Val Lys Val Leu Met
    130                 135                 140

His Asp Val Ala Tyr Arg Gln Glu Lys Asp Glu Asn Lys Trp Met His
145                 150                 155                 160

Val Asn Leu Ser Ser Thr Lys Leu Thr Leu Leu Gln Arg Asn Leu Gln
                165                 170                 175

Pro Glu Ala Met Tyr Glu Ile Lys Val Arg Ser Ile Pro Asp His Tyr
            180                 185                 190

Phe Lys Gly Phe Trp Ser Glu Trp Ser Pro Ser Tyr Tyr Phe Arg Thr
        195                 200                 205

Pro Glu Ile Asn Asn Ser Pro Gly Glu Met Asp Pro Ile Leu Leu Thr
    210                 215                 220

Ile Ser Leu Leu Ser Phe Phe Ser Val Ala Leu Leu Val Ile Leu Ala
225                 230                 235                 240

Cys Val Leu Trp Lys Lys Arg Ile Lys Pro Ile Val Trp Pro Ser Leu
                245                 250                 255
```

```
Pro Asp His Lys Lys Thr Leu Glu His Leu Cys Lys Lys Pro Arg Lys
            260                 265                 270

Asn Leu Asn Val Ser Phe Asn Pro Glu Ser Phe Leu Asp Cys Gln Ile
            275                 280                 285

His Arg Val Asp Asp Ile Gln Ala Arg Asp Glu Val Glu Gly Phe Leu
            290                 295                 300

Gln Asp Thr Phe Pro Gln Gln Leu Glu Glu Ser Lys Lys Gln Arg Leu
305                 310                 315                 320

Gly Gly Asp Val Gln Ser Pro Ser Cys Pro Ser Glu Asp Val Val Ile
                    325                 330                 335

Thr Pro Glu Ser Phe Glu Arg Asp Ser Ser Leu Arg Cys Leu Ala Gly
            340                 345                 350

Asn Val Ser Ala Cys Asp Ala Pro Ile Leu Ser Ser Arg Ser Leu
            355                 360                 365

Asp Cys Arg Glu Ser Gly Lys Asn Gly Pro His Val Tyr Gln Asp Leu
            370                 375                 380

Leu Leu Ser Leu Gly Thr Thr Asn Ser Thr Leu Pro Pro Phe Ser
385                 390                 395                 400

Leu Gln Ser Gly Ile Leu Thr Leu Asn Pro Val Ala Gln Gly Gln Pro
                    405                 410                 415

Ile Leu Thr Ser Leu Gly Ser Asn Gln Glu Glu Ala Tyr Val Thr Met
                    420                 425                 430

Ser Ser Phe Tyr Gln Asn Gln
            435

<210> SEQ ID NO 67
<211> LENGTH: 220
<212> TYPE: PRT
<213> ORGANISM: Artificial Sequence
<220> FEATURE:
<223> OTHER INFORMATION: Synthetic Sequence

<400> SEQUENCE: 67

Glu Ser Gly Tyr Ala Gln Asn Gly Asp Leu Glu Asp Ala Glu Leu Asp
1               5                   10                  15

Asp Tyr Ser Phe Ser Cys Tyr Ser Gln Leu Glu Val Asn Gly Ser Gln
                20                  25                  30

His Ser Leu Thr Cys Ala Phe Glu Asp Pro Asp Val Asn Thr Thr Asn
            35                  40                  45

Leu Glu Phe Glu Ile Cys Gly Ala Leu Val Glu Val Lys Cys Leu Ser
    50                  55                  60

Phe Arg Lys Leu Gln Glu Ile Tyr Phe Ile Glu Thr Lys Lys Phe Leu
65                  70                  75                  80

Leu Ile Gly Lys Ser Asn Ile Cys Val Lys Val Gly Gly Lys Ser Leu
                85                  90                  95

Thr Cys Lys Lys Ile Asp Leu Thr Thr Ile Val Lys Pro Glu Ala Pro
            100                 105                 110

Phe Asp Leu Ser Val Ile Tyr Arg Glu Gly Ala Asn Asp Phe Val Val
            115                 120                 125

Thr Phe Asn Thr Ser His Leu Gln Lys Lys Tyr Val Lys Val Leu Met
        130                 135                 140

His Asp Val Ala Tyr Arg Gln Glu Lys Asp Glu Asn Lys Trp Met His
145                 150                 155                 160

Val Asn Leu Ser Ser Thr Lys Leu Thr Leu Leu Gln Arg Asn Leu Gln
                165                 170                 175
```

```
Pro Glu Ala Met Tyr Glu Ile Lys Val Arg Ser Ile Pro Asp His Tyr
            180                 185                 190

Phe Lys Gly Phe Trp Ser Glu Trp Ser Pro Ser Tyr Tyr Phe Arg Thr
            195                 200                 205

Pro Glu Ile Asn Asn Ser Pro Gly Glu Met Asp Pro
            210                 215                 220

<210> SEQ ID NO 68
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 68

Glu Ser Gly Tyr Ala Gln Asn Gly Asp Leu Glu Asp Ala Glu Leu Asp
1               5                   10                  15

Asp Tyr Ser Phe Ser Cys Tyr Ser Gln Leu Glu Val Asn Gly Ser Gln
            20                  25                  30

His Ser Leu Thr Cys Ala Phe Glu Asp Pro Asp Val Asn Thr Thr Asn
        35                  40                  45

Leu Glu Phe Glu Ile Cys Gly Ala Leu Val Glu Val Lys Cys Leu Asn
    50                  55                  60

Phe Arg Lys Leu Gln Glu Ile Tyr Phe Ile Glu Thr Lys Lys Phe Leu
65                  70                  75                  80

Leu Ile Gly Lys Ser Asn Ile Cys Val Lys Val Gly Glu Lys Ser Leu
                85                  90                  95

Thr Cys Lys Lys Ile Asp Leu Thr Thr Ile Val Lys Pro Glu Ala Pro
            100                 105                 110

Phe Asp Leu Ser Val Ile Tyr Arg Glu Gly Ala Asn Asp Phe Val Val
        115                 120                 125

Thr Phe Asn Thr Ser His Leu Gln Lys Lys Tyr Val Lys Val Leu Met
    130                 135                 140

His Asp Val Ala Tyr Arg Gln Glu Lys Asp Glu Asn Lys Trp Thr His
145                 150                 155                 160

Val Asn Leu Ser Ser Thr Lys Leu Thr Leu Leu Gln Arg Lys Leu Gln
                165                 170                 175

Pro Ala Ala Met Tyr Glu Ile Lys Val Arg Ser Ile Pro Asp His Tyr
            180                 185                 190

Phe Lys Gly Phe Trp Ser Glu Trp Ser Pro Ser Tyr Tyr Phe Arg Thr
            195                 200                 205

Pro Glu Ile Asn Asn Ser Ser Gly Glu Met Asp
        210                 215

<210> SEQ ID NO 69
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 69
gatgttcaat tggttgaatc tggtggtggt tggttcaag ccggtggttc tttgagattg      60
tcttgtgaat cttctatctc caccttctca tctgatgcta tgggttggtt tagacaagct    120
ccaggtaaag aaagagaatt tttggctgct attggtggga gtggtgctgt tactcattat    180
tccgattctg ttaaaggtcg tttcaccatt tctagagata cgctaagaa caccgtctac    240
```

```
ttgcaaatga actctttgag agctgaagat accggtagat attactgcgc tgaagattac      300
gatactgatg tttggcaata ttggggtcaa ggtactcaag ttactgtctc ctcat           355
```

<210> SEQ ID NO 70
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 70

```
gatgttcaat tggttgaatc tggtggtggt ttggttcaag ccggtggttc tttgagattg      60
tcttgtgaat cttctatctc caccttctca tctgatgcta tgggttggtt tagacaagct     120
ccaggtaaag aattggaatt tttggctgct attggtggga gtggtgctgt tactcattat     180
tccgattctg ttaaaggtcg tttcaccatt tctagagata cgctaagaa caccgtctac      240 ttgcaaatga actctttgag agctgaagat accggtagat attactgcgc tgaagattac      300
gatactgatg tttggcaata ttggggtcaa ggtactcaag ttactgtctc ctcat           355
```

<210> SEQ ID NO 71
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 71

```
Asp Asp Ala Met Gly
1               5
```

<210> SEQ ID NO 72
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 72

```
Ala Ile Gly Trp Ser Gly Ala Val Thr His Tyr Ser Asp Ser Val Gln
1               5                   10                  15

Gly
```

<210> SEQ ID NO 73
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 73

```
Ala Ile Gly Trp Ser Gly Thr Val Thr His Tyr Ser Asp Ser Val Gln
1               5                   10                  15

Gly
```

<210> SEQ ID NO 74
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 74

```
Ala Thr Gly Trp Ser Gly Ala Val Thr His Tyr Ser Asp Ser Val Lys
1               5                   10                  15

Gly

<210> SEQ ID NO 75
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 75

Ala Ile Asn Trp Ser Gly Ala Val Thr His Tyr Gly Asp Ser Val Lys
1               5                   10                  15

Gly

<210> SEQ ID NO 76
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 76

Ala Ile Gly Trp Ser Gly Ala Val Thr His Tyr Ser Asp Ser Val Lys
1               5                   10                  15

Gly

<210> SEQ ID NO 77
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 77

Asp Tyr Val Thr Asp Val Trp Gln Tyr
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 78

Asp Tyr Asp Thr Asp Val Trp Gln His
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 79

Glu Leu Glu Phe Leu Ala
1               5

<210> SEQ ID NO 80
<211> LENGTH: 6
<212> TYPE: PRT
```

```
<213> ORGANISM: Artificial Sequence
<220> FEATURE:
<223> OTHER INFORMATION: Synthetic Sequence

<400> SEQUENCE: 80

Gly Leu Glu Trp Val Ser
1               5

<210> SEQ ID NO 81
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 81
tcttaactag tgaggagacg gtgacctg                                    28

<210> SEQ ID NO 82
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (1)..(1)
<223> OTHER INFORMATION: Ser or Asp

<400> SEQUENCE: 82

Xaa Asp Ala Met Gly
1               5

<210> SEQ ID NO 83
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (2)..(2)
<223> OTHER INFORMATION: Ile or Thr
<220> FEATURE:
<221> NAME/KEY: MOD_RES
<222> LOCATION: (3)..(3)
<223> OTHER INFORMATION: Gly or Asn
<220> FEATURE:
<221> NAME/KEY: MOD_RES
<222> LOCATION: (7)..(7)
<223> OTHER INFORMATION: Ala or Thr
<220> FEATURE:
<221> NAME/KEY: MOD_RES
<222> LOCATION: (12)..(12)
<223> OTHER INFORMATION: Ser or Gly
<220> FEATURE:
<221> NAME/KEY: MOD_RES
<222> LOCATION: (16)..(16)
<223> OTHER INFORMATION: Gln or Lys

<400> SEQUENCE: 83

Ala Xaa Xaa Trp Ser Gly Xaa Val Thr His Tyr Xaa Asp Ser Val Xaa
1               5                   10                  15
Gly

<210> SEQ ID NO 84
<211> LENGTH: 9
<212> TYPE: PRT
<213> ORGANISM: Artificial Sequence
<220> FEATURE:
```

```
<223> OTHER INFORMATION: Synthetic Sequence
<220> FEATURE:
<221> NAME/KEY: MOD_RES
<222> LOCATION: (3)..(3)
<223> OTHER INFORMATION: Asp or Val
<220> FEATURE:
<221> NAME/KEY: MOD_RES
<222> LOCATION: (9)..(9)
<223> OTHER INFORMATION: Tyr or His

<400> SEQUENCE: 84

Asp Tyr Xaa Thr Asp Val Trp Gln Xaa
1               5

<210> SEQ ID NO 85
<211> LENGTH: 2310
<212> TYPE: PRT
<213> ORGANISM: Artificial Sequence
<220> FEATURE:
<223> OTHER INFORMATION: Synthetic Sequence
<220> FEATURE:
<221> NAME/KEY: SITE
<222> LOCATION: (2)..(10)
<223> OTHER INFORMATION: This region may encompass 0-9 Gly residues,
      wherein some positions may be absent
<220> FEATURE:
<221> NAME/KEY: SITE
<222> LOCATION: (12)..(110)
<223> OTHER INFORMATION: This region may encompass 0-9 "(Gly)n Ser"
      repeating units, wherein n = 1-10 and some positions may be absent
<220> FEATURE:
<221> NAME/KEY: SITE
<222> LOCATION: (13)..(21)
<223> OTHER INFORMATION: This region may encompass 0-9 Gly residues,
      wherein some positions may be absent
<220> FEATURE:
<221> NAME/KEY: SITE
<222> LOCATION: (24)..(32)
<223> OTHER INFORMATION: This region may encompass 0-9 Gly residues,
      wherein some positions may be absent
<220> FEATURE:
<221> NAME/KEY: SITE
<222> LOCATION: (35)..(43)
<223> OTHER INFORMATION: This region may encompass 0-9 Gly residues,
      wherein some positions may be absent
<220> FEATURE:
<221> NAME/KEY: SITE
<222> LOCATION: (46)..(54)
<223> OTHER INFORMATION: This region may encompass 0-9 Gly residues,
      wherein some positions may be absent
<220> FEATURE:
<221> NAME/KEY: SITE
<222> LOCATION: (57)..(65)
<223> OTHER INFORMATION: This region may encompass 0-9 Gly residues,
      wherein some positions may be absent
<220> FEATURE:
<221> NAME/KEY: SITE
<222> LOCATION: (68)..(76)
<223> OTHER INFORMATION: This region may encompass 0-9 Gly residues,
      wherein some positions may be absent
<220> FEATURE:
<221> NAME/KEY: SITE
<222> LOCATION: (79)..(87)
<223> OTHER INFORMATION: This region may encompass 0-9 Gly residues,
      wherein some positions may be absent
<220> FEATURE:
<221> NAME/KEY: SITE
<222> LOCATION: (90)..(98)
<223> OTHER INFORMATION: This region may encompass 0-9 Gly residues,
      wherein some positions may be absent
<220> FEATURE:
<221> NAME/KEY: SITE
<222> LOCATION: (101)..(109)
<223> OTHER INFORMATION: This region may encompass 0-9 Gly residues,
      wherein some positions may be absent
<220> FEATURE:
<221> NAME/KEY: MOD_RES
```

```
<222> LOCATION: (111)..(115)
<223> OTHER INFORMATION: Arg, His, Asn, Gln, Ser, Thr, Tyr, Gly, Ala,
      Val, Leu, Trp, Met, Cys, Phe, Lys, Ile or absent
<220> FEATURE:
<221> NAME/KEY: MOD_RES
<222> LOCATION: (116)..(116)
<223> OTHER INFORMATION: Lys or Arg
<220> FEATURE:
<221> NAME/KEY: MOD_RES
<222> LOCATION: (117)..(121)
<223> OTHER INFORMATION: Arg, His, Asn, Gln, Ser, Thr, Tyr, Gly, Ala,
      Val, Leu, Trp, Met, Cys, Phe, Lys, Ile or absent
<220> FEATURE:
<221> NAME/KEY: SITE
<222> LOCATION: (123)..(131)
<223> OTHER INFORMATION: This region may encompass 0-9 Gly residues,
      wherein some positions may be absent
<220> FEATURE:
<221> NAME/KEY: SITE
<222> LOCATION: (133)..(231)
<223> OTHER INFORMATION: This region may encompass 0-9 "(Gly)n Ser"
      repeating units, wherein n = 1-10 and some positions may be absent
<220> FEATURE:
<221> NAME/KEY: SITE
<222> LOCATION: (134)..(142)
<223> OTHER INFORMATION: This region may encompass 0-9 Gly residues,
      wherein some positions may be absent
<220> FEATURE:
<221> NAME/KEY: SITE
<222> LOCATION: (145)..(153)
<223> OTHER INFORMATION: This region may encompass 0-9 Gly residues,
      wherein some positions may be absent
<220> FEATURE:
<221> NAME/KEY: SITE
<222> LOCATION: (156)..(164)
<223> OTHER INFORMATION: This region may encompass 0-9 Gly residues,
      wherein some positions may be absent
<220> FEATURE:
<221> NAME/KEY: SITE
<222> LOCATION: (167)..(175)
<223> OTHER INFORMATION: This region may encompass 0-9 Gly residues,
      wherein some positions may be absent
<220> FEATURE:
<221> NAME/KEY: SITE
<222> LOCATION: (178)..(186)
<223> OTHER INFORMATION: This region may encompass 0-9 Gly residues,
      wherein some positions may be absent
<220> FEATURE:
<221> NAME/KEY: SITE
<222> LOCATION: (189)..(197)
<223> OTHER INFORMATION: This region may encompass 0-9 Gly residues,
      wherein some positions may be absent
<220> FEATURE:
<221> NAME/KEY: SITE
<222> LOCATION: (200)..(208)
<223> OTHER INFORMATION: This region may encompass 0-9 Gly residues,
      wherein some positions may be absent
<220> FEATURE:
<221> NAME/KEY: SITE
<222> LOCATION: (211)..(219)
<223> OTHER INFORMATION: This region may encompass 0-9 Gly residues,
      wherein some positions may be absent
<220> FEATURE:
<221> NAME/KEY: SITE
<222> LOCATION: (222)..(230)
<223> OTHER INFORMATION: This region may encompass 0-9 Gly residues,
      wherein some positions may be absent
<220> FEATURE:
<221> NAME/KEY: SITE
<222> LOCATION: (232)..(2310)
<223> OTHER INFORMATION: This region may encompass 0-9 "(GaS)x-BJB'-
      (GaS)y" repeating units, wherein J is Lys or Arg, B is 0-5 amino
      acid residues selected from Arg, His, Asn, Gln, Ser, Thr, Tyr,
      Gly, Ala, Val, Leu, Trp, Met, Cys, Phe, Lys, or Ile, B' is 0-5
      amino
<220> FEATURE:
<221> NAME/KEY: SITE
<222> LOCATION: (232)..(2310)
<223> OTHER INFORMATION: Cont. from above: acid residues selected from
```

Arg, His, Asn, Gln, Ser, Thr, Tyr, Gly, Ala, Val, Leu, Trp, Met,
Cys, Phe, Lys, or Ile, a is 1-10, x is 1-10, y is 1-10, and
wherein some positions may be absent

<400> SEQUENCE: 85

```
Gly Gly Gly Gly Gly Gly Gly Gly Ser Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Gly Gly Gly Gly Gly Gly
        115                 120                 125

Gly Gly Gly Ser Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa
```

```
            385                 390                 395                 400
Xaa Xaa Xaa Xaa Xaa Xaa Xaa Xaa Xaa Xaa Xaa Xaa Xaa Xaa Xaa Xaa
                405                 410                 415
Xaa Xaa Xaa Xaa Xaa Xaa Xaa Xaa Xaa Xaa Xaa Xaa Xaa Xaa Xaa Xaa
                420                 425                 430
Xaa Xaa Xaa Xaa Xaa Xaa Xaa Xaa Xaa Xaa Xaa Xaa Xaa Xaa Xaa Xaa
                435                 440                 445
Xaa Xaa Xaa Xaa Xaa Xaa Xaa Xaa Xaa Xaa Xaa Xaa Xaa Xaa Xaa Xaa
            450                 455                 460
Xaa Xaa Xaa Xaa Xaa Xaa Xaa Xaa Xaa Xaa Xaa Xaa Xaa Xaa Xaa Xaa
465                 470                 475                 480
Xaa Xaa Xaa Xaa Xaa Xaa Xaa Xaa Xaa Xaa Xaa Xaa Xaa Xaa Xaa Xaa
                485                 490                 495
Xaa Xaa Xaa Xaa Xaa Xaa Xaa Xaa Xaa Xaa Xaa Xaa Xaa Xaa Xaa Xaa
                500                 505                 510
Xaa Xaa Xaa Xaa Xaa Xaa Xaa Xaa Xaa Xaa Xaa Xaa Xaa Xaa Xaa Xaa
                515                 520                 525
Xaa Xaa Xaa Xaa Xaa Xaa Xaa Xaa Xaa Xaa Xaa Xaa Xaa Xaa Xaa Xaa
            530                 535                 540
Xaa Xaa Xaa Xaa Xaa Xaa Xaa Xaa Xaa Xaa Xaa Xaa Xaa Xaa Xaa Xaa
545                 550                 555                 560
Xaa Xaa Xaa Xaa Xaa Xaa Xaa Xaa Xaa Xaa Xaa Xaa Xaa Xaa Xaa Xaa
                565                 570                 575
Xaa Xaa Xaa Xaa Xaa Xaa Xaa Xaa Xaa Xaa Xaa Xaa Xaa Xaa Xaa Xaa
                580                 585                 590
Xaa Xaa Xaa Xaa Xaa Xaa Xaa Xaa Xaa Xaa Xaa Xaa Xaa Xaa Xaa Xaa
                595                 600                 605
Xaa Xaa Xaa Xaa Xaa Xaa Xaa Xaa Xaa Xaa Xaa Xaa Xaa Xaa Xaa Xaa
            610                 615                 620
Xaa Xaa Xaa Xaa Xaa Xaa Xaa Xaa Xaa Xaa Xaa Xaa Xaa Xaa Xaa Xaa
625                 630                 635                 640
Xaa Xaa Xaa Xaa Xaa Xaa Xaa Xaa Xaa Xaa Xaa Xaa Xaa Xaa Xaa Xaa
                645                 650                 655
Xaa Xaa Xaa Xaa Xaa Xaa Xaa Xaa Xaa Xaa Xaa Xaa Xaa Xaa Xaa Xaa
                660                 665                 670
Xaa Xaa Xaa Xaa Xaa Xaa Xaa Xaa Xaa Xaa Xaa Xaa Xaa Xaa Xaa Xaa
                675                 680                 685
Xaa Xaa Xaa Xaa Xaa Xaa Xaa Xaa Xaa Xaa Xaa Xaa Xaa Xaa Xaa Xaa
            690                 695                 700
Xaa Xaa Xaa Xaa Xaa Xaa Xaa Xaa Xaa Xaa Xaa Xaa Xaa Xaa Xaa Xaa
705                 710                 715                 720
Xaa Xaa Xaa Xaa Xaa Xaa Xaa Xaa Xaa Xaa Xaa Xaa Xaa Xaa Xaa Xaa
                725                 730                 735
Xaa Xaa Xaa Xaa Xaa Xaa Xaa Xaa Xaa Xaa Xaa Xaa Xaa Xaa Xaa Xaa
            740                 745                 750
Xaa Xaa Xaa Xaa Xaa Xaa Xaa Xaa Xaa Xaa Xaa Xaa Xaa Xaa Xaa Xaa
                755                 760                 765
Xaa Xaa Xaa Xaa Xaa Xaa Xaa Xaa Xaa Xaa Xaa Xaa Xaa Xaa Xaa Xaa
            770                 775                 780
Xaa Xaa Xaa Xaa Xaa Xaa Xaa Xaa Xaa Xaa Xaa Xaa Xaa Xaa Xaa Xaa
785                 790                 795                 800
Xaa Xaa Xaa Xaa Xaa Xaa Xaa Xaa Xaa Xaa Xaa Xaa Xaa Xaa Xaa Xaa
                805                 810                 815
```

Xaa Xaa Xaa Xaa Xaa Xaa Xaa Xaa Xaa Xaa Xaa Xaa Xaa Xaa Xaa
        820                 825                 830

Xaa Xaa Xaa Xaa Xaa Xaa Xaa Xaa Xaa Xaa Xaa Xaa Xaa Xaa Xaa
        835                 840                 845

Xaa Xaa Xaa Xaa Xaa Xaa Xaa Xaa Xaa Xaa Xaa Xaa Xaa Xaa Xaa
        850                 855                 860

Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Xaa Xaa Xaa Xaa Xaa Xaa Xaa
        885                 890                 895

Xaa Xaa Xaa Xaa Xaa Xaa Xaa Xaa Xaa Xaa Xaa Xaa Xaa Xaa Xaa
        900                 905                 910

Xaa Xaa Xaa Xaa Xaa Xaa Xaa Xaa Xaa Xaa Xaa Xaa Xaa Xaa Xaa
        915                 920                 925

Xaa Xaa Xaa Xaa Xaa Xaa Xaa Xaa Xaa Xaa Xaa Xaa Xaa Xaa Xaa
        930                 935                 940

Xaa Xaa Xaa Xaa Xaa Xaa Xaa Xaa Xaa Xaa Xaa Xaa Xaa Xaa Xaa
945                 950                 955                 960

Xaa Xaa Xaa Xaa Xaa Xaa Xaa Xaa Xaa Xaa Xaa Xaa Xaa Xaa Xaa
        965                 970                 975

Xaa Xaa Xaa Xaa Xaa Xaa Xaa Xaa Xaa Xaa Xaa Xaa Xaa Xaa Xaa
        980                 985                 990

Xaa Xaa Xaa Xaa Xaa Xaa Xaa  Xaa Xaa Xaa Xaa Xaa  Xaa Xaa Xaa
        995                 1000                1005

Xaa Xaa  Xaa Xaa Xaa Xaa Xaa  Xaa Xaa Xaa Xaa Xaa  Xaa Xaa Xaa
    1010                1015                1020

Xaa Xaa  Xaa Xaa Xaa Xaa Xaa  Xaa Xaa Xaa Xaa Xaa  Xaa Xaa Xaa
    1025                1030                1035

Xaa Xaa  Xaa Xaa Xaa Xaa Xaa  Xaa Xaa Xaa Xaa Xaa  Xaa Xaa Xaa
    1040                1045                1050

Xaa Xaa  Xaa Xaa Xaa Xaa Xaa  Xaa Xaa Xaa Xaa Xaa  Xaa Xaa Xaa
    1055                1060                1065

Xaa Xaa  Xaa Xaa Xaa Xaa Xaa  Xaa Xaa Xaa Xaa Xaa  Xaa Xaa Xaa
    1070                1075                1080

Xaa Xaa  Xaa Xaa Xaa Xaa Xaa  Xaa Xaa Xaa Xaa Xaa  Xaa Xaa Xaa
    1085                1090                1095

Xaa Xaa  Xaa Xaa Xaa Xaa Xaa  Xaa Xaa Xaa Xaa Xaa  Xaa Xaa Xaa
    1100                1105                1110

Xaa Xaa  Xaa Xaa Xaa Xaa Xaa  Xaa Xaa Xaa Xaa Xaa  Xaa Xaa Xaa
    1115                1120                1125

Xaa Xaa  Xaa Xaa Xaa Xaa Xaa  Xaa Xaa Xaa Xaa Xaa  Xaa Xaa Xaa
    1130                1135                1140

Xaa Xaa  Xaa Xaa Xaa Xaa Xaa  Xaa Xaa Xaa Xaa Xaa  Xaa Xaa Xaa
    1145                1150                1155

Xaa Xaa  Xaa Xaa Xaa Xaa Xaa  Xaa Xaa Xaa Xaa Xaa  Xaa Xaa Xaa
    1160                1165                1170

Xaa Xaa  Xaa Xaa Xaa Xaa Xaa  Xaa Xaa Xaa Xaa Xaa  Xaa Xaa Xaa
    1175                1180                1185

Xaa Xaa  Xaa Xaa Xaa Xaa Xaa  Xaa Xaa Xaa Xaa Xaa  Xaa Xaa Xaa
    1190                1195                1200

Xaa Xaa  Xaa Xaa Xaa Xaa Xaa  Xaa Xaa Xaa Xaa Xaa  Xaa Xaa Xaa
    1205                1210                1215

-continued

Xaa Xaa Xaa Xaa Xaa Xaa Xaa Xaa Xaa Xaa Xaa Xaa Xaa Xaa Xaa
    1220                1225                1230

Xaa Xaa Xaa Xaa Xaa Xaa Xaa Xaa Xaa Xaa Xaa Xaa Xaa Xaa Xaa
    1235                1240                1245

Xaa Xaa Xaa Xaa Xaa Xaa Xaa Xaa Xaa Xaa Xaa Xaa Xaa Xaa Xaa
    1250                1255                1260

Xaa Xaa Xaa Xaa Xaa Xaa Xaa Xaa Xaa Xaa Xaa Xaa Xaa Xaa Xaa
    1265                1270                1275

Xaa Xaa Xaa Xaa Xaa Xaa Xaa Xaa Xaa Xaa Xaa Xaa Xaa Xaa Xaa
    1280                1285                1290

Xaa Xaa Xaa Xaa Xaa Xaa Xaa Xaa Xaa Xaa Xaa Xaa Xaa Xaa Xaa
    1295                1300                1305

Xaa Xaa Xaa Xaa Xaa Xaa Xaa Xaa Xaa Xaa Xaa Xaa Xaa Xaa Xaa
    1310                1315                1320

Xaa Xaa Xaa Xaa Xaa Xaa Xaa Xaa Xaa Xaa Xaa Xaa Xaa Xaa Xaa
    1325                1330                1335

Xaa Xaa Xaa Xaa Xaa Xaa Xaa Xaa Xaa Xaa Xaa Xaa Xaa Xaa Xaa
    1340                1345                1350

Xaa Xaa Xaa Xaa Xaa Xaa Xaa Xaa Xaa Xaa Xaa Xaa Xaa Xaa Xaa
    1355                1360                1365

Xaa Xaa Xaa Xaa Xaa Xaa Xaa Xaa Xaa Xaa Xaa Xaa Xaa Xaa Xaa
    1370                1375                1380

Xaa Xaa Xaa Xaa Xaa Xaa Xaa Xaa Xaa Xaa Xaa Xaa Xaa Xaa Xaa
    1385                1390                1395

Xaa Xaa Xaa Xaa Xaa Xaa Xaa Xaa Xaa Xaa Xaa Xaa Xaa Xaa Xaa
    1400                1405                1410

Xaa Xaa Xaa Xaa Xaa Xaa Xaa Xaa Xaa Xaa Xaa Xaa Xaa Xaa Xaa
    1415                1420                1425

Xaa Xaa Xaa Xaa Xaa Xaa Xaa Xaa Xaa Xaa Xaa Xaa Xaa Xaa Xaa
    1430                1435                1440

Xaa Xaa Xaa Xaa Xaa Xaa Xaa Xaa Xaa Xaa Xaa Xaa Xaa Xaa Xaa
    1445                1450                1455

Xaa Xaa Xaa Xaa Xaa Xaa Xaa Xaa Xaa Xaa Xaa Xaa Xaa Xaa Xaa
    1460                1465                1470

Xaa Xaa Xaa Xaa Xaa Xaa Xaa Xaa Xaa Xaa Xaa Xaa Xaa Xaa Xaa
    1475                1480                1485

Xaa Xaa Xaa Xaa Xaa Xaa Xaa Xaa Xaa Xaa Xaa Xaa Xaa Xaa Xaa
    1490                1495                1500

Xaa Xaa Xaa Xaa Xaa Xaa Xaa Xaa Xaa Xaa Xaa Xaa Xaa Xaa Xaa
    1505                1510                1515

Xaa Xaa Xaa Xaa Xaa Xaa Xaa Xaa Xaa Xaa Xaa Xaa Xaa Xaa Xaa
    1520                1525                1530

Xaa Xaa Xaa Xaa Xaa Xaa Xaa Xaa Xaa Xaa Xaa Xaa Xaa Xaa Xaa
    1535                1540                1545

Xaa Xaa Xaa Xaa Xaa Xaa Xaa Xaa Xaa Xaa Xaa Xaa Xaa Xaa Xaa
    1550                1555                1560

Xaa Xaa Xaa Xaa Xaa Xaa Xaa Xaa Xaa Xaa Xaa Xaa Xaa Xaa Xaa
    1565                1570                1575

Xaa Xaa Xaa Xaa Xaa Xaa Xaa Xaa Xaa Xaa Xaa Xaa Xaa Xaa Xaa
    1580                1585                1590

Xaa Xaa Xaa Xaa Xaa Xaa Xaa Xaa Xaa Xaa Xaa Xaa Xaa Xaa Xaa
    1595                1600                1605

Xaa Xaa Xaa Xaa Xaa Xaa Xaa Xaa Xaa Xaa Xaa Xaa Xaa Xaa Xaa

```
            1610                1615                1620

Xaa Xaa Xaa Xaa Xaa Xaa Xaa  Xaa Xaa Xaa Xaa Xaa  Xaa Xaa Xaa
            1625                1630                1635

Xaa Xaa Xaa Xaa Xaa Xaa Xaa  Xaa Xaa Xaa Xaa Xaa  Xaa Xaa Xaa
            1640                1645                1650

Xaa Xaa Xaa Xaa Xaa Xaa Xaa  Xaa Xaa Xaa Xaa Xaa  Xaa Xaa Xaa
            1655                1660                1665

Xaa Xaa Xaa Xaa Xaa Xaa Xaa  Xaa Xaa Xaa Xaa Xaa  Xaa Xaa Xaa
            1670                1675                1680

Xaa Xaa Xaa Xaa Xaa Xaa Xaa  Xaa Xaa Xaa Xaa Xaa  Xaa Xaa Xaa
            1685                1690                1695

Xaa Xaa Xaa Xaa Xaa Xaa Xaa  Xaa Xaa Xaa Xaa Xaa  Xaa Xaa Xaa
            1700                1705                1710

Xaa Xaa Xaa Xaa Xaa Xaa Xaa  Xaa Xaa Xaa Xaa Xaa  Xaa Xaa Xaa
            1715                1720                1725

Xaa Xaa Xaa Xaa Xaa Xaa Xaa  Xaa Xaa Xaa Xaa Xaa  Xaa Xaa Xaa
            1730                1735                1740

Xaa Xaa Xaa Xaa Xaa Xaa Xaa  Xaa Xaa Xaa Xaa Xaa  Xaa Xaa Xaa
            1745                1750                1755

Xaa Xaa Xaa Xaa Xaa Xaa Xaa  Xaa Xaa Xaa Xaa Xaa  Xaa Xaa Xaa
            1760                1765                1770

Xaa Xaa Xaa Xaa Xaa Xaa Xaa  Xaa Xaa Xaa Xaa Xaa  Xaa Xaa Xaa
            1775                1780                1785

Xaa Xaa Xaa Xaa Xaa Xaa Xaa  Xaa Xaa Xaa Xaa Xaa  Xaa Xaa Xaa
            1790                1795                1800

Xaa Xaa Xaa Xaa Xaa Xaa Xaa  Xaa Xaa Xaa Xaa Xaa  Xaa Xaa Xaa
            1805                1810                1815

Xaa Xaa Xaa Xaa Xaa Xaa Xaa  Xaa Xaa Xaa Xaa Xaa  Xaa Xaa Xaa
            1820                1825                1830

Xaa Xaa Xaa Xaa Xaa Xaa Xaa  Xaa Xaa Xaa Xaa Xaa  Xaa Xaa Xaa
            1835                1840                1845

Xaa Xaa Xaa Xaa Xaa Xaa Xaa  Xaa Xaa Xaa Xaa Xaa  Xaa Xaa Xaa
            1850                1855                1860

Xaa Xaa Xaa Xaa Xaa Xaa Xaa  Xaa Xaa Xaa Xaa Xaa  Xaa Xaa Xaa
            1865                1870                1875

Xaa Xaa Xaa Xaa Xaa Xaa Xaa  Xaa Xaa Xaa Xaa Xaa  Xaa Xaa Xaa
            1880                1885                1890

Xaa Xaa Xaa Xaa Xaa Xaa Xaa  Xaa Xaa Xaa Xaa Xaa  Xaa Xaa Xaa
            1895                1900                1905

Xaa Xaa Xaa Xaa Xaa Xaa Xaa  Xaa Xaa Xaa Xaa Xaa  Xaa Xaa Xaa
            1910                1915                1920

Xaa Xaa Xaa Xaa Xaa Xaa Xaa  Xaa Xaa Xaa Xaa Xaa  Xaa Xaa Xaa
            1925                1930                1935

Xaa Xaa Xaa Xaa Xaa Xaa Xaa  Xaa Xaa Xaa Xaa Xaa  Xaa Xaa Xaa
            1940                1945                1950

Xaa Xaa Xaa Xaa Xaa Xaa Xaa  Xaa Xaa Xaa Xaa Xaa  Xaa Xaa Xaa
            1955                1960                1965

Xaa Xaa Xaa Xaa Xaa Xaa Xaa  Xaa Xaa Xaa Xaa Xaa  Xaa Xaa Xaa
            1970                1975                1980

Xaa Xaa Xaa Xaa Xaa Xaa Xaa  Xaa Xaa Xaa Xaa Xaa  Xaa Xaa Xaa
            1985                1990                1995

Xaa Xaa Xaa Xaa Xaa Xaa Xaa  Xaa Xaa Xaa Xaa Xaa  Xaa Xaa Xaa
            2000                2005                2010
```

Xaa Xaa Xaa Xaa Xaa Xaa Xaa  Xaa Xaa Xaa Xaa Xaa  Xaa Xaa Xaa
        2015                2020                2025

Xaa Xaa Xaa Xaa Xaa Xaa Xaa  Xaa Xaa Xaa Xaa Xaa  Xaa Xaa Xaa
        2030                2035                2040

Xaa Xaa Xaa Xaa Xaa Xaa Xaa  Xaa Xaa Xaa Xaa Xaa  Xaa Xaa Xaa
        2045                2050                2055

Xaa Xaa Xaa Xaa Xaa Xaa Xaa  Xaa Xaa Xaa Xaa Xaa  Xaa Xaa Xaa
        2060                2065                2070

Xaa Xaa Xaa Xaa Xaa Xaa Xaa  Xaa Xaa Xaa Xaa Xaa  Xaa Xaa Xaa
        2075                2080                2085

Xaa Xaa Xaa Xaa Xaa Xaa Xaa  Xaa Xaa Xaa Xaa Xaa  Xaa Xaa Xaa
        2090                2095                2100

Xaa Xaa Xaa Xaa Xaa Xaa Xaa  Xaa Xaa Xaa Xaa Xaa  Xaa Xaa Xaa
        2105                2110                2115

Xaa Xaa Xaa Xaa Xaa Xaa Xaa  Xaa Xaa Xaa Xaa Xaa  Xaa Xaa Xaa
        2120                2125                2130

Xaa Xaa Xaa Xaa Xaa Xaa Xaa  Xaa Xaa Xaa Xaa Xaa  Xaa Xaa Xaa
        2135                2140                2145

Xaa Xaa Xaa Xaa Xaa Xaa Xaa  Xaa Xaa Xaa Xaa Xaa  Xaa Xaa Xaa
        2150                2155                2160

Xaa Xaa Xaa Xaa Xaa Xaa Xaa  Xaa Xaa Xaa Xaa Xaa  Xaa Xaa Xaa
        2165                2170                2175

Xaa Xaa Xaa Xaa Xaa Xaa Xaa  Xaa Xaa Xaa Xaa Xaa  Xaa Xaa Xaa
        2180                2185                2190

Xaa Xaa Xaa Xaa Xaa Xaa Xaa  Xaa Xaa Xaa Xaa Xaa  Xaa Xaa Xaa
        2195                2200                2205

Xaa Xaa Xaa Xaa Xaa Xaa Xaa  Xaa Xaa Xaa Xaa Xaa  Xaa Xaa Xaa
        2210                2215                2220

Xaa Xaa Xaa Xaa Xaa Xaa Xaa  Xaa Xaa Xaa Xaa Xaa  Xaa Xaa Xaa
        2225                2230                2235

Xaa Xaa Xaa Xaa Xaa Xaa Xaa  Xaa Xaa Xaa Xaa Xaa  Xaa Xaa Xaa
        2240                2245                2250

Xaa Xaa Xaa Xaa Xaa Xaa Xaa  Xaa Xaa Xaa Xaa Xaa  Xaa Xaa Xaa
        2255                2260                2265

Xaa Xaa Xaa Xaa Xaa Xaa Xaa  Xaa Xaa Xaa Xaa Xaa  Xaa Xaa Xaa
        2270                2275                2280

Xaa Xaa Xaa Xaa Xaa Xaa Xaa  Xaa Xaa Xaa Xaa Xaa  Xaa Xaa Xaa
        2285                2290                2295

Xaa Xaa Xaa Xaa Xaa Xaa Xaa  Xaa Xaa Xaa Xaa Xaa
        2300                2305                2310

<210> SEQ ID NO 86
<211> LENGTH: 51
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (6)..(6)
<223> OTHER INFORMATION: Gly or absent
<220> FEATURE:
<221> NAME/KEY: SITE
<222> LOCATION: (6)..(25)
<223> OTHER INFORMATION: This region may encompass 0-4 "Gly Gly Gly Gly
      Ser" repeating units wherein some positions may be absent
<220> FEATURE:
<221> NAME/KEY: MOD_RES

```
<222> LOCATION: (7)..(7)
<223> OTHER INFORMATION: Gly or absent
<220> FEATURE:
<221> NAME/KEY: MOD_RES
<222> LOCATION: (8)..(8)
<223> OTHER INFORMATION: Gly or absent
<220> FEATURE:
<221> NAME/KEY: MOD_RES
<222> LOCATION: (9)..(9)
<223> OTHER INFORMATION: Gly or absent
<220> FEATURE:
<221> NAME/KEY: MOD_RES
<222> LOCATION: (10)..(10)
<223> OTHER INFORMATION: Ser or absent
<220> FEATURE:
<221> NAME/KEY: MOD_RES
<222> LOCATION: (11)..(11)
<223> OTHER INFORMATION: Gly or absent
<220> FEATURE:
<221> NAME/KEY: MOD_RES
<222> LOCATION: (12)..(12)
<223> OTHER INFORMATION: Gly or absent
<220> FEATURE:
<221> NAME/KEY: MOD_RES
<222> LOCATION: (13)..(13)
<223> OTHER INFORMATION: Gly or absent
<220> FEATURE:
<221> NAME/KEY: MOD_RES
<222> LOCATION: (14)..(14)
<223> OTHER INFORMATION: Gly or absent
<220> FEATURE:
<221> NAME/KEY: MOD_RES
<222> LOCATION: (15)..(15)
<223> OTHER INFORMATION: Ser or absent
<220> FEATURE:
<221> NAME/KEY: MOD_RES
<222> LOCATION: (16)..(16)
<223> OTHER INFORMATION: Gly or absent
<220> FEATURE:
<221> NAME/KEY: MOD_RES
<222> LOCATION: (17)..(17)
<223> OTHER INFORMATION: Gly or absent
<220> FEATURE:
<221> NAME/KEY: MOD_RES
<222> LOCATION: (18)..(18)
<223> OTHER INFORMATION: Gly or absent
<220> FEATURE:
<221> NAME/KEY: MOD_RES
<222> LOCATION: (19)..(19)
<223> OTHER INFORMATION: Gly or absent
<220> FEATURE:
<221> NAME/KEY: MOD_RES
<222> LOCATION: (20)..(20)
<223> OTHER INFORMATION: Ser or absent
<220> FEATURE:
<221> NAME/KEY: MOD_RES
<222> LOCATION: (21)..(21)
<223> OTHER INFORMATION: Gly or absent
<220> FEATURE:
<221> NAME/KEY: MOD_RES
<222> LOCATION: (22)..(22)
<223> OTHER INFORMATION: Gly or absent
<220> FEATURE:
<221> NAME/KEY: MOD_RES
<222> LOCATION: (23)..(23)
<223> OTHER INFORMATION: Gly or absent
<220> FEATURE:
<221> NAME/KEY: MOD_RES
<222> LOCATION: (24)..(24)
<223> OTHER INFORMATION: Gly or absent
<220> FEATURE:
<221> NAME/KEY: MOD_RES
<222> LOCATION: (25)..(25)
<223> OTHER INFORMATION: Ser or absent
<220> FEATURE:
<221> NAME/KEY: MOD_RES
<222> LOCATION: (32)..(32)
<223> OTHER INFORMATION: Gly or absent
<220> FEATURE:
```

-continued

```
<221> NAME/KEY: SITE
<222> LOCATION: (32)..(51)
<223> OTHER INFORMATION: This region may encompass 0-4 "Gly Gly Gly Gly
      Ser" repeating units wherein some positions may be absent
<220> FEATURE:
<221> NAME/KEY: MOD_RES
<222> LOCATION: (33)..(33)
<223> OTHER INFORMATION: Gly or absent
<220> FEATURE:
<221> NAME/KEY: MOD_RES
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Gly or absent
<220> FEATURE:
<221> NAME/KEY: MOD_RES
<222> LOCATION: (36)..(36)
<223> OTHER INFORMATION: Ser or absent
<220> FEATURE:
<221> NAME/KEY: MOD_RES
<222> LOCATION: (37)..(37)
<223> OTHER INFORMATION: Gly or absent
<220> FEATURE:
<221> NAME/KEY: MOD_RES
<222> LOCATION: (38)..(38)
<223> OTHER INFORMATION: Gly or absent
<220> FEATURE:
<221> NAME/KEY: MOD_RES
<222> LOCATION: (39)..(39)
<223> OTHER INFORMATION: Gly or absent
<220> FEATURE:
<221> NAME/KEY: MOD_RES
<222> LOCATION: (40)..(40)
<223> OTHER INFORMATION: Gly or absent
<220> FEATURE:
<221> NAME/KEY: MOD_RES
<222> LOCATION: (41)..(41)
<223> OTHER INFORMATION: Ser or absent
<220> FEATURE:
<221> NAME/KEY: MOD_RES
<222> LOCATION: (42)..(42)
<223> OTHER INFORMATION: Gly or absent
<220> FEATURE:
<221> NAME/KEY: MOD_RES
<222> LOCATION: (43)..(43)
<223> OTHER INFORMATION: Gly or absent
<220> FEATURE:
<221> NAME/KEY: MOD_RES
<222> LOCATION: (44)..(44)
<223> OTHER INFORMATION: Gly or absent
<220> FEATURE:
<221> NAME/KEY: MOD_RES
<222> LOCATION: (45)..(45)
<223> OTHER INFORMATION: Gly or absent
<220> FEATURE:
<221> NAME/KEY: MOD_RES
<222> LOCATION: (46)..(46)
<223> OTHER INFORMATION: Ser or absent
<220> FEATURE:
<221> NAME/KEY: MOD_RES
<222> LOCATION: (47)..(47)
<223> OTHER INFORMATION: Gly or absent
<220> FEATURE:
<221> NAME/KEY: MOD_RES
<222> LOCATION: (48)..(48)
<223> OTHER INFORMATION: Gly or absent
<220> FEATURE:
<221> NAME/KEY: MOD_RES
<222> LOCATION: (49)..(49)
<223> OTHER INFORMATION: Gly or absent
<220> FEATURE:
<221> NAME/KEY: MOD_RES
<222> LOCATION: (50)..(50)
<223> OTHER INFORMATION: Gly or absent
<220> FEATURE:
<221> NAME/KEY: MOD_RES
<222> LOCATION: (51)..(51)
```

```
<223> OTHER INFORMATION: Ser or absent

<400> SEQUENCE: 86

Gly Gly Gly Gly Ser Xaa Xaa Xaa Xaa Xaa Xaa Xaa Xaa Xaa Xaa
1               5                   10                  15

Xaa Xaa Xaa Xaa Xaa Xaa Xaa Xaa Xaa Lys Gly Gly Gly Gly Ser Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa
    50

<210> SEQ ID NO 87
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 87

Gly Gly Gly Gly Ser Gly Gly Gly Ser Lys Gly Gly Gly Gly Ser
1               5                   10                  15

Gly Gly Gly Gly Ser
            20

<210> SEQ ID NO 88
<211> LENGTH: 50
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (6)..(6)
<223> OTHER INFORMATION: Gly or absent
<220> FEATURE:
<221> NAME/KEY: SITE
<222> LOCATION: (6)..(50)
<223> OTHER INFORMATION: This region may encompass 0-9 "Gly Gly Gly Gly
      Ser" repeating units wherein some positions may be absent
<220> FEATURE:
<221> NAME/KEY: MOD_RES
<222> LOCATION: (7)..(7)
<223> OTHER INFORMATION: Gly or absent
<220> FEATURE:
<221> NAME/KEY: MOD_RES
<222> LOCATION: (8)..(8)
<223> OTHER INFORMATION: Gly or absent
<220> FEATURE:
<221> NAME/KEY: MOD_RES
<222> LOCATION: (9)..(9)
<223> OTHER INFORMATION: Gly or absent
<220> FEATURE:
<221> NAME/KEY: MOD_RES
<222> LOCATION: (10)..(10)
<223> OTHER INFORMATION: Ser or absent
<220> FEATURE:
<221> NAME/KEY: MOD_RES
<222> LOCATION: (11)..(11)
<223> OTHER INFORMATION: Gly or absent
<220> FEATURE:
<221> NAME/KEY: MOD_RES
<222> LOCATION: (12)..(12)
<223> OTHER INFORMATION: Gly or absent
<220> FEATURE:
<221> NAME/KEY: MOD_RES
<222> LOCATION: (13)..(13)
<223> OTHER INFORMATION: Gly or absent
<220> FEATURE:
<221> NAME/KEY: MOD_RES
<222> LOCATION: (14)..(14)
```

```
<223> OTHER INFORMATION: Gly or absent
<220> FEATURE:
<221> NAME/KEY: MOD_RES
<222> LOCATION: (15)..(15)
<223> OTHER INFORMATION: Ser or absent
<220> FEATURE:
<221> NAME/KEY: MOD_RES
<222> LOCATION: (16)..(16)
<223> OTHER INFORMATION: Gly or absent
<220> FEATURE:
<221> NAME/KEY: MOD_RES
<222> LOCATION: (17)..(17)
<223> OTHER INFORMATION: Gly or absent
<220> FEATURE:
<221> NAME/KEY: MOD_RES
<222> LOCATION: (18)..(18)
<223> OTHER INFORMATION: Gly or absent
<220> FEATURE:
<221> NAME/KEY: MOD_RES
<222> LOCATION: (19)..(19)
<223> OTHER INFORMATION: Gly or absent
<220> FEATURE:
<221> NAME/KEY: MOD_RES
<222> LOCATION: (20)..(20)
<223> OTHER INFORMATION: Ser or absent
<220> FEATURE:
<221> NAME/KEY: MOD_RES
<222> LOCATION: (21)..(21)
<223> OTHER INFORMATION: Gly or absent
<220> FEATURE:
<221> NAME/KEY: MOD_RES
<222> LOCATION: (22)..(22)
<223> OTHER INFORMATION: Gly or absent
<220> FEATURE:
<221> NAME/KEY: MOD_RES
<222> LOCATION: (23)..(23)
<223> OTHER INFORMATION: Gly or absent
<220> FEATURE:
<221> NAME/KEY: MOD_RES
<222> LOCATION: (24)..(24)
<223> OTHER INFORMATION: Gly or absent
<220> FEATURE:
<221> NAME/KEY: MOD_RES
<222> LOCATION: (25)..(25)
<223> OTHER INFORMATION: Ser or absent
<220> FEATURE:
<221> NAME/KEY: MOD_RES
<222> LOCATION: (26)..(26)
<223> OTHER INFORMATION: Gly or absent
<220> FEATURE:
<221> NAME/KEY: MOD_RES
<222> LOCATION: (27)..(27)
<223> OTHER INFORMATION: Gly or absent
<220> FEATURE:
<221> NAME/KEY: MOD_RES
<222> LOCATION: (28)..(28)
<223> OTHER INFORMATION: Gly or absent
<220> FEATURE:
<221> NAME/KEY: MOD_RES
<222> LOCATION: (29)..(29)
<223> OTHER INFORMATION: Gly or absent
<220> FEATURE:
<221> NAME/KEY: MOD_RES
<222> LOCATION: (30)..(30)
<223> OTHER INFORMATION: Ser or absent
<220> FEATURE:
<221> NAME/KEY: MOD_RES
<222> LOCATION: (31)..(31)
<223> OTHER INFORMATION: Gly or absent
<220> FEATURE:
<221> NAME/KEY: MOD_RES
<222> LOCATION: (32)..(32)
<223> OTHER INFORMATION: Gly or absent
<220> FEATURE:
<221> NAME/KEY: MOD_RES
<222> LOCATION: (33)..(33)
<223> OTHER INFORMATION: Gly or absent
<220> FEATURE:
<221> NAME/KEY: MOD_RES
```

```
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Ser or absent
<220> FEATURE:
<221> NAME/KEY: MOD_RES
<222> LOCATION: (36)..(36)
<223> OTHER INFORMATION: Gly or absent
<220> FEATURE:
<221> NAME/KEY: MOD_RES
<222> LOCATION: (37)..(37)
<223> OTHER INFORMATION: Gly or absent
<220> FEATURE:
<221> NAME/KEY: MOD_RES
<222> LOCATION: (38)..(38)
<223> OTHER INFORMATION: Gly or absent
<220> FEATURE:
<221> NAME/KEY: MOD_RES
<222> LOCATION: (39)..(39)
<223> OTHER INFORMATION: Gly or absent
<220> FEATURE:
<221> NAME/KEY: MOD_RES
<222> LOCATION: (40)..(40)
<223> OTHER INFORMATION: Ser or absent
<220> FEATURE:
<221> NAME/KEY: MOD_RES
<222> LOCATION: (41)..(41)
<223> OTHER INFORMATION: Gly or absent
<220> FEATURE:
<221> NAME/KEY: MOD_RES
<222> LOCATION: (42)..(42)
<223> OTHER INFORMATION: Gly or absent
<220> FEATURE:
<221> NAME/KEY: MOD_RES
<222> LOCATION: (43)..(43)
<223> OTHER INFORMATION: Gly or absent
<220> FEATURE:
<221> NAME/KEY: MOD_RES
<222> LOCATION: (44)..(44)
<223> OTHER INFORMATION: Gly or absent
<220> FEATURE:
<221> NAME/KEY: MOD_RES
<222> LOCATION: (45)..(45)
<223> OTHER INFORMATION: Ser or absent
<220> FEATURE:
<221> NAME/KEY: MOD_RES
<222> LOCATION: (46)..(46)
<223> OTHER INFORMATION: Gly or absent
<220> FEATURE:
<221> NAME/KEY: MOD_RES
<222> LOCATION: (47)..(47)
<223> OTHER INFORMATION: Gly or absent
<220> FEATURE:
<221> NAME/KEY: MOD_RES
<222> LOCATION: (48)..(48)
<223> OTHER INFORMATION: Gly or absent
<220> FEATURE:
<221> NAME/KEY: MOD_RES
<222> LOCATION: (49)..(49)
<223> OTHER INFORMATION: Gly or absent
<220> FEATURE:
<221> NAME/KEY: MOD_RES
<222> LOCATION: (50)..(50)
<223> OTHER INFORMATION: Ser or absent

<400> SEQUENCE: 88

Gly Gly Gly Gly Ser Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa
```

```
<210> SEQ ID NO 89
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 89

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

VHH IMMUNOGLOBULIN CHAIN VARIABLE DOMAIN THAT BINDS TO IL-7R AND METHODS OF USE THEREOF FOR TREATING AUTOIMMUNE AND/OR INFLAMMATORY DISEASES

CROSS-REFERENCE TO RELATED APPLICATIONS

This application is a continuation of U.S. application Ser. No. 17/620,030, filed on Dec. 16, 2021, which is the U.S. National Stage Entry of International Application No. PCT/GB2020/051496, filed internationally on Jun. 19, 2020, which claims the benefit of European Application No. 19181868.1, filed on Jun. 21, 2019, all of which are hereby incorporated by reference in their entireties.

SEQUENCE LISTING

The content of the ASCII text file of the sequence listing named "Sorriso_60790-710_301_Sequence_Listing-FINAL-06-15-2022.txt" which is 115,825 bytes in size was created on Jun. 15, 2022 and electronically submitted via EFS-Web on Jun. 15, 2022, is incorporated herein by reference in its entirety.

FIELD OF THE INVENTION

The present invention relates to polypeptides capable of inhibiting IL-7 and/or L-TSLP binding to IL-7R, as well as to constructs and pharmaceutical compositions comprising these polypeptides. The present invention also relates to nucleic acids encoding such polypeptides, to methods for preparing such polypeptides, to cDNA and vectors comprising nucleic acids encoding such polypeptides, to host cells expressing or capable of expressing such polypeptides and to uses of such polypeptides.

BACKGROUND OF THE INVENTION

Autoimmune Diseases of the Gastrointestinal Tract

Autoimmune diseases of the gastrointestinal tract include Inflammatory Bowel Disease such as Crohn's Disease (CD), and other autoimmune diseases such as eosinophilic esophagitis (EoE). Crohn's disease, also known as Crohn syndrome and regional enteritis causes a wide variety of symptoms. It primarily causes abdominal pain, diarrhea, vomiting and/or weight loss but may also cause complications outside the gastrointestinal tract (GIT) such as anaemia, skin rashes, arthritis, inflammation of the eye, tiredness, and lack of concentration (Baumgart et al 2012). Crohn's disease is a presently incurable life-long gastrointestinal disease that is difficult to control with conventional therapies. EoE is a chronic disease that is defined by a significant pathological eosinophil infiltration limited to the oesophagus that causes oesophageal dysfunction and, if left untreated, fibrosis. Oesophageal fibrosis and oesophageal strictures are known complications of EoE.

Antibody-based therapeutics have significant potential as effective treatments for autoimmune disease such as IBD and EoE because they have high specificity for their target and a low inherent toxicity. Three anti-TNF-alpha antibodies infliximab (trade name Remicade), adalimumab (trade name Humira) and certolizumab (or 'certolizumab pegol', trade name Cimzia) are used clinically for the treatment of Crohn's disease; however these antibodies are generally considered to be unsuitable for administration as oral therapeutics due to their inherent instability and susceptibility to proteolytic degradation by the digestive system, inflammatory proteases present at the sites of pathology in the intestinal tract, and intestinal microflora. These agents therefore have to be administered by intravenous infusion or subcutaneous injection which requires specialist training in order to use a hypodermic syringe or needle correctly and safely. These agents also require sterile equipment, a liquid formulation of the therapeutic polypeptide, vial packing of said polypeptide in a sterile and stable form and a suitable site on the subject for entry of the needle. Subjects commonly experience psychological stress before receiving an injection and pain while receiving an injection. Long term treatment with these systemic anti-TNF-alpha antibodies carries increased risks of serious infection and cancer. Together with the high costs of production, these factors currently restrict use of these agents to patients with more severe disease.

Several small molecule anti-inflammatory and immunosuppressive drugs are also currently in clinical development for Crohn's disease (Danese 2012, Shealy et al 2010 and Vetter & Neurath 2017). Although these drugs are orally administered, many will be absorbed systemically after administration and may therefore have systemic immunosuppressive actions that are unrelated to actions against the gastrointestinal tract lesions. Furthermore, as small molecules lack the specificity of antibodies the risk of significant off target side-effects remains high.

The ability to deliver an oral therapeutic agent with high selectivity for a target associated with an autoimmune disease of the gastrointestinal tract, but with exposure and activity limited to the gastrointestinal tract, may offer efficacy similar to injectable antibodies, combined with significant improvements in safety due to reduced systemic exposure.

Interleukin-7 (IL-7) and Interleukin-7 receptor (IL-7R)

Interleukin-7 (IL-7) is a member of the family of cytokines that includes IL-2, IL-4, IL-7, IL-15 and IL-21. IL-7 is produced constitutively by non-haematopoietic stromal and epithelial cells in lymphoid organs, intestine, skin and liver and is essential for the development of T-lymphocytes in the thymus and for the survival and homeostatic regulation of peripheral T cells (Fry and Mackall, 2002; Fry and Mackall 2005). In the intestinal mucosa IL-7 also regulates phenotypically and functionally distinct populations of innate lymphoid cells that are important for the initial priming of immune responses to pathogenic microbial challenges as well as CD4+ lymphoid tissue inducer (LTi) cells, which have the capacity to promote lymphoid tissue organogenesis and some dendritic cell populations (Goldberg et al 2015; Peters et al 2015). Furthermore, IL-7 induces proliferation of naive and memory T cells and enhances effector T cell responses, preferentially T helper 1 (Th1) and Th17 responses (Dooms, 2013). The functional effects of IL-7 on T cells makes IL-7 a critical enhancer of protective immunity, as well as of autoimmunity and inflammation.

The effects of IL-7 on different target cells are mediated through the IL-7R, a heterodimeric complex that includes the IL-7Rα subunit (CD127) and the common cytokine receptor gamma chain (γc) (CD132). Full-length human IL-7Rα consists of a 219-residue extracellular domain, a 25-residue transmembrane domain, and a 195-residue intracellular domain. IL-7 induced receptor activation is thought to involve an initial IL-7 interaction with the IL-7Rα to form a complex, which subsequently recruits γc, to form an activated receptor signalling complex. The association of the two receptor subunits by IL-7 activates intracellular phosphorylation events through the JAK/Stat, PI3/Akt, and SRC signalling cascades (Walsh, 2012).

The IL-7Rα is not only available in the cell-membrane-bound format, but also as a soluble form (sIL-7Rα). The sIL-7R is generated by shedding of membrane-bound receptors and is also produced by alternative splicing (of IL-7Rα exon 6) leading to a protein lacking the transmembrane domain; the sIL-7Rα present in human plasma is primarily derived from alternative splicing (Rose et al 2009). Four common haplotypes of the IL-7Rα gene have been identified (Teutsch et al 2003). Two haplotypes have been associated with altered expression and production of soluble forms of the receptor and susceptibility to autoimmune diseases that include multiple sclerosis and type 1 diabetes (Hafler et al 2007).

In addition to the roles played by the IL-7/IL-7Rα in human T cell development and homeostasis, preclinical studies have demonstrated the involvement of the IL-7/IL-7Rα pathway in animal models of different autoimmune and inflammatory diseases. These studies have identified additional IL-7-dependent mechanisms associated with disease pathology and highlighted the IL-7/IL-7Rα interaction as a possible target for the treatment of patients with related autoimmune and chronic inflammatory conditions.

Preclinical studies have demonstrated that short-term systemic administration of IL-7Rα blocking antibodies provides an effective treatment in models of autoimmune disease and gastrointestinal inflammation. In IBD models the primary mechanism for efficacy following IL-7R-antagonist treatment appears to involve the local depletion or functional inhibition of colitogenic T cells (IL-7R+ effector/memory T cells) that express moderate to high levels of the IL-7Rα (CD127) and may be activated in inflamed intestine due to increased production of IL-7 by stromal and epithelial cells. In healthy mucosa, gut-resident FOXP3$^+$ CD25$^+$ regulatory T cells (Treg cells) which express very low levels of IL-7R are expected to suppress dysregulated CD4+ T responses to commensal bacteria. However, it is suggested by Heninger et al 2012 that in an IL-7-rich environment, the capacity of FOXP3$^+$CD25$^+$ Treg to suppress the proliferation of conventional T cells is abrogated. In gastrointestinal disease, the blockade of IL-7/IL-7R signalling might therefore help to control T cell mediated inflammation both by inhibiting the activation of effector T cells and by restoring the suppressive functions of regulatory T cells. Evidence from murine IBD models and ex vivo human tissue studies also suggests that IL-7/IL-7Rα-dependent activation of innate immune cells including innate lymphoid cells (ILCs) contributes to processes involved in gastrointestinal inflammatory disease.

Thymic Stromal Lymphopoietin (TSLP) and IL-7R

TSLP is a cytokine produced by epithelial cells in the skin, lung, intestines and ocular tissues which seems to be involved in the regulation of inflammatory processes at mucosal surfaces of the body. TSLP stimulates dendritic cells (DCs) and innate lymphoid cells (ILCs) to induce the secretion of Th2 cytokines (IL-4, IL-5 and IL-13) and promotes the development of Th2-type inflammation. TSLP is now thought to underlie the development of some allergic disorders including atopic dermatitis, rhinitis and also promote intestinal disorders including eosinophilic oesophagitis (EoE) and ulcerative colitis (UC). Paradoxically, TSLP was also reported to be important for the maintenance of immune homeostasis and mucosal protection in the gastrointestinal tract. Recently, the discovery that TSLP can be expressed as two different isoforms has provided a biological explanation for the apparently contrasting activities of this cytokine (Fornasa et al 2015; Tsilingiri et al 2017). Molecular studies have shown that the TSLP gene can give rise to two coding RNAs that are regulated by two different promoter regions. One of the transcripts encodes a long isoform of TSLP (L-TSLP) of 159aa (UNIPROT entry Q969D9, SEQ ID NO: 62) and the second transcript a short form of TSLP (S-TSLP) that encompasses the C-terminal 63aa of L-TSLP (UNIPROT entry Q969D9-2, SEQ ID NO: 63). L-TSLP acts on target cells via a receptor complex that includes a TSLP-specific receptor chain (TSLPR) and the IL-7Rα chain. Recently, structural studies have shown that interactions of IL-7 and L-TSLP with the IL-7Rα chain of the TSLP-receptor complex involve a common IL-7Rα binding site (Verstraete et al 2017).

S-TSLP does not bind to the TSLPR and it is not capable of inhibiting the binding of L-TSLP to this receptor. To the best of the author's knowledge, a specific receptor for S-TSLP has not been identified to date.

Importantly, it has been shown that S-TSLP is expressed preferentially by healthy skin and in healthy intestinal mucosal tissue by epithelial and lamina propria cells. S-TSLP has anti-inflammatory activity; in vitro S-TSLP inhibits the production of pro-inflammatory cytokines by monocyte derived DCs and contributes to the conditioning of CD103+ DCs to a tolerogenic phenotype. Thus it appears that S-TSLP produced by the intestinal epithelium can influence underlying immune cells including dendritic cells and lymphocytes and promote tolerogenic and regulatory responses in health. S-TSLP also displays potent antimicrobial (bacterial and fungal) activity and this may be important for protection against microbial invasion of the mucosal epithelium (Bjerkan et al 2016). S-TSLP expression in healthy tissue is constitutive but can be upregulated by vitamin D3 and PPARγ agonists or down-regulated by pathogenic bacteria that are pro-inflammatory. L-TSLP is absent in healthy tissues but is expressed in response to pro-inflammatory stimuli and plays a critical role in promoting Th2 cytokine associated inflammation by activating DCs and the effector functions of Th2 cells. Native CD4+ T cells that are exposed to L-TSLP-activated DCs undergo proliferation and differentiation to Th2 lymphocytes. L-TSLP is also able to stimulate Th2 innate immune responses through the activation of basophils, ILCs (ILC2) and eosinophils.

Recent studies have shown that the patterns of expression of both TSLP isoforms are changed dramatically from the steady state in intestinal diseases including inflammatory bowel diseases and eosinophilic oesophagitis (EoE). Rimoldi et al 2005 reported that TSLP (which may have been specifically S-TSLP in this instance, in line with the findings of Fornasa et al 2015) was constitutively expressed by primary epithelial cells isolated from healthy colon tissue. However, TSLP expression was found to be undetectable in epithelial cells from 6/9 patients with CD. The inability of CD epithelial cells to produce S-TSLP in diseased mucosa would result in the failure of a mechanism that normally helps to maintain the homeostasis of the gut by generating a non-inflammatory environment. Defects in this mechanism may induce unwanted Th1 inflammatory responses, contributing to the development of CD. In contrast to the lamina propria Th1 cells that predominate in Crohn's disease, lamina propria T cells from patients with ulcerative colitis have been shown to produce the Th2 type cytokines IL-5 and IL-13, these cells only show low levels of IL-4 production, which suggests that they do not display all of the features of classical Th2 cells. Functionally, IL-13 has been shown to promote fibrosis and to cause altered tight junction function in, and apoptosis of, intestinal epithelial cells thereby driving mucosal ulceration. Recently, it was reported in Fornasa et al 2015 that TSLP expression detected with an L-TSLP specific antibody is significantly upregulated in intestinal tissue from patients with ulcerative colitis compared with levels detected in healthy colonic mucosa. Since TSLP-activated dendritic cells (DCs) can induce naive CD4+ T cells to differentiate into IL-5, IL-13 and TNF-producing inflammatory Th2 cells (Liu 2006), the inhibition of this upstream cytokine acting at the epithelial cell-dendritic cell interface might prove to be an effective strategy for the treatment of mucosal inflammation in patients with ulcerative colitis.

Epidemiological data support the involvement of atopic mechanisms and genetic factors in the development of EoE. Importantly, results of genome wide association studies have identified TSLP and its receptor TSLPR as candidate genes in the pathogenesis of EoE (Cianferoni and Spergel, 2015). TSLP expression is increased in oesophageal biopsy specimens of EoE patients and has been localised to stratified squamous epithelial cells by immune-histochemical staining (Noti et al 2013). L-TSLP appears to be a major upstream driver of disease pathology as it strongly promotes the production of cytokines (including CCL-26/Eotaxin-3, IL-4, IL-5, IL-9 and IL-13), and pro-fibrotic factors from Th2 cells, basophils, eosinophils and mast cells that contribute to inflammation and tissue remodelling.

In EoE, TSLP is considered to function as an upstream epithelial 'master-switch' right at the start of the inflammation cascade and consequently, antagonism of this cytokine might allow the inflammatory cascade to be shut down further upstream than previous targeted anti-cytokine therapies. Support for this concept has been provided by positive results from a recent trial with tezepelumab (AMG 157) a first-in-class TSLP antagonist mAb in patients with severe asthma (Corren et al 2017).

In light of the above, it will be appreciated that there is an unmet need for more effective therapies for inflammatory and/or autoimmune diseases such as IBD and EoE. An agent which is capable of inhibiting IL-7 and/or L-TSLP binding to IL-7R, particularly if capable of oral administration, may represent such a therapy and would therefore be highly desirable. WO2013056984, WO2015189302, WO2011094259 and WO2011104687 disclose antibodies directed against IL-7R.

SUMMARY OF THE INVENTION

The present inventors have produced polypeptides which are capable of inhibiting IL-7 and/or L-TSLP binding to IL-7R. These polypeptides bind to IL-7Rα. These polypeptides in particular benefit from surprisingly high potency. They are capable of cross-reacting with cynomolgus monkey IL-7Rα and remain stable on exposure to proteases of the small and large intestine. In one embodiment, these polypeptides have undergone further enhancement by engineering. These further enhanced polypeptides comprise sequences which have been humanised but nonetheless substantially maintain the above advantages.

It has been shown that in some embodiments, the polypeptides of the invention bind IL-7R with high affinity in Biacore studies, and in ELISA are potent inhibitors of IL-7R interactions with both IL-7 and the IL-7-related cytokine L-TSLP. In functional, cell-based assays certain polypeptides of the invention inhibit the biological actions of both cytokines (IL-7-induced Stat5 phosphorylation; L-TSLP-induced TARC production) with potencies similar to the clinical anti-IL-7R mAb829 (also known as "GSK2618960", an anti-IL-7Rα monoclonal antibody disclosed in Ellis et al 2019).

In silico modelling suggests that the dual antagonistic activity of certain polypeptides of the invention is due to binding of the polypeptides to an epitope of the IL-7R that also constitutes a shared binding site for both cytokines. In specificity studies, certain polypeptides of the invention showed no binding activity towards other human IL-7R-family or other cytokine receptors. In cross-species specificity assays certain polypeptides of the invention did not bind mouse IL-7R, but bound to cynomolgus monkey and human IL-7Rs with similar potency; consequently the cynomolgus monkey may be a suitable species for preclinical development studies.

In ex vivo cultures of inflamed ulcerative colitis mucosal tissue, an exemplified polypeptide of the invention inhibited the phosphorylation of signalling proteins and the production of cytokines and chemokines that are associated with pro-inflammatory and immuno-regulatory pathways. Results demonstrated that antagonism of mucosal IL-7R+ve T cells by this polypeptide can inhibit inflammatory processes at least as effectively as the clinical anti-IL-7R mAb829 in a model closely related to the disease environment, providing confidence that polypeptides of the invention may be effective in patients with ulcerative colitis in particular. In vivo, oral dosing of certain polypeptides of the invention in normal mice demonstrated high levels of colonic luminal exposure (micromolar) demonstrating resistance to digestion during passage through the entire GI system.

Accordingly, it may be expected that these polypeptides have particular utility in the prevention or treatment of autoimmune and or inflammatory disease such as inflammatory bowel disease (for example Crohn's disease or ulcerative colitis) or eosinophilic esophagitis, particularly when administered orally.

The present invention provides a polypeptide capable of inhibiting IL-7 and/or L-TSLP binding to IL-7R. The present invention also provides constructs and pharmaceutical compositions comprising these polypeptides. Also provided are nucleic acids encoding such polypeptides, methods for preparing such polypeptides, cDNA and vectors comprising nucleic acids encoding such polypeptides, host cells capable of expressing such polypeptides and uses of such polypeptides.

For the avoidance of doubt regarding the term 'and/or' above, 'a polypeptide capable of inhibiting IL-7 binding to IL-7R' encompasses a polypeptide capable of inhibiting IL-7 and L-TSLP binding to IL-7R. Similarly, 'a polypeptide capable of inhibiting L-TSLP binding to IL-7R' encompasses a polypeptide capable of inhibiting IL-7 and L-TSLP binding to IL-7R.

Polypeptides of the present invention may, in at least some embodiments, have one or more of the following advantages compared to substances of the prior art which are capable of inhibiting IL-7 and/or L-TSLP binding to IL-7R:

(i) increased affinity for IL-7Rα;
(ii) increased specificity for IL-7Rα;
(iii) increased neutralising capability against IL-7 or L-TSLP binding IL-7R;
(iv) inhibiting binding of both IL-7 and L-TSLP to IL-7R;
(v) increased cross-reactivity with IL-7Rα from different species such as human and cynomolgus monkey;
(vi) reduced immunogenicity, for example when administered to a mouse, cynomolgus monkey or human;

(vii) increased stability in the presence of proteases, for example (a) in the presence of proteases found in the small and/or large intestine and/or IBD inflammatory proteases, for example trypsin, chymotrypsin, MMP3, MMP12, other MMPs and cathepsin and/or (b) in the presence of proteases from gut commensal microflora and/or pathogenic bacteria, actively secreted and/or released by lysis of microbial cells found in the small and/or large intestine;

(viii) increased stability to protease degradation during production (for example resistance to yeast proteases);

(ix) increased suitability for oral administration;

(x) increased suitability for local delivery to the intestinal tract and lamina propria following oral administration;

(xi) increased suitability for local delivery to the esophagus following oral administration;

(xii) increased suitability for expression, in a heterologous host such as bacteria such as Escherichia coli, or a yeast belonging to the genera *Aspergillus, Saccharomyces, Kluyveromyces, Hansenula* or *Pichia*, such as *Saccharomyces cerevisiae* or *Pichia pastoris;*

(xiii) suitability for, and improved properties for, use in a pharmaceutical;

(xiv) suitability for, and improved properties for, use in a functional food;

(xv) improved tissue penetration such as penetration of inflamed colonic mucosal epithelium and submucosal tissues to access the sub mucosal lamina propria;

(xvi) increased suitability for formatting in a multispecific format;

(xvii) binding to novel epitopes.

Advantages (i) to (xvii) above may potentially be realised by the polypeptides of the present invention in a monovalent format or in a multivalent format such as a bihead format (for example homobihead or heterobihead formats).

Recitation of "IL-7R" in the points above (and throughout the description) may also be replaced with "IL-7Rα" as appropriate, due to the polypeptide of the invention binding to specifically the IL-7Rα subunit of IL-7R.

DESCRIPTION OF THE SEQUENCES

Figure 1:
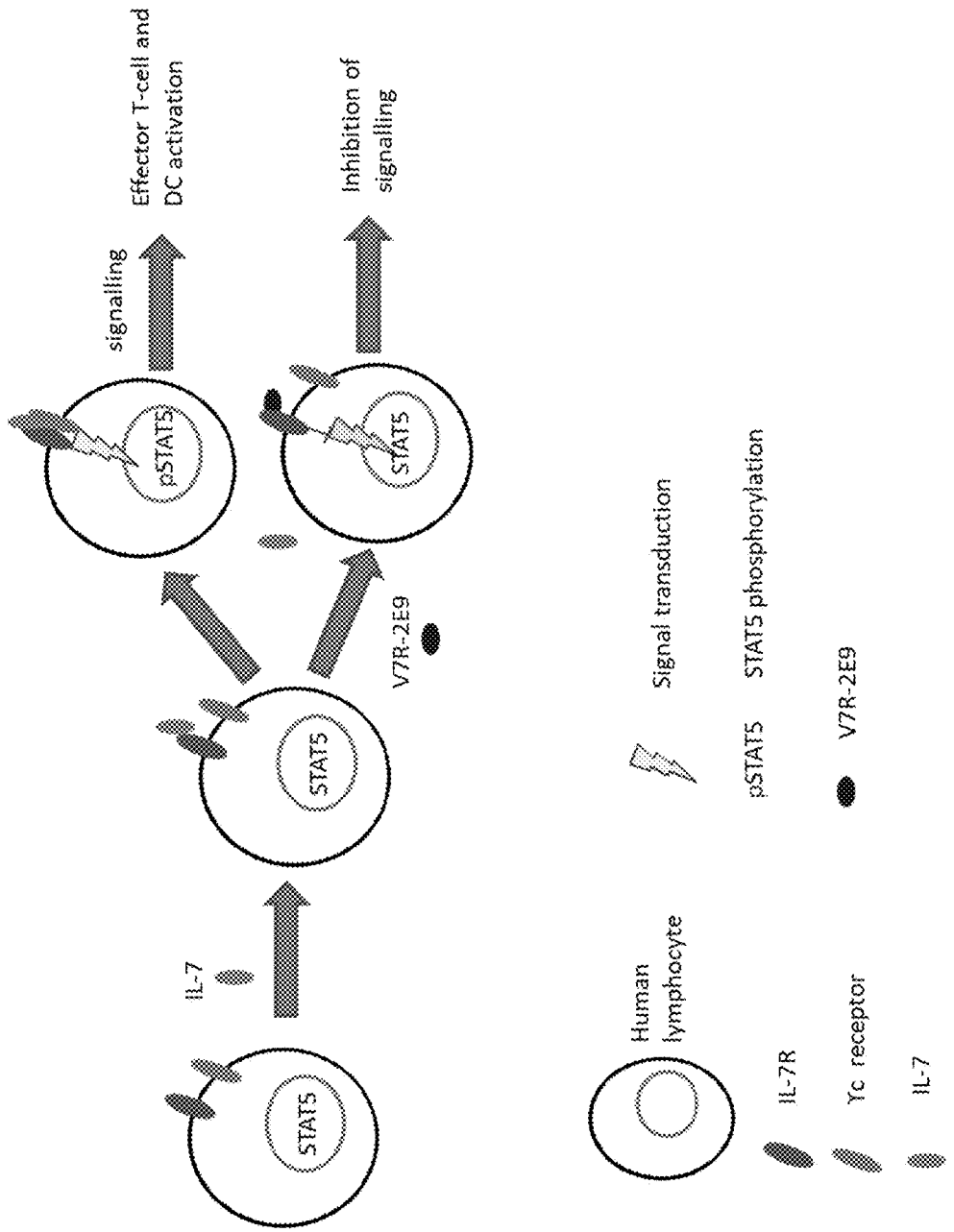
FIG. 1—Inhibition of IL-7 induced pSTAT-5 in human lymphocytes
Figure 2:
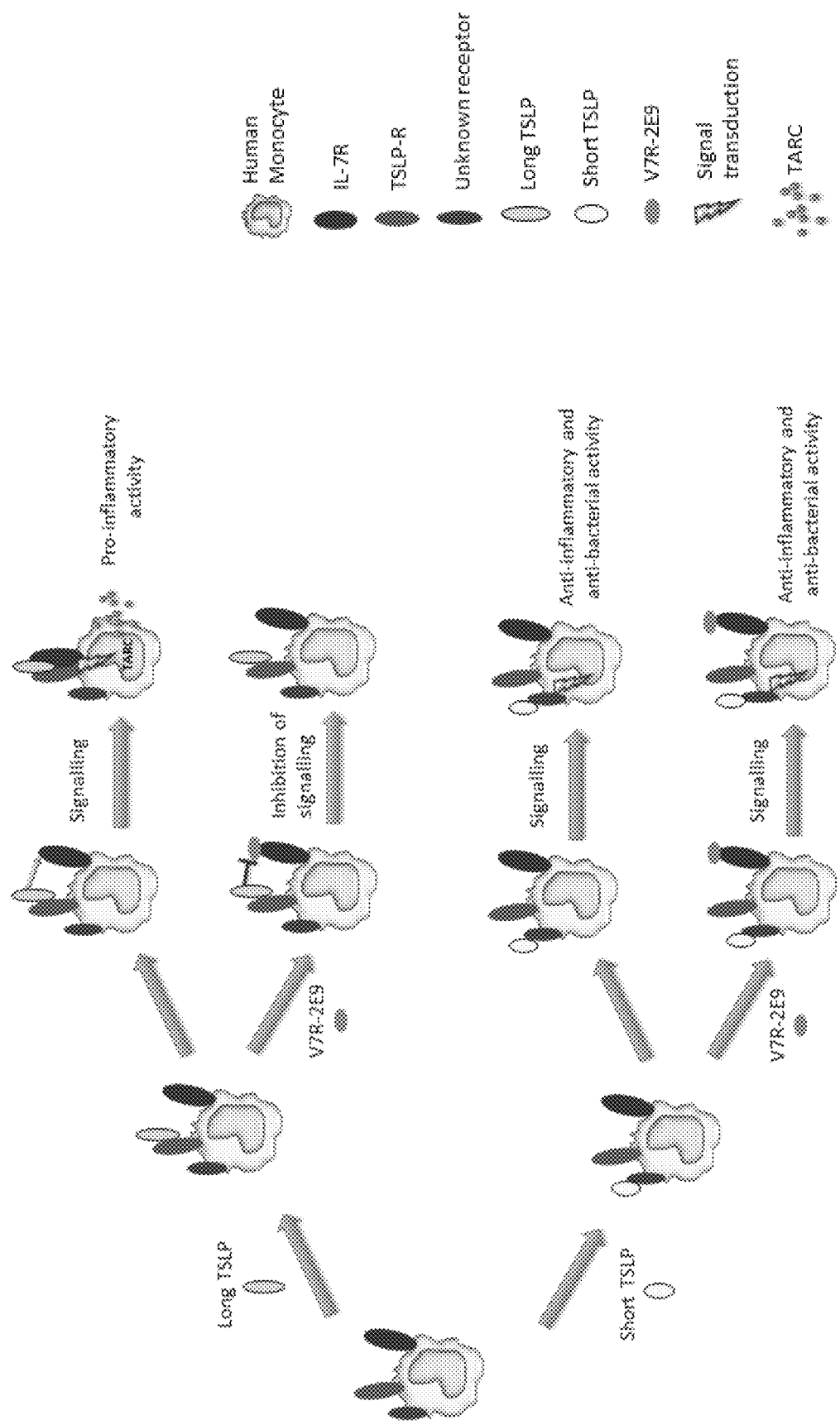
FIG. 2—Inhibition of TSLP induced TARC secretion in human monocytes

SEQ ID NO: 1—Polypeptide sequence of ID-A62U CDR1
SEQ ID NO: 2—Polypeptide sequence of ID-A62U CDR2
SEQ ID NO: 3—Polypeptide sequence of ID-A62U CDR3
SEQ ID NO: 4—Polypeptide sequence of ID-A62U FR1
SEQ ID NO: 5—Polypeptide sequence of ID-A62U FR2
SEQ ID NO: 6—Polypeptide sequence of ID-A62U FR3
SEQ ID NO: 7—Polypeptide sequence of ID-A62U FR4
SEQ ID NO: 8—Polypeptide sequence of ID-A62U
SEQ ID NO: 9—Polypeptide sequence of V7R-2B6
SEQ ID NO: 10—Polypeptide sequence of V7R-2E5
SEQ ID NO: 11—Polypeptide sequence of V7R-2E9
SEQ ID NO: 12—Polypeptide sequence of V7R-2F6
SEQ ID NO: 13—Polypeptide sequence of V7R-3B5
SEQ ID NO: 14—Polypeptide sequence of V7R-4F6
SEQ ID NO: 15—Polypeptide sequence of V7R-6C12
SEQ ID NO: 16—Polypeptide sequence of ID-A2U
SEQ ID NO: 17—Polypeptide sequence of ID-A3U
SEQ ID NO: 18—Polypeptide sequence of ID-A4U
SEQ ID NO: 19—Polypeptide sequence of ID-A5U
SEQ ID NO: 20—Polypeptide sequence of ID-A6U
SEQ ID NO: 21—Polypeptide sequence of ID-A7U
SEQ ID NO: 22—Polypeptide sequence of ID-A8U
SEQ ID NO: 23—Polypeptide sequence of ID-A9U
SEQ ID NO: 24—Polypeptide sequence of ID-A10U
SEQ ID NO: 25—Polypeptide sequence of ID-A11U
SEQ ID NO: 26—Polypeptide sequence of ID-A12U
SEQ ID NO: 27—Polypeptide sequence of ID-A13U
SEQ ID NO: 28—Polypeptide sequence of ID-A14U
SEQ ID NO: 29—Polypeptide sequence of ID-A15U
SEQ ID NO: 30—Polypeptide sequence of ID-A16U
SEQ ID NO: 31—Polypeptide sequence of ID-A17U
SEQ ID NO: 32—Polypeptide sequence of ID-A18U
SEQ ID NO: 33—Polypeptide sequence of ID-A19U
SEQ ID NO: 34—Polypeptide sequence of ID-A20U
SEQ ID NO: 35—Polypeptide sequence of ID-A21U
SEQ ID NO: 36—Polypeptide sequence of ID-A23U
SEQ ID NO: 37—Polypeptide sequence of ID-A24U
SEQ ID NO: 38—Polypeptide sequence of ID-A25U
SEQ ID NO: 39—Polypeptide sequence of ID-A26U
SEQ ID NO: 40—Polypeptide sequence of ID-A27U
SEQ ID NO: 41—Polypeptide sequence of ID-A28U
SEQ ID NO: 42—Polypeptide sequence of ID-A29U
SEQ ID NO: 43—Polypeptide sequence of ID-A30U
SEQ ID NO: 44—Polypeptide sequence of ID-A31U
SEQ ID NO: 45—Polypeptide sequence of ID-A32U
SEQ ID NO: 46—Polypeptide sequence of ID-A33U
SEQ ID NO: 47—Polypeptide sequence of ID-A34U
SEQ ID NO: 48—Polypeptide sequence of ID-A35U
SEQ ID NO: 49—Polypeptide sequence of ID-A36U
SEQ ID NO: 50—Polypeptide sequence of ID-A37U
SEQ ID NO: 51—Polypeptide sequence of ID-A38U
SEQ ID NO: 52—Polypeptide sequence of ID-A39U
SEQ ID NO: 53—Polypeptide sequence of ID-A40U
SEQ ID NO: 54—Polypeptide sequence of ID-A43U
SEQ ID NO: 55—Polypeptide sequence of ID-A50U
SEQ ID NO: 56—Polypeptide sequence of ID-A52U SEQ ID NO: 57—Polypeptide sequence of ID-A53U
SEQ ID NO: 58—Polypeptide sequence of ID-A54U
SEQ ID NO: 59—Polypeptide sequence of ID-A55U
SEQ ID NO: 60—Polypeptide sequence of ID-A57U
SEQ ID NO: 61—Polypeptide sequence of ID-A59U
SEQ ID NO: 62—Polypeptide sequence of L-TSLP
SEQ ID NO: 63—Polypeptide sequence of S-TSLP
SEQ ID NO: 64—Polypeptide sequence of full length human common γ-chain receptor
SEQ ID NO: 65—Polypeptide sequence of full length human-IL-7Rα
SEQ ID NO: 66—Polypeptide sequence of full length cynomolgus monkey IL-7Rα
SEQ ID NO: 67—Polypeptide sequence of cynomolgus monkey IL-7Rα extracellular domain
SEQ ID NO: 68—Polypeptide sequence of human-IL-7Rα extracellular domain
SEQ ID NO: 69—Polynucleotide sequence encoding ID-A59U
SEQ ID NO: 70—Polynucleotide sequence encoding ID-A62U
SEQ ID NO: 71—Polypeptide sequence of V7R-2B6 CDR1
SEQ ID NO: 72—Polypeptide sequence of V7R-2E9 CDR2
SEQ ID NO: 73—Polypeptide sequence of V7R-2F6 CDR2
SEQ ID NO: 74—Polypeptide sequence of V7R-4F6 CDR2
SEQ ID NO: 75—Polypeptide sequence of V7R-2B6 CDR2
SEQ ID NO: 76—Polypeptide sequence of ID-A14U CDR2
SEQ ID NO: 77—Polypeptide sequence of V7R-6C12 CDR3
SEQ ID NO: 78—Polypeptide sequence of V7R-2B6 CDR3
SEQ ID NO: 79—Polypeptide sequence which suitably occupies residues 9-14 of ID-A62U FR2 (SEQ ID NO: 5)
SEQ ID NO: 80—Polypeptide sequence which suitably does not occupy residues 9-14 of ID-A62U FR2 (SEQ ID NO: 5)
SEQ ID NO: 81—Polynucleotide sequence of 3' primer containing the SpeI site
SEQ ID NO: 82—Polypeptide sequence of CDR1 with an optional conservative substitution at residue 1 of SEQ ID NO: 1
SEQ ID NO: 83—Polypeptide sequence of CDR2 with optional conservative substitutions at residues 2, 3, 7, 12 and 16 of SEQ ID NO: 2
SEQ ID NO: 84—Polypeptide sequence of CDR3 with optional conservative substitutions at residues 3 and 9 of SEQ ID NO: 3
SEQ ID NO: 85—Polypeptide sequence of protease-labile linker formula 1
SEQ ID NO: 86—Polypeptide sequence of protease-labile linker formula 2
SEQ ID NO: 87—Polypeptide sequence of preferred variant of protease-labile linker formulae 1 and 2
SEQ ID NO: 88—Polypeptide sequence of non-protease-labile linker formula 3
SEQ ID NO: 89—Polypeptide sequence of preferred non-protease-labile linker

DETAILED DESCRIPTION OF THE INVENTION

Polypeptides such as Antibodies and Antibody Fragments Including Immunoglobulin Chain Variable Domains (ICVDs) such as the VH and VHH Polypeptides are organic polymers consisting of a number of amino acid residues bonded together in a chain. As used herein, 'polypeptide' is used interchangeably with 'protein' and 'peptide'. Polypeptides are said to be binding polypeptides when they contain one or more stretches of amino acid residues which form a binding site, capable of binding to an epitope on a target, with an affinity (suitably expressed as a Kd value, a Ka value, a $k_{on}$-rate and/or a $k_{off}$-rate, as further described herein).

Binding polypeptides include polypeptides such as DARPins (Binz et al. 2003), Affimers™ (Johnson et al 2012), Fynomers™ (Grabulovski et al 2007), Centyrins (Goldberg et al 2016), Affitins (e.g. Nanofitins®, Krehenbrink et al 2008), cyclic peptides, antibodies and antibody fragments. Binding polypeptides also include polypeptides such as Affibodies (Nygren 2008), Affilins (Ebersbach et al. 2007), Alphabodies (Desmet et al 2014), Anticalins (Skerra et al 2008), Avimers (Silverman et al 2005), Kunitz domain peptides (Nixon and Wood 2006), Monobodies (Koide and Koide 2007), nanoCLAMPs (Suderman et al 2017), Adnectins (Lipovsek 2011) and bicyclic peptides.

A conventional antibody or immunoglobulin (Ig) is a protein comprising four polypeptide chains: two heavy (H) chains and two light (L) chains. Each chain is divided into a constant region and a variable domain. The heavy chain variable domains are abbreviated herein as VHC, and the light (L) chain variable domains are abbreviated herein as VLC. These domains, domains related thereto and domains derived therefrom, are referred to herein as immunoglobulin chain variable domains. The VHC and VLC domains can be further subdivided into regions of hypervariability, termed "complementarity determining regions" ("CDRs"), interspersed with regions that are more conserved, termed "framework regions" ("FRs"). The framework and complementarity determining regions have been precisely defined (Kabat et al 1991). In a conventional antibody, each VHC and VLC is composed of three CDRs and four FRs, arranged from amino-terminus to carboxy-terminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains interconnected by e.g. disulfide bonds, and the heavy chains similarity connected. The heavy chain constant region includes three domains, CH1, CH2 and CH3. The light chain constant region is comprised of one domain, CL. The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1q) of the classical complement system. The term antibody includes immunoglobulins of types IgA, IgG, IgE, IgD, IgM (as well as subtypes thereof), wherein the light chains of the immunoglobulin may be kappa or lambda types. The overall structure of immunoglobulin-gamma (IgG) antibodies assembled from two identical heavy (H)-chain and two identical light (L)-chain polypeptides is well established and highly conserved in mammals (Padlan 1994).

An exception to conventional antibody structure is found in sera of Camelidae. In addition to conventional antibodies, these sera possess special IgG antibodies. These IgG antibodies, known as heavy-chain antibodies (HCAbs), are devoid of the L chain polypeptide and lack the first constant domain (CH1). At its N-terminal region, the H chain of the homodimeric protein contains a dedicated immunoglobulin chain variable domain, referred to as the VHH, which serves to associate with its cognate antigen (Muyldermans 2013, Hamers-Casterman et al 1993, Muyldermans et al 1994).

An antigen-binding fragment (or "antibody fragment" or "immunoglobulin fragment") as used herein refers to a portion of an antibody that specifically binds to IL-7Rα (e.g. a molecule in which one or more immunoglobulin chains is not full length, but which specifically binds to IL-7Rα). Examples of binding fragments encompassed within the term antigen-binding fragment include:
 (i) a Fab fragment (a monovalent fragment consisting of the VLC, VHC, CL and CH1 domains);
 (ii) a F(ab')$_2$ fragment (a bivalent fragment comprising two Fab fragments linked by a disulfide bridge at the hinge region);
 (iii) a Fd fragment (consisting of the VHC and CH1 domains);
 (iv) a Fv fragment (consisting of the VLC and VHC domains of a single arm of an antibody);
 (v) an scFv fragment (consisting of VLC and VHC domains joined, using recombinant methods, by a synthetic linker that enables them to be made as a single protein chain in which the VLC and VHC regions pair to form monovalent molecules);
 (vi) a VH (an immunoglobulin chain variable domain consisting of a VHC domain (Ward et al 1989);
 (vii) a VL (an immunoglobulin chain variable domain consisting of a VLC domain);
 (viii) a V-NAR (an immunoglobulin chain variable domain consisting of a VHC domain from chondrichthyes IgNAR (Roux et al 1998 and Griffiths et al 2013)
 (ix) a VHH.

The total number of amino acid residues in a VHH or VH may be in the region of 110-130, is suitably 115-120, and is most suitably 118.

Immunoglobulin chain variable domains of the invention may for example be obtained by preparing a nucleic acid encoding an immunoglobulin chain variable domain using techniques for nucleic acid synthesis, followed by expression of the nucleic acid thus obtained According to a specific embodiment, an immunoglobulin chain variable domain of the invention does not have an amino acid sequence which is exactly the same as (i.e. shares 100% sequence identity with) the amino acid sequence of a naturally occurring polypeptide such as a VH or VHH domain of a naturally occurring antibody.

The examples provided herein relate to immunoglobulin chain variable domains per se which bind to IL-7Rα. The principles of the invention disclosed herein are, however, equally applicable to any IL-7Rα binding polypeptides, such as antibodies and antibody fragments. For example, the anti-IL-7Rα immunoglobulin chain variable domains disclosed herein may be incorporated into a polypeptide such as a full-length antibody. Such an approach is demonstrated by McCoy et al 2014, who provide an anti-HIV VHH engineered as a fusion with a human Fc region (including hinge, CH2 and CH3 domains), expressed as a dimer construct.

Substituting at least one amino acid residue in the framework region of a non-human immunoglobulin chain variable domain with the corresponding residue from a human immunoglobulin chain variable domain is humanisation. Humanisation of a variable domain may reduce immunogenicity in humans.

Suitably, the polypeptide of the present invention comprises an immunoglobulin chain variable domain. More suitably, the polypeptide of the present invention consists of an immunoglobulin chain variable domain, such as an immunoglobulin heavy chain variable domain. Suitably, the polypeptide of the present invention is an antibody or an antibody fragment. More suitably the polypeptide of the present invention is an antibody fragment. Suitably the antibody fragment is an immunoglobulin chain variable domain such as a VHH, a VH or a VL. Suitably the antibody fragment is a VHH, a VH, a VL, a V-NAR, an scFv, a Fab fragment, or a F(ab')2 fragment. Suitably the antibody fragment is an immunoglobulin heavy chain variable domain. More suitably the antibody fragment is a VHH or VH, and most suitably a VHH.

Specificity, Affinity, Avidity and Cross-Reactivity

Specificity refers to the number of different types of antigens or antigenic determinants to which a particular antigen-binding polypeptide can bind. The specificity of an antigen-binding polypeptide is the ability of the antigen-binding polypeptide to recognise a particular antigen as a unique molecular entity and distinguish it from another.

Affinity, represented by the equilibrium constant for the dissociation of a target from a binding polypeptide (Kd), is a measure of the binding strength between a target and a binding site on a binding polypeptide: the lesser the value of the Kd, the stronger the binding strength between a target and the binding polypeptide (alternatively, the affinity can also be expressed as the affinity constant (Ka), which is 1/Kd). Affinity can be determined by known methods, depending on the specific antigen of interest. Suitably, affinity is determined using a dynamically switchable biosurface (e.g. "switchSENSE®", see Knezevic et al 2012) or by surface plasmon resonance.

Avidity is the measure of the strength of binding between an antigen-binding polypeptide and the pertinent antigen. Avidity is related to both the affinity between an antigenic determinant and its antigen binding site on the antigen-binding polypeptide and the number of pertinent binding sites present on the antigen-binding polypeptide.

Suitably, the polypeptide of the invention binds to IL-7Rα with an equilibrium dissociation constant (Kd) of $10^{-7}$ M or less, more suitably $10^{-8}$ M or less, more suitably $10^{-9}$ M or less and more suitably $10^{-10}$ M or less.

Suitably the polypeptide of the invention binds to IL-7Rα with an equilibrium dissociation constant lower than that of mAb829 in the same assay. Suitably the polypeptide of the invention binds to IL-7Rα with an equilibrium dissociation constant of $5.67 \times 10^{-10}$ M or lower, more suitably lower than $5.67 \times 10^{-10}$ M. mAb829 is also known as "GSK2618960", an anti-IL-7Rα monoclonal antibody disclosed in Ellis et al 2019.

In one embodiment, the affinity of the polypeptide of the invention is established by coating directly on a Biacore (or equivalent) sensor plate, or by fusion to an Fc and capture with an anti-human IgG Fc, wherein the polypeptide is flowed over the plate to detect binding. Suitably a Biacore T200 plate is used at 25° C. in HBS-EP+ (GE Healthcare) running buffer at 30 ul/min.

An anti-IL-7Rα polypeptide, an IL-7Rα binding polypeptide, a polypeptide which interacts with IL-7Rα, or a polypeptide against IL-7Rα, are all effectively polypeptides which bind to IL-7Rα. A polypeptide of the invention may bind to a linear or conformational epitope on IL-7Rα.

Suitably, the polypeptide of the invention will bind to human IL-7Rα. More suitably, the polypeptide of the invention will bind to both human and at least one additional primate IL-7Rα selected from the group consisting of baboon IL-7Rα, marmoset IL-7Rα, cynomolgus IL-7Rα and rhesus IL-7Rα. Most suitably, the polypeptide of the invention binds to both human and cynomolgus IL-7Rα.

Suitably, the polypeptide of the invention will neutralise human IL-7 and/or human L-TSLP binding human IL-7R. More suitably, the polypeptide of the invention will neutralise human IL-7 and/or human L-TSLP binding both human and at least one additional primate IL-7R selected from the group consisting of baboon IL-7R, marmoset IL-7R, cynomolgus IL-7R and rhesus IL-7R. Most suitably, the polypeptide of the invention will neutralise human IL-7 and human L-TSLP binding human IL-7R.

Suitably the polypeptide of the invention binds to IL-7Rα (e.g. human-IL-7Rα, SEQ ID NO: 65 and/or cynomolgus monkey IL-7Rα, SEQ ID NO: 66) or to the γ-chain receptor (e.g. human common γ-chain receptor, SEQ ID NO: 64). More suitably the polypeptide of the invention binds to IL-7Rα, most suitably human IL-7Rα. More specifically the polypeptide of the invention binds to the extracellular region of IL-7Rα (SEQ ID NOs: 67 and 68, extracellular regions of cynomolgus and human IL-7Rα, respectively), i.e. the polypeptide sequence of IL-7Rα lacking the transmembrane helix and cytoplasmic domain.

Suitably, IL-7Rα is a polypeptide comprising SEQ ID NO: 65 or SEQ ID NO: 66, more suitably IL-7Rα is a polypeptide consisting of SEQ ID NO: 65 or SEQ ID NO: 66. More suitably, IL-7Rα is a polypeptide comprising SEQ ID NO: 65, more suitably IL-7Rα is a polypeptide consisting of SEQ ID NO: 65. The polypeptide sequence of mature, full length human IL-7Rα is also available under UniProt entry P16871.

Polypeptides capable of reacting with IL-7Rα from humans and IL-7Rα from another species ("cross-reacting"), such as with cynomolgus monkey IL-7Rα, are advantageous because they allow preclinical studies to be more readily performed in animal models.

Suitably the polypeptide of the invention is directed against epitopes on IL-7Rα that lie in and/or form part of the receptor binding site(s) of IL-7 and/or L-TSLP, such that said polypeptide of the invention, upon binding to IL-7Rα, is capable inhibiting or reducing IL-7 and/or L-TSLP signalling.

The polypeptides of the present invention bind to one or more epitope(s) on IL-7Rα. In one aspect of the invention there is provided a polypeptide which binds to the same epitope on IL-7Rα as V7R-2E5, V7R-2E9, V7R-2F6, V7R-6C12, V7R-2B6, V7R-3B5 or V7R-4F6.

Suitably, the polypeptide of the invention is isolated. An "isolated" polypeptide is one that is removed from its original environment. For example, a naturally-occurring polypeptide of the invention is isolated if it is separated from some or all of the coexisting materials in the natural system.

Potency, Inhibition and Neutralisation

Potency is a measure of the activity of a therapeutic agent expressed in terms of the amount required to produce an effect of given intensity. A highly potent agent evokes a greater response at low concentrations compared to an agent of lower potency that evokes a smaller response at low concentrations. Potency is a function of affinity and efficacy. Efficacy refers to the ability of therapeutic agent to produce a biological response upon binding to a target ligand and the quantitative magnitude of this response. The term half maximal effective concentration (EC50) refers to the concentration of a therapeutic agent which causes a response halfway between the baseline and maximum after a specified exposure time. The therapeutic agent may cause inhibition or stimulation. It is commonly used, and is used herein, as a measure of potency.

A neutralising polypeptide for the purposes of the invention is a polypeptide which binds to IL-7Rα, inhibiting the binding of IL-7R to IL-7 and/or L-TSLP as measured by ELISA. A specific ELISA method suitable for determining the level of inhibition in this context is detailed in Example 3 below.

Suitably the polypeptide of the invention neutralizes IL-7R binding to IL-7 with an EC50 of 2.00 nM or less, such as 1.50 nM or less, such as 1.00 nM or less, such as 0.90 nM or less, such as 0.80 nM or less, such as 0.70 nM or less, such as 0.65 nM or less, such as 0.60 nM or less, such as 0.55 nM or less, such as 0.50 nM or less, such as 0.45 nM or less, such as 0.4 nM or less, such as 0.35 nM or less, such as 0.30 nM or less.

Suitably the EC50 is established using the IL-7/IL-7R neutralisation ELISA detailed in Example 3 below.

Polypeptide and Polynucleotide Sequences

For the purposes of comparing two closely-related polypeptide sequences, the "% sequence identity" between a first polypeptide sequence and a second polypeptide sequence may be calculated using NCBI BLAST v2.0, using standard settings for polypeptide sequences (BLASTP). For the purposes of comparing two closely-related polynucleotide sequences, the "% sequence identity" between a first nucleotide sequence and a second nucleotide sequence may be calculated using NCBI BLAST v2.0, using standard settings for nucleotide sequences (BLASTN). The BLAST algorithm parameters W, T, and X determine the sensitivity and speed of the alignment. The BLASTN program (for nucleotide sequences) uses as defaults a wordlength (VV) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands. The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more suitably less than about 0.01, and most suitably less than about 0.001.

Polypeptide or polynucleotide sequences are said to be the same as or identical to other polypeptide or polynucleotide sequences, if they share 100% sequence identity over their entire length. Residues in sequences are numbered from left to right, i.e. from N- to C-terminus for polypeptides; from 5' to 3' terminus for polynucleotides.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced % sequence identity. For example, if the identical sequences are 9 amino acid residues long, one substitution in the second sequence results in a sequence identity of 88.9%. If the identical sequences are 17 amino acid residues long, two substitutions in the second sequence results in a sequence identity of 88.2%. If the identical sequences are 7 amino acid residues long, three substitutions in the second sequence results in a sequence identity of 57.1%. If first and second polypeptide sequences are 9 amino acid residues long and share 6 identical residues, the first and second polypeptide sequences share greater than 66% identity (the first and second polypeptide sequences share 66.7% identity). If first and second polypeptide sequences are 17 amino acid residues long and share 16 identical residues, the first and second polypeptide sequences share greater than 94% identity (the first and second polypeptide sequences share 94.1% identity). If first and second polypeptide sequences are 7 amino acid residues long and share 3 identical residues, the first and second polypeptide sequences share greater than 42% identity (the first and second polypeptide sequences share 42.9% identity).

Alternatively, for the purposes of comparing a first, reference polypeptide sequence to a second, comparison polypeptide sequence, the number of additions, substitutions and/or deletions made to the first sequence to produce the second sequence may be ascertained. An addition is the addition of one amino acid residue into the sequence of the first polypeptide (including addition at either terminus of the first polypeptide). A substitution is the substitution of one amino acid residue in the sequence of the first polypeptide with one different amino acid residue. A deletion is the deletion of one amino acid residue from the sequence of the first polypeptide (including deletion at either terminus of the first polypeptide).

For the purposes of comparing a first, reference polynucleotide sequence to a second, comparison polynucleotide sequence, the number of additions, substitutions and/or deletions made to the first sequence to produce the second sequence may be ascertained. An addition is the addition of one nucleotide residue into the sequence of the first polynucleotide (including addition at either terminus of the first polynucleotide). A substitution is the substitution of one nucleotide residue in the sequence of the first polynucleotide with one different nucleotide residue. A deletion is the deletion of one nucleotide residue from the sequence of the first polynucleotide (including deletion at either terminus of the first polynucleotide).

A "conservative" amino acid substitution is an amino acid substitution in which an amino acid residue is replaced with another amino acid residue of similar chemical structure and which is expected to have little influence on the function, activity or other biological properties of the polypeptide. Such conservative substitutions suitably are substitutions in which one amino acid within the following groups is substituted by another amino acid residue from within the same group:

| Group | Amino acid residue |
|---|---|
| Non-polar aliphatic | Glycine |
| | Alanine |
| | Valine |
| | Leucine |
| | Isoleucine |
| Aromatic | Phenylalanine |
| | Tyrosine |
| | Tryptophan |
| Polar uncharged | Serine |
| | Threonine |
| | Asparagine |
| | Glutamine |
| Negatively charged | Aspartate |
| | Glutamate |
| Positively charged | Lysine |
| | Arginine |

Suitably, a hydrophobic amino acid residue is a non-polar amino acid. More suitably, a hydrophobic amino acid residue is selected from V, I, L, M, F, W or C.

As used herein, numbering of polypeptide sequences and definitions of CDRs and FRs are as defined according to the Kabat system (Kabat et al 1991). A "corresponding" amino acid residue between a first and second polypeptide sequence is an amino acid residue in a first sequence which shares the same position according to the Kabat system with an amino acid residue in a second sequence, whilst the amino acid residue in the second sequence may differ in identity from the first. Suitably corresponding residues will share the same number (and letter) if the framework and CDRs are the same length according to Kabat definition. Alignment can be achieved manually or by using, for example, a known computer algorithm for sequence alignment such as NCBI BLAST v2.0 (BLASTP or BLASTN) using standard settings.

The polypeptide sequence of ID-A62U, a polypeptide of the invention, is provided below in Kabat format:

| H1 | H2 | H3 | H4 | H5 | H6 | H7 | H8 | H9 | H10 |
|---|---|---|---|---|---|---|---|---|---|
| D | V | Q | L | V | E | S | G | G | G |
| 1 | 2 | 3 | 4 | 5 | 6 | 7 | 8 | 9 | 10 |

| H11 | H12 | H13 | H14 | H15 | H16 | H17 | H18 | H19 | H20 |
|---|---|---|---|---|---|---|---|---|---|
| L | V | Q | A | G | G | S | L | R | L |
| 11 | 12 | 13 | 14 | 15 | 16 | 17 | 18 | 19 | 20 |

| H21 | H22 | H23 | H24 | H25 | H26 | H27 | H28 | H29 | H30 |
|---|---|---|---|---|---|---|---|---|---|
| S | C | E | S | S | I | S | T | F | S |
| 21 | 22 | 23 | 24 | 25 | 26 | 27 | 28 | 29 | 30 |

CDR-H1

| H31 | H32 | H33 | H34 | H35 | H36 | H37 | H38 | H39 | H40 |
|---|---|---|---|---|---|---|---|---|---|
| S  | D  | A  | M  | G  | W  | F  | R  | Q  | A  |
| 31 | 32 | 33 | 34 | 35 | 36 | 37 | 38 | 39 | 40 |

| H41 | H42 | H43 | H44 | H45 | H46 | H47 | H48 | H49 | CDR-H2 H50 |
|---|---|---|---|---|---|---|---|---|---|
| P  | G  | K  | E  | L  | E  | F  | L  | A  | A  |
| 41 | 42 | 43 | 44 | 45 | 46 | 47 | 48 | 49 | 50 |

CDR-H2

| H51 | H52 | H52A | H53 | H54 | H55 | H56 | H57 | H58 | H59 |
|---|---|---|---|---|---|---|---|---|---|
| I  | G  | W  | S  | G  | A  | V  | T  | H  | Y  |
| 51 | 52 | 53 | 54 | 55 | 56 | 57 | 58 | 59 | 60 |

CDR-H2

| H60 | H61 | H62 | H63 | H64 | H65 | H66 | H67 | H68 | H69 |
|---|---|---|---|---|---|---|---|---|---|
| S  | D  | S  | V  | K  | G  | R  | F  | T  | I  |
| 61 | 62 | 63 | 64 | 65 | 66 | 67 | 68 | 69 | 70 |

| H70 | H71 | H72 | H73 | H74 | H75 | H76 | H77 | H78 | H79 |
|---|---|---|---|---|---|---|---|---|---|
| S  | R  | D  | N  | A  | K  | N  | T  | V  | Y  |
| 71 | 72 | 73 | 74 | 75 | 76 | 77 | 78 | 79 | 80 |

| H80 | H81 | H82 | H82A | H82B | H82C | H83 | H84 | H85 | H86 |
|---|---|---|---|---|---|---|---|---|---|
| L  | Q  | M  | N  | S  | L  | R  | A  | E  | D  |
| 81 | 82 | 83 | 84 | 85 | 86 | 87 | 88 | 89 | 90 |

| H87 | H88 | H89 | H90 | H91 | H92 | H93 | H94 | CDR-H3 H95 | H96 |
|---|---|---|---|---|---|---|---|---|---|
| T  | G  | R  | Y  | Y  | C  | A  | E  | D  | Y  |
| 91 | 92 | 93 | 94 | 95 | 96 | 97 | 98 | 99 | 100 |

CDR-H3

| H97 | H98 | H99 | H100 | H100A | H101 | H102 | H103 | H104 | H105 |
|---|---|---|---|---|---|---|---|---|---|
| D  | T  | D  | V  | W  | Q  | Y  | W  | G  | Q  |
| 101 | 102 | 103 | 104 | 105 | 106 | 107 | 108 | 109 | 110 |

| H106 | H107 | H108 | H109 | H110 | H111 | H112 | H113 |
|---|---|---|---|---|---|---|---|
| G  | T  | Q  | V  | T  | V  | S  | S  |
| 111 | 112 | 113 | 114 | 115 | 116 | 117 | 118 |

The polypeptide sequence of ID-A59U, a further polypeptide of the invention, is provided below in Kabat format:

| H1 | H2 | H3 | H4 | H5 | H6 | H7 | H8 | H9 | H10 |
|---|---|---|---|---|---|---|---|---|---|
| D | V | Q | L | V | E | S | G | G | G |
| 1 | 2 | 3 | 4 | 5 | 6 | 7 | 8 | 9 | 10 |

| H11 | H12 | H13 | H14 | H15 | H16 | H17 | H18 | H19 | H20 |
|---|---|---|---|---|---|---|---|---|---|
| L | V | Q | A | G | G | S | L | R | L |
| 11 | 12 | 13 | 14 | 15 | 16 | 17 | 18 | 19 | 20 |

| H21 | H22 | H23 | H24 | H25 | H26 | H27 | H28 | H29 | H30 |
|---|---|---|---|---|---|---|---|---|---|
| S | C | E | S | S | I | S | T | F | S |
| 21 | 22 | 23 | 24 | 25 | 26 | 27 | 28 | 29 | 30 |

-continued

| CDR-H1 | | | | | | | | | |
|---|---|---|---|---|---|---|---|---|---|
| H31 | H32 | H33 | H34 | H35 | H36 | H37 | H38 | H39 | H40 |
| S | D | A | M | G | W | F | R | Q | A |
| 31 | 32 | 33 | 34 | 35 | 36 | 37 | 38 | 39 | 40 |

| | | | | | | | | | CDR-H2 |
|---|---|---|---|---|---|---|---|---|---|
| H41 | H42 | H43 | H44 | H45 | H46 | H47 | H48 | H49 | H50 |
| P | G | K | E | R | E | F | L | A | A |
| 41 | 42 | 43 | 44 | 45 | 46 | 47 | 48 | 49 | 50 |

| CDR-H2 | | | | | | | | |
|---|---|---|---|---|---|---|---|---|
| H51 | H52 | H52A | H53 | H54 | H55 | H56 | H57 | H58 | H59 |
| I | G | W | S | G | A | V | T | H | Y |
| 51 | 52 | 53 | 54 | 55 | 56 | 57 | 58 | 59 | 60 |

| CDR-H2 | | | | | | | | | |
|---|---|---|---|---|---|---|---|---|---|
| H60 | H61 | H62 | H63 | H64 | H65 | H66 | H67 | H68 | H69 |
| S | D | S | V | K | G | R | F | T | I |
| 61 | 62 | 63 | 64 | 65 | 66 | 67 | 68 | 69 | 70 |

| H70 | H71 | H72 | H73 | H74 | H75 | H76 | H77 | H78 | H79 |
|---|---|---|---|---|---|---|---|---|---|
| S | R | D | N | A | K | N | T | V | Y |
| 71 | 72 | 73 | 74 | 75 | 76 | 77 | 78 | 79 | 80 |

| H80 | H81 | H82 | H82A | H82B | H82C | H83 | H84 | H85 | H86 |
|---|---|---|---|---|---|---|---|---|---|
| L | Q | M | N | S | L | R | A | E | D |
| 81 | 82 | 83 | 84 | 85 | 86 | 87 | 88 | 89 | 90 |

| | | | | | | | | CDR-H3 | |
|---|---|---|---|---|---|---|---|---|---|
| H87 | H88 | H89 | H90 | H91 | H92 | H93 | H94 | H95 | H96 |
| T | G | R | Y | Y | C | A | E | D | Y |
| 91 | 92 | 93 | 94 | 95 | 96 | 97 | 98 | 99 | 100 |

| CDR-H3 | | | | | | | | | |
|---|---|---|---|---|---|---|---|---|---|
| H97 | H98 | H99 | H100 | H100A | H101 | H102 | H103 | H104 | H105 |
| D | T | D | V | W | Q | Y | W | G | Q |
| 101 | 102 | 103 | 104 | 105 | 106 | 107 | 108 | 109 | 110 |

| H106 | H107 | H108 | H109 | H110 | H111 | H112 | H113 |
|---|---|---|---|---|---|---|---|
| G | T | Q | V | T | V | S | S |
| 111 | 112 | 113 | 114 | 115 | 116 | 117 | 118 |

The polypeptide sequence of V7R-2E9, a further a polypeptide of the invention, is provided below in Kabat format:

| H1 | H2 | H3 | H4 | H5 | H6 | H7 | H8 | H9 | H10 |
|---|---|---|---|---|---|---|---|---|---|
| E | V | Q | L | V | E | S | G | G | G |
| 1 | 2 | 3 | 4 | 5 | 6 | 7 | 8 | 9 | 10 |

| H11 | H12 | H13 | H14 | H15 | H16 | H17 | H18 | H19 | H20 |
|---|---|---|---|---|---|---|---|---|---|
| L | V | Q | A | G | G | S | L | R | L |
| 11 | 12 | 13 | 14 | 15 | 16 | 17 | 18 | 19 | 20 |

| H21 | H22 | H23 | H24 | H25 | H26 | H27 | H28 | H29 | H30 |
|---|---|---|---|---|---|---|---|---|---|
| S | C | E | S | S | I | S | T | F | S |
| 21 | 22 | 23 | 24 | 25 | 26 | 27 | 28 | 29 | 30 |

| | CDR-H1 | | | | | | | | |
|---|---|---|---|---|---|---|---|---|---|
| H31 | H32 | H33 | H34 | H35 | H36 | H37 | H38 | H39 | H40 |
| S 31 | D 32 | A 33 | M 34 | G 35 | W 36 | F 37 | R 38 | Q 39 | A 40 |

| H41 | H42 | H43 | H44 | H45 | H46 | H47 | H48 | H49 | CDR-H2 H50 |
|---|---|---|---|---|---|---|---|---|---|
| P 41 | G 42 | K 43 | E 44 | R 45 | E 46 | F 47 | L 48 | A 49 | A 50 |

| | | | CDR-H2 | | | | | | |
|---|---|---|---|---|---|---|---|---|---|
| H51 | H52 | H52A | H53 | H54 | H55 | H56 | H57 | H58 | H59 |
| I 51 | G 52 | W 53 | S 54 | G 55 | A 56 | V 57 | T 58 | H 59 | Y 60 |

| | | CDR-H2 | | | | | | | |
|---|---|---|---|---|---|---|---|---|---|
| H60 | H61 | H62 | H63 | H64 | H65 | H66 | H67 | H68 | H69 |
| S 61 | D 62 | S 63 | V 64 | Q 65 | G 66 | R 67 | F 68 | T 69 | I 70 |

| H70 | H71 | H72 | H73 | H74 | H75 | H76 | H77 | H78 | H79 |
|---|---|---|---|---|---|---|---|---|---|
| S 71 | R 72 | D 73 | N 74 | A 75 | K 76 | N 77 | T 78 | V 79 | Y 80 |

| H80 | H81 | H82 | H82A | H82B | H82C | H83 | H84 | H85 | H86 |
|---|---|---|---|---|---|---|---|---|---|
| L 81 | Q 82 | M 83 | N 84 | S 85 | L 86 | K 87 | S 88 | E 89 | D 90 |

| | | | | | | | | CDR-H3 | |
|---|---|---|---|---|---|---|---|---|---|
| H87 | H88 | H89 | H90 | H91 | H92 | H93 | H94 | H95 | H96 |
| T 91 | G 92 | R 93 | Y 94 | Y 95 | C 96 | A 97 | E 98 | D 99 | Y 100 |

| | | | CDR-H3 | | | | | | |
|---|---|---|---|---|---|---|---|---|---|
| H97 | H98 | H99 | H100 | H100A | H101 | H102 | H103 | H104 | H105 |
| D 101 | T 102 | D 103 | V 104 | W 105 | Q 106 | Y 107 | W 108 | G 109 | Q 110 |

| H106 | H107 | H108 | H109 | H110 | H111 | H112 | H113 |
|---|---|---|---|---|---|---|---|
| G 111 | T 112 | Q 113 | V 114 | T 115 | V 116 | S 117 | S 118 |

Residue numbering from N- to C-terminus is provided in the bottom row. Kabat numbering includes the 'H' prefix and is provided in the second row. CDR1, CDR2 and CDR3 are labelled as 'CDR-H1', 'CDR-H2' and 'CDR-H3', respectively.

The polypeptide sequences of further polypeptides of the invention (discussed under Examples 2 and 3) are aligned below (note that V7R-6C12 is referred-to as IL-7R-6C12 below):

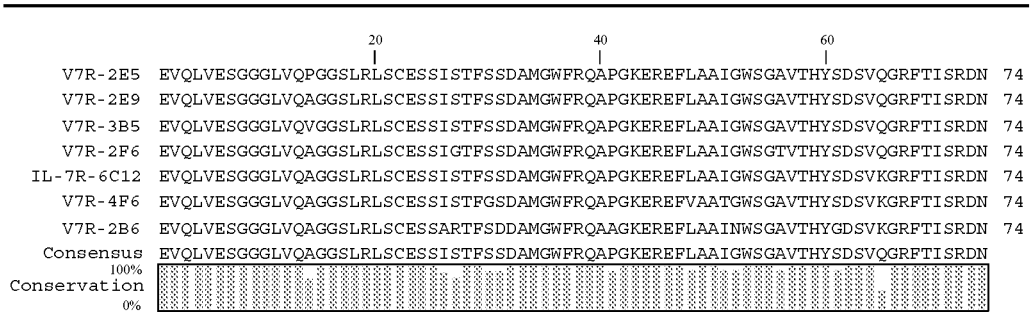

```
                       80         100
                        |          |
     V7R-2E5  AKNTVYLQMNSLKSEDTGRYYCAEDYDTDVWQYWGQGTQVTVSS  118
     V7R-2E9  AKNTVYLQMNSLKSEDTGRYYCAEDYDTDVWQYWGQGTQVTVSS  118
     V7R-3B5  AKNTVYLQMNSLKSEDTGRYYCAEDYDTDVWQYSGQGTQVTVSS  118
     V7R-2F6  AKNTVYLQMNSLKSEDTGRYYCAEDYDTDVWQYWGQGTQVTVSS  118
   IL-7R-6C12 AKNTVYLQMNSLKSEDTGRYYCAEDYVTDVWQYWGQGTQVTVSS  118
     V7R-4F6  AKNTVYLQMNSLKSEDTGTYYCAEDYDTDVWQYWGQGTQVTVSS  118
     V7R-2B6  AKNTVYLQMDSLKPEDTAVYYCAEDYDTDVWQHWGQGTQVTVSS  118
   Consensus  AKNTVYLQMNSLKSEDTGRYYCAEDYDTDVWQYWGDGTQVTVSS
         100%
Conservation
          0%
```

Suitably, the polynucleotides used in the present invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

In one aspect of the invention there is provided a polynucleotide encoding the polypeptide or construct of the invention. Suitably the polynucleotide comprises or consists of a sequence sharing 70% or greater, such as 80% or greater, such as 90% or greater, such as 95% or greater, such as 99% or greater sequence identity with SEQ ID NO: 69 or 70, most suitably SEQ ID NO: 70. More suitably the polynucleotide comprises or consists (most suitably consists) of either SEQ ID NO: 69 or 70, most suitably SEQ ID NO: 70. In a further aspect there is provided a cDNA comprising said polynucleotide.

In one aspect of the invention there is provided a polynucleotide comprising or consisting of a sequence sharing 70% or greater, such as 80% or greater, such as 90% or greater, such as 95% or greater, such as 99% or greater sequence identity with any one of the portions of either SEQ ID NO: 69 or 70 which encodes CDR1, CDR2 or CDR3 of the encoded immunoglobulin chain variable domain.

Suitably, the polypeptide sequence of the present invention contains at least one alteration with respect to a native sequence. Suitably, the polynucleotide sequences of the present invention contain at least one alteration with respect to a native sequence. Suitably the alteration to the polypeptide sequence or polynucleotide sequence is made to increase stability of the polypeptide or encoded polypeptide to proteases present in the intestinal tract (for example trypsin and chymotrypsin).

Possible features of the CDRs and frameworks of the polypeptide of the invention are described below.

CDR1

Suitably CDR1 of the polypeptide of the present invention comprises or more suitably consists of a sequence sharing 80% or greater sequence identity with SEQ ID NO: 1.

Alternatively, CDR1 of the polypeptide of the present invention comprises or more suitably consists of a sequence having no more than 2, more suitably no more than 1 addition(s) compared to SEQ ID NO: 1. Suitably, CDR1 of the polypeptide of the present invention comprises or more suitably consists of a sequence having no more than 2, more suitably no more than 1 substitution(s) compared to SEQ ID NO: 1. Suitably, CDR1 of the polypeptide of the present invention comprises or more suitably consists of a sequence having no more than 2, more suitably no more than 1 deletion(s) compared to SEQ ID NO: 1.

Suitably any residues of CDR1 differing from their corresponding residues in SEQ ID NO: 1 are conservative substitutions with respect to their corresponding residues.

Suitably the residues of CDR1 have the following identities (SEQ ID NO: 82):

| 1   | 2 | 3 | 4 | 5 |
| --- | - | - | - | - |
| S/D | D | A | M | G |

Suitably CDR1 comprises or consists of SEQ ID NO: 1 or SEQ ID NO: 71. More suitably CDR1 comprises or more suitably consists of SEQ ID NO: 1.

CDR2

Suitably CDR2 of the polypeptide of the present invention comprises or more suitably consists of a sequence sharing 65% or greater, 75% or greater, 80% or greater, 85% or greater or 90% or greater sequence identity, with SEQ ID NO: 2.

Alternatively, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 2. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 2. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 2.

Suitably any residues of CDR2 differing from their corresponding residues in SEQ ID NO: 2 are conservative substitutions with respect to their corresponding residues.

Suitably the residues of CDR2 have the following identities (SEQ ID NO: 83):

| 1 | 2 | 3 | 4 | 5 | 6 | 7 | 8 | 9 | 10 | 11 | 12 | 13 | 14 | 15 | 16 | 17 |
|---|---|---|---|---|---|---|---|---|----|----|----|----|----|----|----|----|
| A | I/T | G/N | W | S | G | A/T | V | T | H | Y | S/G | D | S | V | Q/K | G |

Suitably the residue of CDR2 corresponding to residue number 16 of SEQ ID NO: 2 is Q or K, most suitably K. Suitably CDR2 comprises or consists of SEQ ID NO: 2, SEQ ID NO: 72, SEQ ID NO: 73, SEQ ID NO: 74, SEQ ID NO: 75 or SEQ ID NO: 76. More suitably CDR2 comprises or more suitably consists of SEQ ID NO: 2.

CDR3

Suitably CDR3 of the polypeptide of the present invention comprises or more suitably consists of a sequence sharing 60% or greater, 70% or greater or 80% or greater sequence identity with SEQ ID NO: 3.

Alternatively, CDR3 of the polypeptide of the present invention comprises or more suitably consists of a sequence having no more than 3, more suitably no more than 2, more suitably no more than 1 addition(s) compared to SEQ ID NO: 3. Suitably, CDR3 of the polypeptide of the present invention comprises or more suitably consists of a sequence having no more than 3, more suitably no more than 2, more suitably no more than 1 substitution(s) compared to SEQ ID NO: 3. Suitably, CDR3 of the polypeptide of the present invention comprises or more suitably consists of a sequence having no more than 3, more suitably no more than 2, more suitably no more than 1 deletion(s) compared to SEQ ID NO: 3. Suitably, any substitutions are conservative, with respect to their corresponding residues in SEQ ID NO: 3.

Suitably any residues of CDR3 differing from their corresponding residues in SEQ ID NO: 3 are conservative substitutions with respect to their corresponding residues.

Suitably the residues of CDR3 have the following identities (SEQ ID NO: 84):

| 1 | 2 | 3 | 4 | 5 | 6 | 7 | 8 | 9 |
|---|---|---|---|---|---|---|---|---|
| D | Y | D/V | T | D | V | W | Q | Y/H |

Suitably the sequence of CDR3 comprises or consists of SEQ ID NO: 3, SEQ ID NO: 77 or SEQ ID NO: 78. More suitably CDR3 comprises or more suitably consists of SEQ ID NO: 3.

Particular CDRs

Some particularly suitable CDR sequences are shown in the table below. Suitably, CDR1 of the polypeptide of the invention is one of the CDR1 sequences listed below. Suitably, CDR2 of the polypeptide of the invention is one of the CDR2 sequences listed below. Suitably, CDR3 of the polypeptide of the invention is one of the CDR3 sequences listed below. Suitably, the polypeptide of the invention comprises a combination of two, or more suitably three, of the CDR sequences listed below.

Particular CDRs of the polypeptide of the invention are provided below. 'Example' denotes an exemplary ICVD comprising that CDR and the corresponding sequence identifier number for that sequence.

| SEQ ID NO | CDR1 | Example |
|---|---|---|
| 1 | SDAMG | ID-A62U |
| 71 | DDAMG | V7R-2B6 |

-continued

| SEQ ID NO | CDR2 | Example |
|---|---|---|
| 72 | AIGWSGAVTHYSDSVQG | V7R-2E9 |
| 73 | AIGWSGTVTHYSDSVQG | V7R-2F6 |
| 2 | AIGWSGAVTHYSDSVKG | ID-A62U |
| 74 | ATGWSGAVTHYSDSVKG | V7R-4F6 |
| 75 | AINWSGAVTHYGDSVKG | V7R-2B6 |
| 76 | AIGWSGAVTHYSDSVKG | ID-A14U |

| SEQ ID NO | CDR3 | Example |
|---|---|---|
| 3 | DYDTDVWQY | ID-A62U |
| 77 | DYVTDVWQY | V7R-6C12 |
| 78 | DYDTDVWQH | V7R-2B6 |

FR1

Suitably FR1 of the polypeptide of the present invention comprises or more suitably consists of a sequence sharing 5%, 12%, 18%, 26%, 32%, 38%, 46%, 52%, 58%, 62%, 66%, 68%, 72%, 75%, 78%, 82%, 85%, 90%, 95% or greater sequence identity, with SEQ ID NO: 4.

Alternatively, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 4. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 4. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 4.

Suitably any residues of FR1 differing from their corresponding residues in SEQ ID NO: 4 are conservative substitutions with respect to their corresponding residues. Suitably the residue of FR1 corresponding to residue number 1 of SEQ ID NO: 4 is D or E, most suitably D. Suitably the residues of FR1 corresponding to residue numbers 1 to 5 of SEQ ID NO: 4 are DVQLV. Suitably FR1 comprises or more suitably consists of SEQ ID NO: 4. Suitably the residue of FR1 corresponding to residue number 24 of SEQ ID NO: 4 is S.

FR2

Suitably FR2 of the polypeptide of the present invention comprises or more suitably consists of a sequence sharing 10%, 15%, 25%, 30%, 40%, 45%, 55%, 60%, 70%, 75%, 85%, 90% or greater sequence identity, with SEQ ID NO: 5.

Alternatively, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 5. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 5. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 5.

Suitably any residues of FR2 differing from their corresponding residues in SEQ ID NO: 5 are conservative substitutions with respect to their corresponding residues. Suitably the residue of FR2 corresponding to residue number 10 of SEQ ID NO: 5 is R or L, most suitably L. Suitably the residues of FR2 corresponding to residue numbers 8 to 11 of SEQ ID NO: 5 are KEXE, wherein X is R or L, most suitably L. Alternatively the residues of FR2 corresponding to residue numbers 9 to 12 of SEQ ID NO: 5 are CLEW. Suitably FR2 comprises or more suitably consists of SEQ ID NO: 5. Suitably the residue of FR2 corresponding to residue number 2 of SEQ ID NO: 5 is F, more suitably, in addition, the residue of FR2 corresponding to residue number 14 of SEQ ID NO: 5 is A. Suitably the residues of FR2 corresponding to residues 9-14 of SEQ ID NO: 5 are ELEFLA (SEQ ID NO: 79). Suitably the residues of FR2 corresponding to residues 9-14 of SEQ ID NO: 5 are not GLEWVS (SEQ ID NO: 80). Suitably the residue of FR2 corresponding to residue number 9 of SEQ ID NO: 5 is not G. More suitably the residue of FR2 corresponding to residue number 9 of SEQ ID NO: 5 is E.

FR3

Suitably FR3 of the polypeptide of the present invention comprises or more suitably consists of a sequence sharing 8%, 15%, 20%, 26%, 32%, 40%, 45%, 52%, 58%, 65%, 70%, 76%, 80%, 82%, 85%, 90%, 92%, 95% or greater sequence identity, with SEQ ID NO: 6.

Alternatively, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 addition(s) compared to SEQ ID NO: 6. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 6. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 6.

Suitably any residues of FR3 differing from their corresponding residues in SEQ ID NO: 6 are conservative substitutions with respect to their corresponding residues. Suitably FR3 comprises or more suitably consists of SEQ ID NO: 6. Suitably the residues of FR3 corresponding to residue numbers 18, 19 and 20 of SEQ ID NO: 6 are NSL. Suitably the residue of FR3 corresponding to residue number 21 of SEQ ID NO: 6 is R. Suitably the residue of FR3 corresponding to residue number 22 of SEQ ID NO: 6 is A.

FR4

Suitably FR4 of the polypeptide of the present invention comprises or more suitably consists of a sequence sharing 5%, 10%, 20%, 30%, 40%, 50%, 60%, 70%, 80%, 90% or greater sequence identity, with SEQ ID NO: 7.

Alternatively, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 7. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 7. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 7.

Suitably any residues of FR4 differing from their corresponding residues in SEQ ID NO: 7 are conservative substitutions with respect to their corresponding residues. Suitably FR4 comprises or more suitably consists of SEQ ID NO: 7.

The Entire Polypeptide

Suitably the polypeptide of the present invention comprises or more suitably consists of a sequence sharing 50%, 55%, 60%, 65%, 70%, 75%, 80%, 85%, 90%, 95%, 96%, 97%, 98%, 99% or greater sequence identity, with SEQ ID NO: 8.

Alternatively, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 8. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 8. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 8.

Suitably the N-terminus of the polypeptide is D. Suitably the polypeptide comprises or more suitably consists of SEQ ID NO: 8.

Framework Embodiments

In one aspect of the invention there is provided a polypeptide comprising four framework regions (FR1-FR4), wherein each framework region is a variant of a corresponding framework region of ID-A62U (i.e. SEQ ID NO: 4, SEQ ID NO: 5, SEQ ID NO: 6 and SEQ ID NO: 7). Suitably each variant framework region shares at least 50%, more suitably at least 60%, more suitably at least 70%, more suitably at least 80% or more suitably at least 90% identity with its corresponding framework region in ID-A62U. More suitably the variant framework regions comprise or more suitably consist of the corresponding framework regions of ID-A62U. Suitably the polypeptide comprising four framework regions is an antibody or an antibody fragment. Suitably the antibody fragment is a VHH, a VH, a VL, a V-NAR, an scFv, a Fab fragment, or a F(ab')2 fragment. More suitably the antibody fragment is a VHH or VH, and most suitably a VHH.

Epitopes

Example 5 details epitope modelling work performed on a polypeptide of the invention, V7R-2E9. This work indicates that V7R-2E9 binds to the following residues of IL-7Rα. The residues which bury a particularly significant area at the interface are highlighted in bold.

Residue numbering corresponds to SEQ ID NO: 65.

| Residue | Number | BSA (as % of ASA) |
|---|---|---|
| GLU | 27 | 5.8 |
| SER | 31 | 54.9 |
| LEU | 57 | 20.4 |
| VAL | 58 | 80.5 |
| GLU | 59 | 7.1 |
| LYS* | 77 | 22.8 |
| LYS | 78 | 8.4 |
| PHE | 79 | 63.3 |
| LEU | 80 | 78.6 |
| LEU | 81 | 64.0 |
| ILE | 82 | 69.6 |
| THR | 104 | 10.9 |
| LYS | 137 | 3.3 |
| LYS* | 138 | 78.5 |
| TYR* | 139 | 69.4 |
| LYS | 141 | 0.9 |
| HIS | 191 | 14.4 |
| TYR | 192 | 41.1 |
| PHE | 193 | 53.4 |

BSA is surface area buried at the interface.
ASA is surface area before complex forms
*form H-bonds Accordingly, in one aspect of the invention there is provided a polypeptide which binds to an epitope on IL-7Rα (SEQ ID NO: 65) comprising at least one residue of IL-7Rα selected from the list consisting of Glu27, Ser31, Leu57, Val58, Glu59, Lys77, Lys78, Phe79, Leu80, Leu81, Ile82, Thr104, Lys137, Lys138, Tyr139, Lys141, His191, Tyr192 and Phe193. Suitably, the polypeptide binds to an epitope on IL-7Rα comprising at least 8, more suitably at least 15, more suitably at least all residues of IL-7Rα selected from this list.

It may be noted that certain residues of IL-7Rα bury a particularly significant area at the interface with V7R-2E9. Accordingly, in a further aspect of the invention, there is provided a polypeptide which binds to an epitope on IL-7Rα (SEQ ID NO: 65) comprising at least one residue of IL-7Rα selected from the list consisting of Ser31, Val58, Phe79, Leu80, Leu81, Ile82, Lys138, Tyr139 and Phe193. Suitably, the polypeptide binds to an epitope on IL-7Rα comprising at least Val58, Leu80 and Lys138 of IL-7Rα. More suitably Val58, Leu80, Lys138, Ile82 and Tyr139 of IL-7Rα. More suitably Val58, Leu80, Lys138, Ile82, Tyr139, Leu81 and Phe79 of IL-7Rα. Suitably, the polypeptide binds to an epitope on IL-7Rα comprising at least 5, more suitably at least 7, more suitably all residues of IL-7Rα selected from Ser31, Val58, Phe79, Leu80, Leu81, Ile82, Lys138, Tyr139 and Phe193.

Suitably, 'binds to an epitope' in this context may be defined as the relevant residues of IL-7Rα making up the epitope, upon the polypeptide binding, having a BSA of at least that recited in the table above in respect of the relevant residue.

Linkers and Multimers

A construct according to the invention comprises multiple polypeptides and therefore may suitably be multivalent. Such a construct may comprise at least two identical polypeptides according to the invention. A construct consisting of two identical polypeptides according to the invention is a "homobihead". In one aspect of the invention there is provided a construct comprising two or more identical polypeptides of the invention.

Alternatively, a construct may comprise at least two polypeptides which are different, but are both still polypeptides according to the invention (a "heterobihead").

Alternatively, such a construct may comprise (a) at least one polypeptide according to the invention and (b) at least one polypeptide such as an antibody or antigen-binding fragment thereof, which is not a polypeptide of the invention (also a "heterobihead"). The at least one polypeptide of (b) may bind IL-7R (for example via a different epitope to that of (a)), or alternatively may bind to a target other than IL-7R. Suitably the different polypeptide (b) binds to, for example: an interleukin (such as IL-1, IL-1ra, IL-4, IL-5, IL-6, IL-7, IL-8, IL-9, IL-10, IL-11, IL-12, IL-13, IL-15, IL-17 and IL-18), an interleukin receptor (such as IL-6R), a transcription factor (such as NF-kB), a cytokine (such as TNF-alpha, IFN-gamma TGF-beta), a transmembrane protein (such as gp130 and CD3), a surface glycoprotein (such as CD4, CD20, CD40), a soluble protein (such as CD40L), an integrin (such as a4b7 and AlphaEbeta7), an adhesion molecule (such as MAdCAM), a chemokine (such as IP10 and CCL20), a chemokine receptor (such as CCR2 and CCR9), an inhibitory protein (such as SMAD7), a kinase (such as JAK3), a G protein-coupled receptor (such as sphingosine-1-P receptor), other inflammatory mediators or immunologically relevant ligands involved in human pathological processes. Thus the different polypeptide (b) binds to, for example, IL-6R, IL-6, IL-12, IL-1-beta, IL-17A, TNF-alpha or CD3; or other inflammatory mediators or immunologically relevant ligands involved in human pathological processes.

Constructs can be multivalent and/or multispecific. A multivalent construct (such as a bivalent construct) comprises two or more binding polypeptides therefore presents two or more sites at which attachment to one or more antigens can occur. An example of a multivalent construct could be a homobihead or a heterobihead. A multispecific construct (such as a bispecific construct) comprises two or more different binding polypeptides which present two or more sites at which either (a) attachment to two or more different antigens can occur or (b) attachment to two or more different epitopes on the same antigen can occur. An example of a multispecific construct could be a heterobihead. A multispecific construct is multivalent.

Suitably, the polypeptides comprised within the construct are antibody fragments. More suitably, the polypeptides comprised within the construct are selected from the list consisting of: VHH, a VH, a VL, a V-NAR, an scFv, a Fab fragment, or a F(ab')2 fragment. More suitably, the polypeptides comprised within the construct are VHs or VHHs, most suitably VHHs.

Suitably, the polypeptides comprised within the construct are selected from the list consisting of: an ICVD (such as a VHH, a VH, a VL), a V-NAR, an scFv, a Fab fragment, or a F(ab')2 fragment. More suitably, the polypeptide comprised within the construct are ICVDs, more suitably, the polypeptides comprised within the construct are VHs or VHHs, most suitably VHHs.

The polypeptides of the invention can be linked to each other directly (i.e. without use of a linker) or via a linker. Suitably, the linker is a protease-labile or a non-protease-labile linker. The linker is suitably a polypeptide and will be selected so as to allow binding of the polypeptides to their epitopes. If used for therapeutic purposes, the linker is suitably non-immunogenic in the subject to which the polypeptides are administered. Suitably the polypeptides are all connected by non-protease-labile linkers. Suitably the protease-labile linker is of the format $[-(G_aS)_x-BJB'-(G_aS)_y-]_z$ wherein J is lysine or arginine, B is 0 to 5 amino acid residues selected from R, H, N, Q, S, T, Y, G, A, V, L, W, P, M, C, F, K or I, B' is 0 to 5 amino acid residues selected from R, H, N, Q, S, T, Y, G, A, V, L, W, M, C, F, K or I, a is 1 to 10, x is 1 to 10; y is 1 to 10 and z is 1 to 10 (SEQ ID NO: 85). Suitably a is 4. Most suitably a is 4, J is lysine, B is 0 x is 1, y is 1 and z is 1. Alternatively the protease-labile linker is of the format $-(G_4S)_x-K-(G_4S)_y-$ wherein x and y are each independently 1 to 5 (SEQ ID NO: 86), more suitably $-(G_4S)_2-K-(G_4S)_2-$ (SEQ ID NO: 87).

Suitably the non-protease-labile linkers are of the format $(G_4S)_x$ (SEQ ID NO: 88). More suitably x is 1 to 10, more suitably x is 4 to 8, more suitably x is 4, 6 or 8. Most suitably x is 6 (SEQ ID NO: 89).

Vectors and Hosts

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g. replication defective retroviruses, adenoviruses and adeno-associated viruses), which serve equivalent functions, and also bacteriophage and phagemid systems. The invention also relates to nucleotide sequences that encode polypeptide sequences or multivalent and/or multispecific constructs. The term "recombinant host cell" (or simply "host cell"), as used herein, is intended to refer to a cell into which a recombinant expression vector has been introduced. Such terms are intended to refer not only to the particular subject cell but to the progeny of such a cell.

In one aspect of the invention there is provided a vector comprising the polynucleotide encoding the polypeptide or construct of the invention or cDNA comprising said polynucleotide. In a further aspect of the invention there is provided a host cell transformed with said vector, which is capable of expressing the polypeptide or construct of the invention. Suitably the host cell is a bacterium such as *Escherchia coli*, a yeast belonging to the genera *Aspergillus, Saccharomyces, Kluyveromyces, Hansenula* or *Pichia*, such as *Saccharomyces cerevisiae* or *Pichia pastoris*.

Autoimmune Diseases and/or Inflammatory Diseases

Autoimmune diseases develop when the immune system responds adversely to normal body tissues. Autoimmune disorders may result in damage to body tissues, abnormal organ growth and/or changes in organ function. The disorder may affect only one organ or tissue type or may affect multiple organs and tissues. Organs and tissues commonly affected by autoimmune disorders include blood components such as red blood cells, blood vessels, connective tissues, endocrine glands such as the thyroid or pancreas, muscles, joints and skin. An inflammatory disease is a disease characterised by inflammation. Many inflammatory diseases are autoimmune diseases and vice-versa.

Suitably the polypeptide, pharmaceutical composition or construct of the invention is for use as a medicament and more suitably for use in the treatment of an autoimmune and/or inflammatory disease.

The polypeptide of the invention (suitably, when orally delivered) will ideally treat inflammatory diseases where IL-7 and/or L-TSLP contributes to at least a proportion of the pathology and the polypeptide can access the tissue where the IL-7 and/or L-TSLP is biologically active.

The polypeptide of the invention binds to a receptor (IL-7R). It may therefore also disrupt an as-yet undiscovered cytokine or other binding partner of IL-7R that could be involved in disease.

Inhibition of IL-7 and L-TSLP Binding IL-7R

Evidence that the different isoforms of TSLP are differentially expressed and act via different signalling pathways, has suggested that it might be possible to selectively target the disease related activities of L-TSLP, rather than the physiologically beneficial effects of the short isoform of this cytokine. Polypeptides of the invention inhibit the binding of IL-7 to the IL-7R. Information from modelling in silico of the V7R-2E9 molecule interaction with IL-7Rα and a structure published recently of the TSLP:TSLPR:IL-7R complex (Verstraete et al 2017) has strongly suggested that V7R-2E9 and other polypeptides of the invention would inhibit the binding of both IL-7 and L-TSLP to the IL-7Rα. The ability of V7R-2E9 to potently block the receptor-binding and cell-based biological activities of both IL-7 (IL-7-induced STAT5 phosphorylation) and L-TSLP (TSLP-induced TARC secretion) has now been confirmed. Since V7R-2E9 binds to the IL-7Rα rather than to TSLP, it is expected that V7R-2E9 and related ICVDs will block only the pro-inflammatory activities of L-TSLP and that the important mucosal homeostatic functions of S-TSLP will not be affected.

Inflammatory Bowel Disease (IBD)

The chronic inflammatory bowel diseases Crohn's disease and ulcerative colitis, which afflict both children and adults, are examples of autoimmune and inflammatory diseases of the GIT (Hendrickson et al 2002). Ulcerative colitis is defined as a condition where the inflammatory response and morphologic changes remain confined to the colon. The rectum is involved in 95% of patients. Inflammation is largely limited to the mucosa and consists of continuous involvement of variable severity with ulceration, edema, and hemorrhage along the length of the colon (Hendrickson et al 2002). Ulcerative colitis is usually manifested by the presence of blood and mucus mixed with stool, along with lower abdominal cramping which is most severe during the passage of bowel movements. Clinically, the presence of diarrhoea with blood and mucus differentiates ulcerative colitis from irritable bowel syndrome, in which blood is absent. Unlike ulcerative colitis, the presentation of Crohn's disease is usually subtle, which leads to a later diagnosis. Factors such as the location, extent, and severity of involvement determine the extent of gastrointestinal symptoms. Patients who have ileocolonic involvement usually have postprandial abdominal pain, with tenderness in the right lower quadrant and an occasional inflammatory mass. Symptoms associated with gastroduodenal Crohn's disease include early satiety, nausea, emesis, epigastric pain, or dysphagia. Perianal disease is common, along with anal tags, deep anal fissures, and fistulae (Hendrickson et al 2002).

Suitably the polypeptide, pharmaceutical composition or construct of the invention is used in the treatment of an autoimmune and/or inflammatory disease of the GI (gastrointestinal) tract where IL-7 and/or L-TSLP contributes to the pathology of such disease.

Suitably the polypeptide, pharmaceutical composition or construct of the invention is for use in the treatment of an autoimmune and/or inflammatory disease of the GI tract selected from the list consisting of Crohn's disease, ulcerative colitis, irritable bowel disease, diabetes type II, glomerulonephritis, autoimmune hepatitis, Sjogren's syndrome, celiac disease and drug- or radiation-induced mucositis (more suitably Crohn's disease or ulcerative colitis, most suitably ulcerative colitis).

Eosinophilic Esophagitis (EoE)

Eosinophilic esophagitis (EoE, also spelled eosinophilic oesophagitis and also known as allergic oesophagitis), is an allergic inflammatory condition of the esophagus that involves eosinophils, a type of white blood cell. Symptoms are swallowing difficulty, food impaction, vomiting, and heartburn.

Suitably the polypeptide, pharmaceutical composition or construct of the invention is for use in the treatment of eosinophilic esophagitis. More suitably the polypeptide, pharmaceutical composition or construct is for use in the treatment of eosinophilic esophagitis and is administered orally.

Other Autoimmune/Inflammatory Diseases

Other diseases of the GIT which may be treated for example via oral administration of a polypeptide of the invention include for example the inflammatory disease mucositis (suitably drug- and radiation induced-mucositis), asthma, idiopathic pulmonary fibrosis, atopic dermatitis, allergic conjunctivitis, allergic rhinitis, Netherton syndrome, food allergy, allergic diarrhoea, eosinophilic gastroenteritis, allergic bronchopulmonary aspergillosis (ABPA), allergic fungal sinusitis, cancer, COPD, keloids, chronic rhinosinusitis (CRS), nasal polyposis, chronic eosinophilic pneumonia, eosinophilic bronchitis, coeliac disease and Churg-Strauss syndrome.

In mucositis the lesions can occur anywhere from mouth to anus and for mouth and oesophagus lesions a mouthwash or cream preparation containing the variable domain may be used. For anal and rectal lesions, suppositories, creams or foams containing the variable domain would be suitable for topical application. The immunoglobulin chain variable domains will be cleared from the lamina propria or other inflammatory sites via absorption into the bloodstream at sites of inflammation or via lymphatic clearance and subsequent entry into the bloodstream. The domains will therefore reach the liver via the bloodstream and will be cleared via glomerular filtration in the kidney. There is therefore good rationale that the domains will function therapeutically in diseases such as autoimmune hepatitis, type II diabetes and glomerular nephritis.

In one embodiment the polypeptide or construct of the invention is for use in the treatment or prevention of atopic dermatitis, suitably by topical delivery to and/or through the skin, suitably in the form of a cream, nanoparticles, ointment or hydrogel.

Suitably the polypeptide, pharmaceutical composition or construct is for use in the treatment of other autoimmune/inflammatory diseases in which IL-7 and/or L-TSLP is responsible for a proportion of the pathology observed.

Therapeutic Use and Delivery

A therapeutically effective amount of a polypeptide, pharmaceutical composition or construct of the invention, is an amount which is effective, upon single or multiple dose administration to a subject, in inhibiting IL-7 and/or L-TSLP from binding IL-7R to a significant extent in a subject. A therapeutically effective amount may vary according to factors such as the disease state, age, sex, and weight of the individual, and the ability of the polypeptide, pharmaceutical composition or construct to elicit a desired response in the individual. A therapeutically effective amount is also one in which any toxic or detrimental effects of the polypeptide of the invention, pharmaceutical composition or construct are outweighed by the therapeutically beneficial effects. The polypeptide or construct of the invention can be incorporated into pharmaceutical compositions suitable for administration to a subject. The polypeptide or construct of the invention can be in the form of a pharmaceutically acceptable salt.

A pharmaceutical composition of the invention may suitably be formulated for oral, intramuscular, subcutaneous or intravenous delivery. The pharmaceutical compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. Solid dosage forms are preferred. The polypeptide of the invention, pharmaceutical composition or construct may be incorporated with excipients and used in the form of ingestible tablets, buccal tablets, troches, capsules, elixirs, suspensions, syrups, wafers, and the like. For the treatment of eosinophilic esophagitis, delivery in the form of a lozenge is particularly preferred. For the treatment of atopic dermatitis, delivery in the form of a cream is particularly preferred.

Typically, the pharmaceutical composition comprises a polypeptide or construct of the invention and a pharmaceutically acceptable diluent or carrier. Examples of pharmaceutically acceptable carriers include one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the polypeptide or construct of the invention. Pharmaceutical compositions may include antiadherents, binders, coatings, disintegrants, flavours, colours, lubricants, sorbents, preservatives, sweeteners, freeze dry excipients (including lyoprotectants) or compression aids.

In patients with EoE and UC, the inflamed intestinal mucosal epithelial barrier is thought to be impaired and consequently the penetration of an orally administered polypeptide of the invention into the underlying mucosal tissue would be facilitated, potentially resulting in the inhibition of both IL-7 and L-TSLP activity in the target tissue at sites of inflammation. Orally administering the polypeptide of the invention should limit systemic inhibition of IL-7 and L-TSLP activity reducing the risks of general immunosuppression that are associated with conventional IL-7 and TSLP antibodies that are given by injection. It is possible that a short period of anti-IL-7R antibody treatment, such as occurs in animal models, will provide an extended period of clinical effect (remission) due to the depletion of pathogenic T cells. However, the repeated systemic administration of existing IL-7Rα-blocking antibodies to patients is likely to result in the inhibition of thymic T cell development and depletion of T cells in the periphery resulting in significant systemic immunosuppression. Inflammatory bowel diseases (Crohn's disease and ulcerative colitis) and EoE are largely localised to the gastrointestinal tract; consequently, the oral administration of a polypeptide of the invention to the inflamed intestinal mucosa offers the potential to achieve a localised effect with limited systemic exposure thereby reducing the risk of immunosuppression in tissues not affected by disease.

Accordingly, the polypeptide, pharmaceutical composition or construct of the invention is suitably administered orally. The polypeptide, pharmaceutical composition or construct may be delivered orally (such as for the treatment of EoE) to the buccal cavity, pharynx and esophagus (more suitably the esophagus) or may be delivered orally (such as for the treatment of IBD) to the duodenum, jejunum, ileum, cecum, colon, rectum and/or anal canal.

A key problem with oral delivery is ensuring that sufficient polypeptide, pharmaceutical composition or construct reaches the area of the intestinal tract where it is required. Factors which prevent a polypeptide, pharmaceutical composition or construct of the invention reaching the area of the intestinal tract where it is required include the presence of proteases in digestive secretions which may degrade a polypeptide, pharmaceutical composition or construct of the invention. Suitably, the polypeptide, pharmaceutical composition or construct of the invention are substantially stable in the presence of one or more of such proteases by virtue of the inherent properties of the polypeptide or construct itself. Suitably, the polypeptide or construct of the invention is lyophilised before being incorporated into a pharmaceutical composition.

A polypeptide of the invention may also be provided with an enteric coating. An enteric coating is a polymer barrier applied on oral medication which helps to protect the polypeptide from the low pH of the stomach. Materials used for enteric coatings include fatty acids, waxes, shellac, plastics, and plant fibers. Suitable enteric coating components include methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid. Suitable enteric coatings include pH-dependent release polymers. These are polymers which are insoluble at the highly acidic pH found in the stomach, but which dissolve rapidly at a less acidic pH. Thus, suitably, the enteric coating will not dissolve in the acidic juices of the stomach (pH—3), but will do so in the higher pH environment present in the small intestine (pH above 6) or in the colon (pH above 7.0). The pH-dependent release polymer is selected such that the polypeptide or construct of the invention will be released at about the time that the dosage reaches the small intestine.

If administered orally for the treatment of IBD, the polypeptide of the invention is suitably provided with an enteric coating. If administered orally for the treatment of EoE, the polypeptide of the invention is suitably provided in the form of a compressed troche.

A polypeptide, construct or pharmaceutical composition of the invention may be delivered topically. Such a pharmaceutical composition may suitably be in the form of a cream, ointment, lotion, gel, foam, transdermal patch, powder, paste or tincture and may suitably include vitamin D3 analogues (e.g calcipotriol and maxacalcitol), steroids (e.g. fluticasone propionate, betamethasone valerate and clobetasol propionate), retinoids (e.g. tazarotene), coal tar and dithranol. Topical medicaments are often used in combination with each other (e.g. a vitamin D3 and a steroid) or with further agents such as salicylic acid.

A polypeptide, construct or pharmaceutical composition of the invention can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilisers, isotonic agents, suspending agents, emulsifying agents, stabilisers and preservatives. Acceptable carriers, excipients and/or stabilisers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as polysorbates, POE ethers, poloxamers, Triton-X, or polyethylene glycol.

For all modes of delivery, the polypeptide, pharmaceutical composition or construct of the invention may be formulated in a buffer, in order to stabilise the pH of the composition, at a concentration between 5-50, or more suitably 15-40 or more suitably 25-30 g/litre. Examples of suitable buffer components include physiological salts such as sodium citrate and/or citric acid. Suitably buffers contain 100-200, more suitably 125-175 mM physiological salts such as sodium chloride. Suitably the buffer is selected to have a pKa close to the pH of the composition or the physiological pH of the patient.

Exemplary polypeptide or construct concentrations in a pharmaceutical composition may range from about 1 mg/mL to about 200 mg/ml or from about 50 mg/mL to about 200 mg/mL, or from about 150 mg/mL to about 200 mg/mL.

An aqueous formulation of the polypeptide, construct or pharmaceutical composition of the invention may be prepared in a pH-buffered solution, e.g., at pH ranging from about 4.0 to about 7.0, or from about 5.0 to about 6.0, or alternatively about 5.5. Examples of suitable buffers include phosphate-, histidine-, citrate-, succinate-, acetate-buffers and other organic acid buffers. The buffer concentration can be from about 1 mM to about 100 mM, or from about 5 mM to about 50 mM, depending, for example, on the buffer and the desired tonicity of the formulation.

The tonicity of the pharmaceutical composition may be altered by including a tonicity modifier. Such tonicity modifiers can be charged or uncharged chemical species. Typical uncharged tonicity modifiers include sugars or sugar alcohols or other polyols, preferably trehalose, sucrose, mannitol, glycerol, 1,2-propanediol, raffinose, sorbitol or lactitol (especially trehalose, mannitol, glycerol or 1,2-propanediol). Typical charged tonicity modifiers include salts such as a combination of sodium, potassium or calcium ions, with chloride, sulfate, carbonate, sulfite, nitrate, lactate, succinate, acetate or maleate ions (especially sodium chloride or sodium sulphate); or amino acids such as arginine or histidine. Suitably, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 1 mM to 500 nM. Suitably, at least one isotonic agent is included in the composition.

A surfactant may also be added to the pharmaceutical composition to reduce aggregation of the formulated polypeptide or construct and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, and polysorbate 80. Exemplary concentrations of surfactant may range from about 0.001% to about 10% w/v.

A lyoprotectant may also be added in order to protect the polypeptide or construct of the invention against destabilizing conditions during the lyophilization process. For example, known lyoprotectants include sugars (including glucose, sucrose, mannose and trehalose); polyols (including mannitol, sorbitol and glycerol); and amino acids (including alanine, glycine and glutamic acid). Lyoprotectants can be included in an amount of about 10 mM to 500 mM.

The dosage ranges for administration of the polypeptide of the invention, pharmaceutical composition or construct of the invention are those to produce the desired therapeutic effect. The dosage range required depends on the precise nature of the polypeptide of the invention, pharmaceutical composition or construct, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages of the polypeptide of the invention, pharmaceutical composition or construct of the invention are in the range of 50 ng-50 mg per kg, such as 50 ug-40 mg per kg, such as 5-30 mg per kg of body weight. The unit dosage can vary from less than 100 mg, but typically will be in the region of 250-2000 mg per dose, which may be administered daily or more frequently, for example 2, 3 or 4 times per day or less frequently for example every other day or once per week, once per fortnight or once per month.

In one aspect of the invention there is provided the use of the polypeptide, pharmaceutical composition or construct of the invention in the manufacture of a medicament for the treatment of autoimmune disease. In a further aspect of the invention there is provided a method of treating autoimmune disease comprising administering to a person in need thereof a therapeutically effective amount of the polypeptide, pharmaceutical composition or construct of the invention.

In one aspect of the invention there is provided the use of the polypeptide, pharmaceutical composition or construct of the invention in the manufacture of a medicament for the treatment of autoimmune and/or inflammatory disease. In a further aspect of the invention there is provided a method of treating autoimmune and/or inflammatory disease comprising administering to a person in need thereof a therapeutically effective amount of the polypeptide, pharmaceutical composition or construct of the invention.

The word 'treatment' is intended to embrace prophylaxis as well as therapeutic treatment. Treatment of diseases also embraces treatment of exacerbations thereof and also embraces treatment of patients in remission from disease symptoms to prevent relapse of disease symptoms.

Combination Therapy

A pharmaceutical composition of the invention may also comprise one or more active agents (e.g. active agents suitable for treating the diseases mentioned herein). It is within the scope of the invention to use the pharmaceutical composition of the invention in therapeutic methods for the treatment of autoimmune diseases as an adjunct to, or in conjunction with, other established therapies normally used in the treatment of autoimmune diseases.

For the treatment of IBD (such as Crohn's disease or ulcerative colitis), possible combinations include combinations with, for example, one or more active agents selected from the list comprising: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, methotrexate, azathioprine or 6-mercaptopurine); anti-TNF-alpha antibodies (e.g., infliximab, adalimumab, certolizumab pegol or golimumab); anti-IL12/1L23 antibodies (e.g., ustekinumab); anti-IL6R antibodies or small molecule IL12/1L23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK3 inhibitors (e.g., tofacitinib or R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071). The most suitable combination agents are infliximab, adalimumab, certolizumab pegol or golimumab.

Hence another aspect of the invention provides a pharmaceutical composition of the invention in combination with one or more further active agents, for example one or more active agents described above.

In a further aspect of the invention, the polypeptide, pharmaceutical composition or construct is administered sequentially, simultaneously or separately with at least one active agent selected from the list above.

Similarly, another aspect of the invention provides a combination product comprising:

(A) a polypeptide, pharmaceutical composition or construct of the present invention; and (B) one or more other active agents, wherein each of components (A) and (B) is formulated in admixture with a pharmaceutically-acceptable adjuvant, diluent or carrier. In this aspect of the invention, the combination product may be either a single (combination) formulation or a kit-of-parts. Thus, this aspect of the invention encompasses a combination formulation including a polypeptide, pharmaceutical composition or construct of the present invention and another therapeutic agent, in admixture with a pharmaceutically acceptable adjuvant, diluent or carrier.

The invention also encompasses a kit of parts comprising components:

(i) a polypeptide, pharmaceutical composition or construct of the present invention in admixture with a pharmaceutically acceptable adjuvant, diluent or carrier; and (ii) a formulation including one or more other active agents, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier. The one or more other active agents (i.e. component (B) above) may be, for example, any of the agents mentioned above in connection with the treatment of autoimmune diseases such as IBD (e.g. Crohn's disease and/or ulcerative colitis). If component (B) is more than one further active agent, these further active agents can be formulated with each other or formulated with component (A) or they may be formulated separately. In one embodiment component (B) is one other therapeutic agent. In another embodiment component (B) is two other therapeutic agents. The combination product (either a combined preparation or kit-of-parts) of this aspect of the invention may be used in the treatment or prevention of an autoimmune disease (e.g. the autoimmune diseases mentioned herein).

Stability

In one embodiment, the polypeptide or construct of the invention is delivered orally. Accordingly, the polypeptide or construct of the invention suitably substantially retains neutralisation ability and/or potency when delivered orally.

Suitably, the polypeptide or construct of the present invention substantially retains neutralisation ability and/or potency when delivered orally and after exposure to the intestinal tract (for example, after exposure to proteases of the small and/or large intestine and/or IBD inflammatory proteases). Such proteases include enteropeptidase, trypsin, chymotrypsin, and irritable bowel disease inflammatory proteases (such as MMP3, MMP12 and cathepsin).

Proteases of, or produced in, the small and/or large intestine include proteases sourced from intestinal commensal microflora and/or pathogenic bacteria, for example wherein the proteases are cell membrane-attached proteases, excreted proteases and proteases released on cell lysis). Most suitably the proteases are trypsin and chymotrypsin.

Suitably the intestinal tract is the intestinal tract of a dog, pig, human, cynomolgus monkey or mouse. More suitably the intestinal tract is the intestinal tract of a human, cynomolgus monkey or mouse, most suitably a human. The small intestine suitably consists of the duodenum, jejunum and ileum. The large intestine suitably consists of the cecum, colon, rectum and anal canal. The intestinal tract, as opposed to the gastrointestinal tract, consists of only the small intestine and the large intestine. In one embodiment the polypeptide or construct of the present invention is substantially resistant to proteases of the intestinal tract, most suitably the human intestinal tract.

Stability in the Buccal Cavity, Pharynx and Esophagus

The buccal cavity, pharynx and esophagus precede the stomach in the gastrointestinal tract. Suitably, the polypeptide or construct of the present invention substantially retains neutralisation ability and/or potency when delivered orally and after exposure to the buccal cavity, pharynx and esophagus (for example, after exposure to proteases of the buccal cavity, pharynx and esophagus). Proteases of the buccal cavity, pharynx and esophagus include proteases sourced from commensal microflora and/or pathogenic bacteria, for example wherein the proteases are cell membrane-attached proteases, excreted proteases and proteases released on cell lysis).

Suitably the buccal cavity, pharynx and esophagus are those of a dog, pig, human, cynomolgus monkey or mouse. More suitably the buccal cavity, pharynx and esophagus are those of a human, cynomolgus monkey or mouse, most suitably a human.

The polypeptide or construct of the present invention substantially retains neutralisation ability when suitably 10% or more, more suitably 20% or more, more suitably 30% or more, more suitably 40% or more, more suitably 50% or more, more suitably 60% or more, more suitably 70% or more, more suitably 80% or more, more suitably 90% or more, more suitably 95% or more, or most suitably 100% of the original neutralisation ability of the polypeptide or construct of the invention is retained after exposure to proteases present in the small and/or large intestine and/or IBD inflammatory proteases.

Suitably the polypeptide or construct of the invention substantially retains neutralisation ability after exposure to proteases present in the small and/or large intestine and/or IBD inflammatory proteases for, for example, up to at least 2, more suitably up to at least 3, more suitably up to at least 4, more suitably up to at least 5, more suitably up to at least 5.5, more suitably up to at least 6, more suitably up to at least 6.5, more suitably up to at least 7, more suitably up to at least 7.5, more suitably up to at least 10, more suitably up to at least 13 or more suitably up to at least 16 hours at 37 degrees C.

Suitably 10% or more, more suitably 20% or more, more suitably 30% or more, more suitably 40% or more, more suitably 50% or more, more suitably 60% or more, more suitably 70% or more, more suitably 80% or more, more suitably 90% or more suitably 95% of the neutralisation ability of the polypeptide or construct of the invention is retained after at least 2 hours, more suitably at least 3 hours, more suitably at least 4 hours, more suitably at least 5 hours, more suitably at least 6 hours, more suitably at least 7 hours, more suitably at least 9 more suitably at least 11 hours, more suitably at least 13 hours or more suitably at least 16 hours of exposure to conditions of the intestinal tract, more suitably the small or large intestine, more suitably human faecal extract.

Suitably 10% or more, more suitably 20% or more, more suitably 30% or more, more suitably 40% or more, more suitably 50% or more, more suitably 60% or more, more suitably 70% or more, more suitably 80% or more, more suitably 90% or more suitably 95% or more of the neutralisation ability of the polypeptide or construct of the invention is retained after suitably at least 1, more suitably at least 2, more suitably at least 3, more suitably at least 4, more suitably at least 5 or more suitably at least 6 hours of exposure to mouse small intestinal supernatant.

Suitably 10% or more, more suitably 20% or more, more suitably 30% or more, more suitably 40% or more, more suitably 50% or more, more suitably 60% or more, more suitably 70% or more of the administered dose of polypeptides or constructs of the invention retain neutralisation ability against IL-7 and/or L-TSLP and remain in the faeces of a mouse, cynomolgus monkey and/or human (suitably excreted faeces or faeces removed from the intestinal tract) after at least 2 hours, more suitably at least 3 hours, more suitably at least 4 hours, more suitably at least 5 hours, more suitably at least 6 hours, more suitably at least 7 hours, more suitably at least 9 more suitably at least 11 hours, more suitably at least 13 hours or more suitably at least 16 hours after administration.

A polypeptide of the invention or construct of the invention remains substantially intact when suitably 10% or more, more suitably 20% or more, more suitably 30% or more, more suitably 40% or more, more suitably 50% or more, more suitably 60% or more, more suitably 70% or more, more suitably 80% or more, more suitably 90% or more, more suitably 95% or more, more suitably 99% or more, most suitably 100% of the administered quantity of polypeptide of the invention or construct remains intact after exposure to proteases present in the small and/or large intestine and/or IBD inflammatory proteases.

'Stability' and 'survival' such as '% stability' and '% survival' are used interchangeably herein. "Substantially retains neutralisation ability" and "substantially resistant" are used interchangeably herein.

In one embodiment of the invention, based on their stability in human faecal supernatant digests, there is provided a polypeptide comprising or more suitably consisting of the polypeptide sequence of any one of the ICVDs recited as follows:

V7R-2E9, ID-A59U, ID-A2U, ID-A9U, ID-A10U, ID-A11U, ID-A12U, ID-A14U, ID-A15U, ID-A16U, ID-A17U, ID-A18A, ID-A19U, ID-A20U, ID-A21U, ID-A24U, ID-A43U, ID-A25U, ID-A30U, ID-A31U, ID-A50U, ID-A33U, ID-A52U, ID-A34U, ID-A53U, ID-A35U, ID-A54U, ID-A36U, ID-A55U, ID-A37U, ID-A38U, ID-A57U, ID-A39U, ID-A40U, V7R-2F6, V7R-6C12, V7R-2B6, V7R-3B5, V7R-4F6, V7R-2E5, ID-A3U, ID-A4U, ID-A5U, ID-A6U, ID-A7U, ID-A8U, ID-A13U, ID-A23U, ID-A26U, ID-A27U, ID-A28U, ID-A29U and ID-A32U.

There is also provided a polypeptide comprising three complementarity determining regions (CDR1-CDR3) and four framework regions (FR1-FR4), wherein CDR1 comprises or more suitably consists of the CDR1 sequence of any of the above ICVDs, CDR2 comprises or more suitably consists of the CDR2 sequence of any of the above ICVDs and CDR3 comprises or more suitably consists of the CDR3 sequence of any of the above ICVDs. Most suitably, the polypeptide comprises all three CDRs from one single ICVD above.

Based on their stability in human faecal supernatant digests, more suitably there is provided a polypeptide comprising or more suitably consisting of the polypeptide sequence of any one of the ICVDs recited as follows:

V7R-2E9, ID-A59U, ID-A2U, ID-A9U, ID-A10U, ID-A11U, ID-A12U, ID-A14U, ID-A15U, ID-A16U, ID-A17U, ID-A18A, ID-A19U, ID-A20U, ID-A21U, ID-A24U, ID-A43U, ID-A25U, ID-A30U, ID-A31U, ID-A50U, ID-A33U, ID-A52U, ID-A34U, ID-A53U, ID-A35U, ID-A54U, ID-A36U, ID-A55U, ID-A37U, ID-A38U, ID-A57U, ID-A39U, ID-A40U, V7R-2F6, V7R-6C12, V7R-2B6, V7R-3B5, V7R-4F6 and V7R-2E5.

There is also provided a polypeptide comprising three complementarity determining regions (CDR1-CDR3) and four framework regions (FR1-FR4), wherein CDR1 comprises or more suitably consists of the CDR1 sequence of any of the above ICVDs, CDR2 comprises or more suitably consists of the CDR2 sequence of any of the above ICVDs and CDR3 comprises or more suitably consists of the CDR3 sequence of any of the above ICVDs. Most suitably, the polypeptide comprises all three CDRs from one single ICVD above.

Based on their stability in human faecal supernatant digests, more suitably there is provided a polypeptide comprising or more suitably consisting of the polypeptide sequence of any one of the ICVDs recited as follows:

V7R-2E9, ID-A59U, ID-A2U, ID-A9U, ID-A10U, ID-A11U, ID-A12U, ID-A14U, ID-A15U, ID-A16U, ID-A17U, ID-A18A, ID-A19U, ID-A20U, ID-A21U, ID-A24U, ID-A43U, ID-A25U, ID-A30U, ID-A31U, ID-A50U, ID-A33U, ID-A52U, ID-A34U, ID-A53U, ID-A35U, ID-A54U, ID-A36U, ID-A55U, ID-A37U, ID-A38U, ID-A57U, ID-A39U, ID-A40U.

There is also provided a polypeptide comprising three complementarity determining regions (CDR1-CDR3) and four framework regions (FR1-FR4), wherein CDR1 comprises or more suitably consists of the CDR1 sequence of any of the above ICVDs, CDR2 comprises or more suitably consists of the CDR2 sequence of any of the above ICVDs and CDR3 comprises or more suitably consists of the CDR3 sequence of any of the above ICVDs. Most suitably, the polypeptide comprises all three CDRs from one single ICVD above.

Preparative Methods

Polypeptides of the invention can be obtained and manipulated using the techniques disclosed for example in Green and Sambrook 2012 Molecular Cloning: A Laboratory Manual 4th Edition Cold Spring Harbour Laboratory Press.

Monoclonal antibodies can be produced using hybridoma technology, by fusing a specific antibody-producing B cell with a myeloma (B cell cancer) cell that is selected for its ability to grow in tissue culture and for an absence of antibody chain synthesis (Köhler and Milstein 1975 and Nelson et al 2000).

A monoclonal antibody directed against a determined antigen can, for example, be obtained by:

a) immortalizing lymphocytes obtained from the peripheral blood of an animal previously immunized with a determined antigen, with an immortal cell and preferably with myeloma cells, in order to form a hybridoma, b) culturing the immortalized cells (hybridoma) formed and recovering the cells producing the antibodies having the desired specificity.

Alternatively, the use of a hybridoma cell is not required. Accordingly, monoclonal antibodies can be obtained by a process comprising the steps of:

a) cloning into vectors, especially into phages and more particularly filamentous bacteriophages, DNA or cDNA sequences obtained from lymphocytes especially peripheral blood lymphocytes of an animal (suitably previously immunized with determined antigens), b) transforming prokaryotic cells with the above vectors in conditions allowing the production of the antibodies, c) selecting the antibodies by subjecting them to antigen-affinity selection, d) recovering the antibodies having the desired specificity.

Methods for immunizing camelids, cloning the VHH repertoire of B cells circulating in blood (Chomezynnski and Sacchi 1987), and isolation of antigen-specific VHHs from immune (Arbabi-Ghahroudi et al 1997) and nonimmune (Tanha et al 2002) libraries using phage, yeast, or ribosome display are known (WO92/01047, Nguyen et al 2001 and Harmsen et al 2007).

Antigen-binding fragments of antibodies such as the scFv and Fv fragments can be isolated and expressed in *E. coli* (Miethe et al 2013, Skerra et al 1988 and Ward et al 1989).

Mutations can be made to the DNA or cDNA that encode polypeptides which are silent as to the amino acid sequence of the polypeptide, but which provide preferred codons for translation in a particular host. The preferred codons for translation of a nucleic acid in, e.g., *E. coli* and *S. cerevisiae*, are known.

Mutation of polypeptides can be achieved for example by substitutions, additions or deletions to a nucleic acid encoding the polypeptide. The substitutions, additions or deletions to a nucleic acid encoding the polypeptide can be introduced by many methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis (Ling et al 1997), gene reassembly, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

In particular, artificial gene synthesis may be used (Nambiar et al 1984, Sakamar and Khorana 1988, Wells et al 1985 and Grundstrom et al 1985). A gene encoding a polypeptide of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity (Verma and Eckstein 1998)

Expression of immunoglobulin chain variable domains such as VHs and VHHs can be achieved using a suitable expression vector such as a prokaryotic cell such as bacteria, for example *E. coli* (for example according to the protocols disclosed in WO94/04678, which is incorporated herein by reference and detailed further below). Expression of immunoglobulin chain variable domains such as VHs and VHHs can also be achieved using eukaryotic cells, for example insect cells, CHO cells, Vero cells or suitably yeast cells such as yeasts belonging to the genera *Aspergillus, Saccharomyces, Kluyveromyces, Hansenula* or *Pichia*. Suitably *S. cerevisiae* is used (for example according to the protocols disclosed in WO94/025591, which is incorporated herein by reference and detailed further below).

Specifically, VHHs can be prepared according to the methods disclosed in WO94/04678 using *E. coli* cells by a process comprising the steps of:

a) cloning in a Bluescript vector (Agilent Technologies) a DNA or cDNA sequence coding for the VHH (for example obtained from lymphocytes of camelids or produced synthetically) optionally including a His-tag, b) recovering the cloned fragment after amplification using a 5' primer specific for the VHH containing an XhoI site and a 3' primer containing the SpeI site having the sequence TC TTA ACT AGT GAG GAG ACG GTG ACC TG (SEQ ID NO: 81), c) cloning the recovered fragment in phase in the Immuno PBS vector (Huse et al 1989) after digestion of the vector with XhoI and SpeI restriction enzymes, d) transforming host cells, especially *E. coli* by transfection with the recombinant Immuno PBS vector of step c, e) recovering the expression product of the VHH coding sequence, for instance by affinity purification such as by chromatography on a column using Protein A, cation exchange, or a nickel-affinity resin if the VHH includes a His-tag.

Alternatively, immunoglobulin chain variable domains such as VHs and VHHs are obtainable by a process comprising the steps of:

a) obtaining a DNA or cDNA sequence coding for a VHH, having a determined specific antigen binding site, b) amplifying the obtained DNA or cDNA, using a 5' primer containing an initiation codon and a HindIII site, and a 3' primer containing a termination codon having a XhoI site, c) recombining the amplified DNA or cDNA into the HindIII (position 2650) and XhoI (position 4067) sites of a plasmid pMM984 (Merchlinsky et al 1983), d) transfecting permissive cells especially NB-E cells (Faisst et al 1995) with the recombinant plasmid, e) recovering the obtained products.

Further, immunoglobulin chain variable domains such as VHHs or VHs can be produced using *E. coli* or *S. cerevisiae* according to the methods disclosed in Frenken et al 2000 and WO99/23221 (herein incorporated by reference in their entirety) as follows:

After taking a blood sample from an immunised llama and enriching the lymphocyte population via Ficoll (a neutral, highly branched, high-mass, hydrophilic polysaccharide which dissolves readily in aqueous solutions—Pharmacia) discontinuous gradient centrifugation, isolating total RNA by acid guanidium thiocyanate extraction (Chomezynnski and Sacchi 1987), and first strand cDNA synthesis (e.g. using a cDNA kit such as RPN 1266 (Amersham)), DNA fragments encoding VHH and VH fragments and part of the short or long hinge region are amplified by PCR using the specific primers detailed on pages 22 and 23 of WO99/23221. Upon digestion of the PCR fragments with PstI and HindIII or BstEII, the DNA fragments with a length between about 300 and 450 bp are purified via agarose gel electrophoresis and ligated in the *E. coli* phagemid vector pUR4536 or the episomal *S. cerevisiae* expression vector pUR4548, respectively. pUR4536 is derived from pHEN (Hoogenboom et al 1991) and contains the laclq gene and unique restriction sites to allow the cloning of the llama VHH and xVH genes. pUR4548 is derived from pSY1 (Harmsen et al 1993). From this plasmid, the BstEII site in the leu2 gene is removed via PCR and the cloning sites between the SUC2 signal sequence and the terminator are replaced in order to facilitate the cloning of the VH/VHH gene fragments. The VH/VHHs have the c-myc tag at the C-terminus for detection. Individual *E. coli* JM109 colonies are transferred to 96 well microtiter plates containing 150 ml 2TY medium supplemented with 1% glucose and 100 mg L$^{-1}$ ampicillin.

After overnight growth (37 degrees C.), the plates are duplicated in 2TY medium containing 100 mg L$^{-1}$ ampicillin and 0.1 mM IPTG. After another overnight incubation and optionally freezing and thawing, cells are centrifuged and pelleted and the supernatant can be used in an ELISA. Individual *S. cerevisiae* colonies are transferred to test tubes containing selective minimal medium (comprising 0.7% yeast nitrogen base, 2% glucose, supplemented with the essential amino acids and bases) and are grown for 48 h at 30 degrees C. Subsequently, the cultures are diluted ten times in YPGal medium (comprising 1% yeast extract, 2% bacto peptone and 5% galactose). After 24 and 48 h of growth, the cells are pelleted and the culture supernatant can be analysed in an ELISA. Absorbance at 600 nm (OD600) is optionally measured.

Further, immunoglobulin chain variable domains such as VH/VHHs can be produced using *S. cerevisiae* using the procedure as follows:

Isolate a naturally-occuring DNA sequence encoding the VH/VHH or obtain a synthetically produced DNA sequence encoding the VH/VHH, including a 5'-UTR, signal sequence, stop codons and flanked with SacI and HindIII sites (such a synthetic sequence can be produced as outlined above or for example may be ordered from a commercial supplier such as Geneart (Life Technologies)).

Use the restriction sites for transfer of the VH/VHH gene to the multi-copy integration (MCI) vector pUR8569 or pUR8542, as follows. Cut the DNA sequence encoding the VHH optionally contained within a shuttle vector, cassette or other synthetic gene construct and the MCI vector with SacI and HindIII using: 25 ul VHH DNA (Geneart plasmid or MCI vector), 1 ul SacI, 1 ul HindIII, 3 ul of a suitable buffer for double digestion such as NEB buffer 1 (New England Biolabs) overnight at 37 degrees C. Run 25 ul of digested DNA encoding the VHH and 25 ul of digested MCI vector on a 1.5% agarose gel with 1×TAE buffer and then perform gel extraction for example using QlAquick Gel Extraction Kit (Qiagen)). Set-up a ligation of digested MCI vector and digested DNA encoding the VH/VHH as follows: 100 ng vector, 30 ng VHH gene, 1.5 ul 10× ligase buffer, 1 ul T4 DNA ligase, and ddH$_2$O. Then perform ligation overnight at 16 degrees C.

Next transform the *E. coli* cells. For chemical competent XL-1 blue cells, thaw 200 ul heat competent XL-1 blue cells and add 5 ul ligation mix on ice for about 30 minutes followed by heat shock for 90 seconds at 42 degrees C. Then add 800 ul Luria-Bertani low salt medium supplemented with 2% glucose and recover cells for 2 hours at 37 degrees C. Plate cells on Luria-Bertani agar and ampicillin (100 ug/ml) plates and keep overnight at 37 degrees C. For electro competent TG1 *E. coli* cells, use an electroporation cuvette. In the electroporation cuvette: thaw 50 ul electro competent TG1 cells and 1 ul ligation mix on ice for about 15 minutes. Place the cuvette in the holder and pulse. Add 500 ul of 2TY medium and recover cells for 30 minutes at 37 degrees C. Plate 100 ul of cells on Luria-Bertani, agar, containing ampicillin (100 ug/ml) and 2% glucose plates. Keep plates at 37 degrees C. overnight.

After cloning of the VH/VHH gene into *E. coli* as detailed above, *S. cerevisiae* can be transformed with the linearized MCI vector. Before transformation is carried out, some steps are performed: (i) the DNA should be changed from circular to linear by digestion or else the DNA cannot be integrated into the yeast genome and (ii) the digested DNA should be cleaned of impurities by ethanol precipitation. Also, during the transformation process, the yeast cells are made semipermeable so the DNA can pass the membrane.

Preparation for yeast transformation: perform a HpaI digestion of the midi-prep prepared from the selected *E. coli* colony expressing the VH/VHH gene as follows. Prepare a 100 ul solution containing 20 ng of midi-prep, 5 ul HpaI, 10 ul of appropriate buffer such as NEB4 buffer (BioLabs), and ddH$_2$O.

Cut the DNA with the HpaI at room temperature overnight. Next perform an ethanol precipitation (and put to one side a 5 ul sample from HpaI digestion). Add 300 ul ethanol 100% to 95 ul HpaI digested midiprep, vortex, and spin at full speed for 5 minutes. Carefully decant when a pellet is present, add 100 ul of ethanol 70%, then spin again for 5 minutes at full speed. Decant the sample again, and keep at 50-60 degrees C. until the pellet is dry. Re-suspend the pellet in 50 ul ddH$_2$O. Run 5 ul on a gel beside the 5 ul HpaI digested sample.

Yeast transformation: prepare YNBglu plates. Use 10 g agar+425 ml water (sterilised), 25 ml filtered 20×YNB (3.35 g YNB (yeast nitrogen base) in 25 ml sterilized H$_2$O) and 50 ml sterile 20% glucose and pour into petri dishes. Pick one yeast colony from the masterplate and grow in 3 ml YSD (Yeast Extract Soytone Dextrose) overnight at 30 degrees C. Next day prepare about 600 ml YSD and use to fill 3 flasks with 275 ml, 225 ml and 100 ml YSD. Add 27.5 ul yeast YSD culture to the first flask and mix gently. Take 75 ml from the first flask and put this in the second flask, mix gently. Take 100 ml from the second flask and put in the third one, mix gently. Grow until reaching an OD660 of between 1 and 2. Divide the flask reaching this OD over 4 Falcon tubes, ±45 ml in each. Spin for 2 minutes at 4200 rpm. Discard the supernatant. Dissolve the pellets in two Falcon tubes with 45 ml H$_2$O (reducing the number of tubes from 4 to 2). Spin for 2 minutes at 4200 rpm. Dissolve the pellets in 45 ml H$_2$O (from 2 tubes to 1). Spin for 2 minutes at 4200 rpm. Gently dissolve the pellets in 5 ml lithium acetate (LiAc) (100 mM), and spin for a few seconds. Carefully discard some LiAc, but retain over half of the LiAc in the tube. Vortex the cells, boil carrier DNA for 5 minutes and quickly chill in ice-water. Add to a 15 ml tube containing: 240 ul PEG, 50 ul cells, 36 uLiAc (1M), 25 ul carrier DNA, 45 ul ethanol precipitated VH/VHH. Mix gently after each step (treat the blank sample the same, only without ethanol precipitated VH/VHH). Incubate for 30 minutes at 30 degrees C., gently invert the tube 3-4 times, then heat shock for 20-25 minutes at 42 degrees C. Spin up to 6000 rpm for a brief time. Gently remove the supernatant and add 250 ul ddH$_2$O and mix. Streak all of it on an YNBglu plate until plates are dry and grow for 4-5 days at 30 degrees C. Finally, prepare YNBglu plates by dividing plates in 6 equal parts, number the parts 1 to 6, inoculate the biggest colony and streak out number 1. Repeat for other colonies from big to small from 1 to 6. Grow at 30 degrees C. for 3-4 days large until colonies are produced. The VH/VHH clones are grown using glucose as a carbon source, and induction of VH/VHH expression is done by turning on the Galactose-7-promoter by adding 0.5% galactose. Perform a 3 mL small scale culture to test the colonies and choose which one shows the best expression of the VH or VHH. This colony is then used in purification.

Purification: the VH/VHH is purified by cation exchange chromatorgraphy with a strong anion resin (such as Capto S). On day 1, inoculate the selected yeast colony expressing the VH/VHH in 5 ml YSD medium (YS medium+2% glucose) and grow the cells in 25 mL sealed sterile tubes at 30 degrees C. overnight (shaking at 180 rpm). On day 2, dilute the 5 ml overnight culture in 50 mL freshly prepared YS medium+2% glucose+0.5% galactose, grow the cells in 250 ml aerated baffled flasks at 30 degrees C. for two nights (shaking at 180 rpm). On day 4, spin the cells down in a centrifuge at 4200 rpm for 20 min. Cation exchange purification step using a strong anion resin: adjust the pH of the supernatant containing the ligand to 3.5. Wash 0.75 ml resin (+/−0.5 mL slurry) per of 50 mL supernatant with 50 mL of ddH$_2$O followed by three washes with binding buffer. Add the washed resin to the supernatant and incubate the suspension at 4 degrees C. on a shaker for 1.5 hours. Pellet the resin-bound VH/VHH by centrifugation at 500 g for 2 minutes and wash it with wash buffer. Decant supernatant and re-suspend the resin with 10 mL of binding buffer. Put a filter in a PD-10 column, pour the resin in the column and let the resin settle for a while, then add a filter above the resin. Wait until all binding buffer has run through. Elute the VH/VHH with 6×0.5 ml elution buffer. Collect the elution fractions in eppendorf tubes. Measure the protein concentration of the 6 eluted fractions with a Nanodrop. Pool the fractions that contain the VHH and transfer the solution into a 3,500 Da cutoff dialysis membrane. Dialyze the purified protein solution against 3 L of PBS overnight at 4 degrees C. On day 5, dialyze the purified protein solution against 2 L of fresh PBS for an additional 2 hours at 4 degrees C. Finally, calculate the final concentration by BCA.

Although discussed in the context of the VH/VHH, the techniques described above could also be used for scFv, Fab, Fv and other antibody fragments if required.

Multiple antigen-binding fragments (suitably VH/VHHs) can be fused by chemical cross-linking by reacting amino acid residues with an organic derivatising agent such as described by Blattler et al 1985. Alternatively, the antigen-binding fragments may be fused genetically at the DNA level i.e. a polynucleotide construct formed which encodes the complete polypeptide construct comprising one or more antigen-binding fragments. One way of joining multiple antigen-binding fragments via the genetic route is by linking the antigen-binding fragment coding sequences either directly or via a peptide linker. For example, the carboxy-terminal end of the first antigen-binding fragment may be linked to the amino-terminal end of the next antigen-binding fragment. This linking mode can be extended in order to link antigen-binding fragments for the construction of tri-, tetra-, etc. functional constructs. A method for producing multivalent (such as bivalent) VHH polypeptide constructs is disclosed in WO 96/34103 (herein incorporated by reference in its entirety).

Suitably, the polypeptide of the invention (in particular, a VHH of the invention) can be produced in a fungus such as a yeast (for example, *S. cerevisiae*) comprising growth of the fungus on a medium comprising a carbon source wherein 50-100 wt % of said carbon source is ethanol, according to the methods disclosed in WO02/48382. Large scale production of VHH fragments in *S. cerevisiae* is described in Thomassen et al 2002.

In one aspect of the invention there is provided a process for the preparation of the polypeptide or construct of the invention comprising the following steps:
  i) cloning into a vector, such as a plasmid, the polynucleotide of the invention,
  ii) transforming a cell, such as a bacterial cell or a yeast cell capable of producing the polypeptide or construct of the invention, with said vector in conditions allowing the production of the polypeptide or construct,
  iii) recovering the polypeptide or construct, such as by affinity chromatography.

Clauses setting out further embodiments of the invention are as follows:

CLAUSES

1. A polypeptide capable of inhibiting IL-7 and/or L-TSLP binding to IL-7R.
2. The polypeptide according to clause 1, wherein the polypeptide is capable of inhibiting IL-7 binding to IL-7R.
3. The polypeptide according to clause 1, wherein the polypeptide is capable of inhibiting L-TSLP binding to IL-7R.
4. The polypeptide according to any one of clauses 1 to 3, wherein the polypeptide is capable of inhibiting IL-7 binding to IL-7R and L-TSLP binding to IL-7R.
5. The polypeptide according to any one of clauses 1 to 4 wherein the polypeptide binds to IL-7Rα.
6. The polypeptide according to any one of clauses 1 to 5 wherein the polypeptide comprises three complementarity determining regions (CDR1-CDR3) and four framework regions (FR1-FR4), wherein CDR1 comprises a sequence sharing 60% or greater sequence identity with SEQ ID NO: 1, CDR2 comprises a sequence sharing 60% or greater sequence identity with SEQ ID NO: 2 and CDR3 comprises a sequence sharing 60% or greater sequence identity with SEQ ID NO: 3.
7. The polypeptide according to clause 6, wherein CDR1 comprises a sequence sharing 80% or greater sequence identity with SEQ ID NO: 1, CDR2 comprises a sequence sharing 80% or greater sequence identity with SEQ ID NO: 2 and CDR3 comprises a sequence sharing 80% or greater sequence identity with SEQ ID NO: 3.
8. The polypeptide according to clause 7, wherein CDR1 comprises SEQ ID NO: 1 or SEQ ID NO: 71; CDR2 comprises SEQ ID NO: 2, SEQ ID NO: 72, SEQ ID NO: 73, SEQ ID NO: 74, SEQ ID NO: 75 or SEQ ID NO: 76 and CDR3 comprises SEQ ID NO: 3, SEQ ID NO: 77 or SEQ ID NO: 78.
9. The polypeptide according to clause 8, wherein the polypeptide comprises SEQ ID NO: 8.

The polypeptide according to any one of clause 1 to 9, wherein the polypeptide is an antibody or antibody fragment.

11. The polypeptide according to any one of clause 1 to 10, wherein the polypeptide neutralizes IL-7R binding to IL-7 with an EC50 of 2 nM or less.
12. The polypeptide according to any one of clause 1 to 11, wherein the polypeptide is substantially resistant to proteases of the human intestinal tract.
13. The polypeptide according to any one of clause 1 to 12, for use as a medicament.
14. The polypeptide according to clause 13 for use in the treatment of an autoimmune and/or inflammatory disease.
15. The polypeptide for use according to either clause 13 or 14, wherein the polypeptide is for use in oral administration.

The present invention will now be further described by means of the following non-limiting examples.

EXAMPLES

Example 1: Immunisation and Phage Library Construction

Two llamas were each immunised with soluble human recombinant IL-7Rα. Blood was collected from both llamas at different time points during the immunization, and tested for IL-7Rα binding and neutralisation to monitor the development of the immune response against the IL-7Rα. The analysis showed that only one llama developed good anti-IL-7Rα antibody titres while the other llama was unable to respond to IL-7Rα immunization. RNA isolated from white blood cells collected from the responsive llama at the end of the immunisation was used to generate twelve separate phage display libraries.

Example 2: Library Selections for Phages with Human IL-7Rα-Binding Activity

Library selection strategies were developed to isolate ICVDs that bind to epitopes present on the extracellular domain of the IL-7Rα subunit, including ICVDs that interfere with the binding of IL-7 to IL-7R. Several methods were used for the selective enrichment of phages displaying ICVDs with IL-7Rα binding characteristics and other desirable properties including high binding affinity and resistance to intestinal proteases. Phages present in eluates from the different library selections were used to infect E. coli and individual colonies were picked into master-plates and propagated to generate clonal cultures. Periplasmic supernatants containing selected monoclonal ICVDs were used for primary evaluation studies to identify those with the required characteristics.

From a total of 630 library-selected clones picked into the original 8 master-plates screened, a final set of 7 primary clones was selected for production in E. coli and the ICVDs affinity purified for more detailed evaluation studies.

DNA sequences of the 7 primary clones isolated above (V7R-2E5, V7R-2E9, V7R-2F6, V7R-6C12, V7R-2B6, V7R-3B5, and V7R-4F6) were re-cloned into the vector pMEK222 (thus introducing C-terminal FLAG and 6×His tags) for production in E. coli followed by affinity purification for more detailed evaluation studies. The polypeptide sequences of these ICVDs, excluding FLAG and His tags, are shown in the alignment provided above in the section titled "Polypeptide and polynucleotide sequences". Clinical anti-IL-7R antibody mAb829 (a 150 kDa antibody containing heavy chain and light chain, also known as "GSK2618960" as disclosed in Ellis et al 2019) was produced and used as a comparator in a number of the following examples.

Key aims of the following examples were to identify those ICVD clones with the ability to inhibit IL-7 binding to IL-7R plus having a degree of intrinsic resistance to inactivation by small intestinal proteases.

Example 3: Potency and Protease Resistance of Primary Clones

Potency

The potency of the 7 primary clones was assessed using an IL-7/IL-7R neutralising ELISA.

The primary clones were sub-cloned from phagemids into pMEK222 plasmid for the addition of C-terminal FLAG-6×His tags and expression in E. coli. These ICVDs were expressed from E. coli TG1 and purified via the 6×His tag.

A 7-point dilution series of the clones was prepared in 1% BSA (at 2× the assay concentration) starting at 300 nM and using a 3.2 dilution factor. The mAb829 comparator antibody was used as a positive control in the ELISA with a concentration range between 10 nM and 0.088 nM (2× the assay concentration). Volumes sufficient for triplicates were prepared for each clone dilution, while a volume sufficient for 2 triplicates (2 plates) was prepared for mAb829. 85 µL (or 170 μL) of each ICVD (or mAb829) dilution were mixed with 85 μL (or 170 μL) of 10 ng/mL IL-7(2× the assay concentration). 85 μL of IL-7 were mixed with 85 μL of block buffer to have the IL-7 (1×) full binding signal in each plate. Block buffer alone was also added to each plate as blank. Bound IL-7 was then measured using biotinylated anti-hIL-7 followed by Extravidin-HRP. TMB reaction was stopped after 30 minutes.

$EC_{50}$ values were generated in Graphpad prism using the ELISA signal blank corrected A450 data and 'log(inhibitor) vs. response—Variable slope (four parameters)' to fit curves and generate $EC_{50}$. These values are shown in Table 1 below. All the ICVDs were shown to be as effective as the comparator mAb829 in inhibiting the binding of hIL-7 to hIL-7R, and most of them were slightly more potent than mAb829.

Protease Resistance

The seven purified ICVDs were incubated in the presence of mouse small intestinal supernatant ("mouse SI") and supernatant prepared from pooled human faecal samples ("HFP").

Stock dilutions of all the ICVDs were prepared in 1× PBS containing 1% BSA at 250 μg/mL (in 30 μL final volume). Digestion mix reactions were then prepared for each ICVD in PCR strips in a final volume of 60 μL with ICVDs being at a final concentration of 20 μg/mL (55.2 μL of digestive matrix+4.8 μL of ICVD at 250 μg/mL). 4.8 μL of 1× PBS was instead used for the no-ICVD control. 25 μL of each digestive reaction were subsequently transferred to (i) new PCR tube containing cold stop buffer (these were used as T=0 time point) and frozen at −80° C.; and (ii) to a new empty PCR tube and incubated in a PCR thermocycler for digestion at 37° C. (digested and no-ICVD controls samples). Samples digested in mouse SI were removed from the thermocycler after 2 h, while samples digested in HFP were removed after 4 h. Samples were immediately stopped with 25 μL of cold stop buffer and frozen at −80° C. until analysed.

Digested samples were tested in the ELISA detailed under 'Potency' above at a final starting dilution of 1:100 with subsequent 6 serial dilutions using a 1.8 (for digested samples) or 2.1 (for non-digested samples) dilution factor, and assayed in triplicate wells in each plate. The non digested samples (0 h) are considered as the standard curves as no protease digestion should theoretically happen in these samples (as they are treated on ice and stop buffer is immediately added following addition of the digestive matrix).

If digestion occurs in the 'digested' samples it is expected that there will be a shift of the curve to the left (compared to T=0 h). The greater the shift the more labile the ICVD. "% survival" represents the level of activity retained after digestion.

All the clones showed a high level of resistance to proteolytic degradation in both matrixes, and V7R-2E9 was identified as the most protease-resistant ICVD, showing complete resistance to human faecal pool digestion for up to 4 hours.

These results are summarised in Table 1 below.

TABLE 1

| Clone ID | SEQ ID NO | IL-7/IL-7R ELISA $EC_{50}$ (nM) | % Survival Mouse SI (2 h) | % Survival Human faeces (4 h) |
| --- | --- | --- | --- | --- |
| V7R-2B6 | 9 | 0.264 | 70.9 | 91.8 |
| V7R-2E5 | 10 | 0.64 | NT | NT |
| V7R-2E9 | 11 | 0.368 | 90.2 | 100 |
| V7R-2F6 | 12 | 0.361 | 66.4 | 90.2 |
| V7R-3B5 | 13 | 0.222 | 70.4 | 82.9 |
| V7R-4F6 | 14 | 0.259 | 80.4 | 88.5 |
| V7R-6C12 | 15 | 0.416 | 68.1 | 92.2 |

NT = not tested

SI=small intestinal supernatant

These polypeptides of the invention all demonstrated surprisingly high potency and survival in digestive matrices. It may be noted that, while these ICVDs are clearly related, the CDRs and frameworks of these polypeptides differ from one another by a number of residues (see alignments provided under "Polypeptide and polynucleotide sequences", above).

Example 4: Further Potency Assays Performed on V7R-2E9 and Comparator mAb829

IL-7/IL-7R Neutralising ELISA

The IL-7/IL-7R neutralising ELISA described above under example 3 was performed again on V7R-2E9 and clinical anti-IL-7R comparator antibody, mAb829. The results are given in Table 2 below.

TSLP/TSLPR/IL-7R ELISA

The ability of V7R-2E9 to neutralise the L-TSLP/TSLP-R complex binding to IL-7Rα was tested. 96-well plates were coated with 0.25 μg/mL recombinant human IL-7Rα-His$_6$-Fc+ 5 μg/mL BSA and then blocked. V7R-2E9 was serially diluted and mixed 1:1:1 with recombinant human L-TSLP (15 ng/mL final concentration) and human TSLP-R (20 ng/mL final concentration). Then the mixtures were incubated for 30 minutes to allow binding before adding to the IL-7Rα coated plates. Following 2 hours' incubation, bound L-TSLP was detected with 50 μL/well 0.3 μg/mL Biotinylated Rabbit anti-hTSLP antibody and then 50 μL/well ½₀₀₀ Extravidin-HRP, and levels of neutralisation of L-TSLP/TSLP-R complex binding to IL-7Rα by the ICVD was determined using GraphPad Prism. The results are given in Table 2 below.

IL-7 induced pSTAT5 in hPBMCs

The ability of V7R-2E9 to inhibit IL-7 binding to IL-7Rα and hamper STAT5 phosphorylation was tested, in vitro, in human lymphocytes. Human peripheral blood mononuclear cells (PBMCs) respond to exogenous IL-7 by stimulation of intracellular STAT5 phosphorylation though IL-7R signalling but this response can be negated by IL-7Rα-specific ICVDs that prevent IL-7/IL-7R binding.

A lymphocyte enriched population was isolated from human buffy coat and stored in 90% FBS 10% DMSO in liquid nitrogen. Cells were thawed and rested, for recovery, in complete RPMI-1640. After recovery, cells were plated in a round-bottom 96 well plate in 100p1, $2.5\times10^5$ cells/well and starved for 1 h in complete RPMI without FBS. After starvation, the desired ICVD concentrations were added to each well (50 μL/well), and plate incubated for 15 min at room temperature. Then 50 μL/well of IL-7 was added to each well and plate incubated for 15 min at 37° C. 5% $CO_2$. Reaction was stopped by quickly chilling the plate on ice followed by centrifugation and supernatant removal. Cells were then processed for fixation, permeabilization and pSTAT5 intracellular staining. Cells were incubated for 20 min on ice with 100 μL/well Cytofix/Cytoperm solution (BD Bioscience #554722), washed twice with 150 μl/well 1× Perm/Wash buffer (BD Bioscience #554723), incubated on ice for 30 min with 200 μL/well Perm buffer III (BD Bioscience #558050) and washed twice with 150 μL/well of 1× PBS 2% BSA (FACS buffer). Cells were subsequently stained for 1 h room temperature with 25 μL/well of pSTAT5 antibody ([47/Stat5(pY694)] (A488) (BD Bioscience #612598)) or the isotype control Mouse IgG1 ([B11/6] (FITC) (Abcam #ab91356)). Reaction was stopped by adding 150 μL/well of FACS buffer. After 1 wash/centrifugation step, cells were finally resuspended in 200 μL/well of FACS buffer and data acquired in the CytoFlex flow cytometer (Beckman Coulter). Data analysis was performed using the FlowJo software. The results are shown in Table 2 below.

TSLP-Induced TARC Secretion in Human Monocytes

V7R-2E9 was also tested to confirm IL-7R neutralising activity in a human monocytes cellular assay detailed. Human monocytes exhibit a TARC secretion response in culture medium following stimulation with TSLP as a result of TSLP/TSLP-R engagement with cell surface IL-7R. The ability for anti-IL-7Rα ICVDs to inhibit TSLP/TSLP-R binding to IL-7R and hamper TARC secretion was tested, in vitro, in human monocytes.

Monocytes were isolated from human buffy coat and plated in a flat-bottom 96 well plate, 100 μl/well containing $1×10^5$ cells, in complete RPMI. In order to increase monocyte purity, plated cells were left resting for 2 h at 37° C. 5% $CO_2$, and then non-adherent cells were removed by aspirating the medium in each well followed by a gentle 2× wash with warm cRPMI. Cells were incubated with the desired concentrations of ICVD in the presence of TSLP for 24 h at 37° C. 5% $CO_2$ (diluted in complete RPMI, final volume of 100 μL/well). After 24 h incubation, 75 μL of supernatant/well was collected and stored at −80° C. for further analysis of secreted TARC.

The level of neutralisation of human TSLP by anti-IL-7Rα agents was tested. 96-well plates were coated with 50 μL/well anti human TARC antibody and then blocked. Human TARC standard was serially diluted in assay diluent, and then 50 μL/well of the standard alongside 50 μL/well of recovered culture supernatants were added to the anti-TARC coated plates. Bound human TARC was detected with a Biotinylated anti-human TARC polyclonal antibody and then Avidin-HRP. The level of neutralisation of human TSLP by the agents was determined. The results are shown in Table 2 below.

TABLE 2

| Construct | IL-7/ IL-7R ELISA $EC_{50}$ nM | IL-7 induced pSTAT5 in hPBMCs $EC_{50}$ nM | TSLP/ TSLPR/ IL-7R ELISA $EC_{50}$ nM | TSLP-induced TARC secretion in human monocytes $EC_{50}$ nM |
|---|---|---|---|---|
| V7R-2E9 | 0.818 | 2.86 | 0.32 | 0.5-0.8 |
| mAb829 | 0.8 | 2.6 | 0.32 | 0.5-0.8 |

In summary, V7R-2E9 was shown to inhibit IL-7 and L-TSLP binding to IL-7R with potencies similar to the comparator clinical anti-IL-7R antibody mAb829 in both ELISA and cellular assays.

Example 5: Epitope Modelling

A model structure and epitope for V7R-2E9 were established in silico. This model was developed using the protein data bank (PDB) Aybq' file as template. 4ybq is the heavy chain of an FV bound to the rat GLUT5 facilitated glucose transporter member 5. The 4ybq template is particularly similar to V7R-2E9 in terms of the CDR3 loop length and expected conformation. PDB entry '3di3' is a high resolution structure of IL-7 bound to IL-7Rα. IL-7 was simply deleted from this structure to provide a target receptor for docking with the predicted V7R-2E9 structure.

Figure 3:
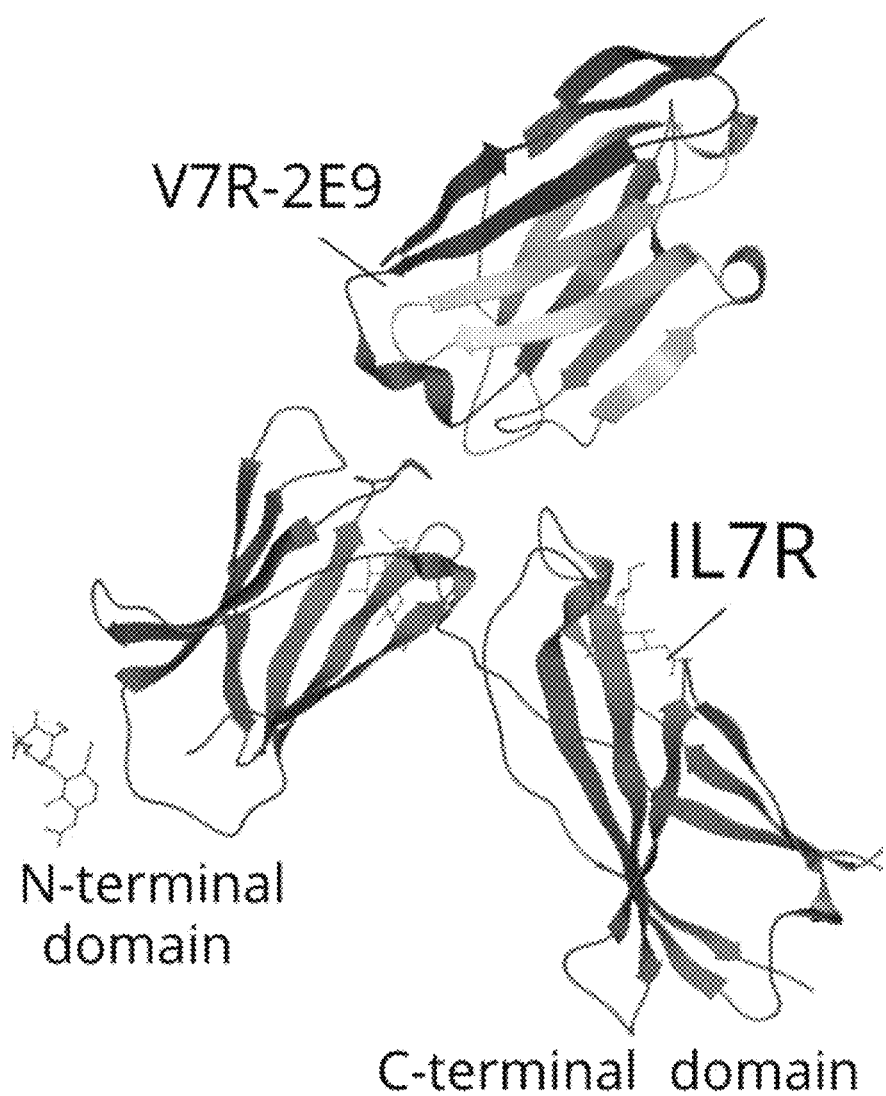
FIG. 3—Model structure of V7R-2E9 bound to IL-7Rα
Figure 4:
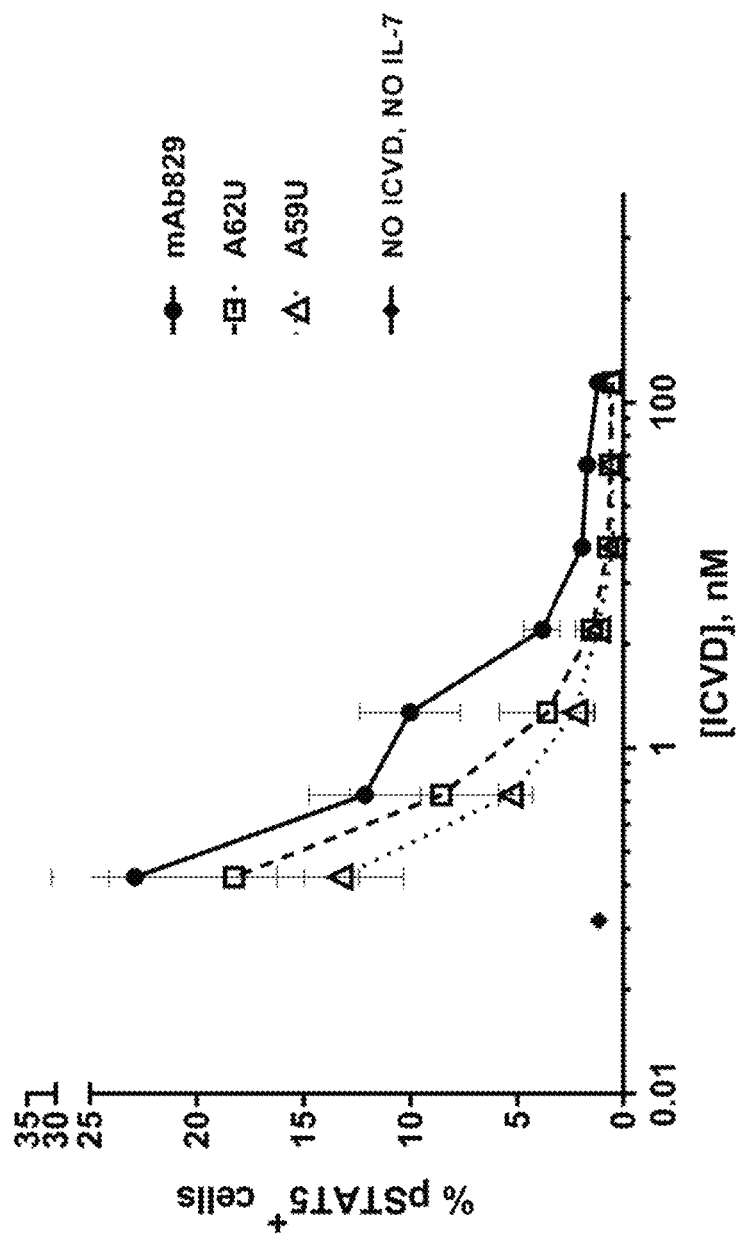
FIG. 4—A62U, A59U and mAb829 inhibition of IL-7 induced pSTAT5 in human lymphocytes FIG. 5—Cross-reactivity of ID-A40U with species IL-7Rα

As the HEX 8.0 docking methods employed work in a localized fashion over the surface of each domain, a number of target regions were selected over the IL-7Rα structure and run in parallel. The best solution for V7R-2E9 was representative of a cluster of 46 solutions, it had a very high energy score of −894 (DARS force field) and no 'bumps' (impermissibly close atomic positions) after energy minimization. FIG. 3 shows a ribbon schematic view of the position of V7R-2E9 docked on the IL-7Rα target. V7R-2E9 is positioned at the interface between the N- and C-terminal domains.

Table 3 lists the epitope residues of IL-7Rα that contact V7R-2E9. The residues which bury a particularly significant area at the interface are highlighted in bold (by reference to SEQ ID NO: 65).

TABLE 3

| Residue | Number | BSA (as % of ASA) |
|---|---|---|
| GLU | 27 | 5.8 |
| SER | 31 | 54.9 |
| LEU | 57 | 20.4 |
| VAL | 58 | 80.5 |
| GLU | 59 | 7.1 |
| LYS* | 77 | 22.8 |
| LYS | 78 | 8.4 |
| PHE | 79 | 63.3 |
| LEU | 80 | 78.6 |
| LEU | 81 | 64.0 |
| ILE | 82 | 69.6 |
| THR | 104 | 10.9 |
| LYS | 137 | 3.3 |
| LYS* | 138 | 78.5 |
| TYR* | 139 | 69.4 |
| LYS | 141 | 0.9 |
| HIS | 191 | 14.4 |
| TYR | 192 | 41.1 |
| PHE | 193 | 53.4 |

BSA is surface area buried at the interface.
ASA is surface area before complex forms
*form H-bonds Example 6: Optimisation to Reduce Immunogenicity The amino acid sequence of V7R-2E9 was aligned with human VH3 germline antibody sequences and potential humanising changes were identified. A selection of 18 single mutations and 2 combinations of changes at the end of framework 2/beginning of CDR2 were introduced into the V7R-2E9 parent ICVD sequence, and mutants produced from E. coli. ICVDs were tested initially for potency in the IL-7/IL-7R neutralisation ELISA. The clones displayed IL-7R neutralising activity similar to or greater than V7R-2E9, indicating that none of the mutations introduced into the parent ICVD had a detrimental effect on antigen binding. All the clones were then digested for 16 hours in human faecal supernatant material to measure their relative survival. (Table 4).

TABLE 4

| ICVD ID | SEQ ID NO | Mutation | Mutation location | ELISA EC50 (nM) | Human faecal stability (%) |
|---|---|---|---|---|---|
| V7R-2E9 | 11 | WT | n/a | 0.37-0.67 | 100 |
| ID-A2U | 16 | E23A | FR1 | 0.475 | 107 |
| ID-A3U | 17 | E23S | FR1 | n/a | n/a |
| ID-A4U | 18 | S24A | FR1 | 0.489 | 0 |
| ID-A5U | 19 | I26G | FR1 | 0.49 | 54 |
| ID-A6U | 20 | F37V | FR2 | 0.194 | 20.3 |
| ID-A7U | 21 | 44 to 49 EREFLA to GLEWS | FR2 | 0.513 | 0 |
| ID-A8U | 22 | 44 to 47 EREF to GLEW | FR2 | 0.604 | 55 |
| ID-A9U | 23 | E44G | FR2 | 0.168 | 79.4 |
| ID-A10U | 24 | R45L | FR2 | 0.529 | 181 |
| ID-A11U | 25 | F47W | FR2 | 0.175 | 89.6 |
| ID-A12U | 26 | L48V | FR2 | 0.179 | 91.5 |
| ID-A13U | 27 | A49S | FR2 | 0.615 | 54 |
| ID-A14U | 28 | Q65K | CDR2 | 0.15 | 117.4 |
| ID-A15U | 29 | V79L | FR3 | 0.146 | 84.9 |
| ID-A16U | 30 | K87R | FR3 | 0.446 | 85 |
| ID-A17U | 31 | S88A | FR3 | 0.493 | 103 |
| ID-A18U | 32 | S88T | FR3 | 0.214 | 84.9 |
| ID-A19U | 33 | G92A | FR3 | 0.188 | 92.6 |
| ID-A20U | 34 | R93V | FR3 | 0.139 | 88.3 |
| ID-A21U | 35 | Q113L | FR4 | 0.436 | 104 |

Mutations that retained high potency in the IL-7/IL-7Rα-His6-Fc ELISA and which maintained similar resistance to human faecal pools were then combined to produce 19 humanized ICVDs (Table 5).

TABLE 5

| ICVD | SEQ ID NO | Mutations | ELISA EC50 (nM) | Human faecal stability (%) | SI stability (%) |
|---|---|---|---|---|---|
| V7R-2E9 | 11 | WT | 0.6 | 103.4 | |
| ID-A23U | 36 | E44G, R45L, F47W, Q65K, K87R, S88A | 0.854 | 0 | |
| ID-A24U | 37 | R45L, F47W, Q65K, K87R, S88A | 0.819 | 87.6 | 98.3 |
| ID-A25U | 38 | E44G, F47W, Q65K, K87R, S88A | 0.835 | 66 | |
| ID-A26U | 39 | E44G, R45L, Q65K, K87R, S88A | 0.841 | 42.3 | |
| ID-A27U | 40 | E44G, R45L, F47W, K87R, S88A | 0.395 | 0 | |
| ID-A28U | 41 | E44G, R45L, F47W, Q65K, S88A | 0.46 | 48 | |
| ID-A29U | 42 | E44G, R45L, F47W, Q65K, K87R | 0.476 | 0 | |
| ID-A30U | 43 | E44G, Q65K, K87R, S88A | 0.362 | 70.7 | |
| ID-A31U | 44 | E44G, Q65K | 0.336 | 98 | 109.4 |
| ID-A32U | 45 | E44G, K87R | 0.367 | 54.6 | |
| ID-A33U | 46 | E44G, S88A | 0.429 | 85 | 92.9 |
| ID-A34U | 47 | Q65K, K87R | 0.376 | 109.2 | 98.9 |
| ID-A35U | 48 | Q65K, S88A | 0.849 | 120.3 | 83.5 |
| ID-A36U | 49 | K87R, S88A | 0.797 | 95.6 | 92.9 |
| ID-A37U | 50 | E44G, Q65K, K87R | 0.845 | 72.7 | |
| ID-A38U | 51 | E44G, Q65K, S88A | 0.789 | 87.9 | 98.6 |
| ID-A39U | 52 | E44G, K87R, S88A | 0.411 | 64.3 | |
| ID-A40U | 53 | Q65K, K87R, S88A | 0.544 | 88 | 108.9 |

Out of these 19 humanized ICVDs, Table 6 summarises the most advantageous humanized ICVDs which maintained potency and resistance to both human faecal and mouse small intestinal proteases.

TABLE 6

| ICVD | SEQ ID NO | Mutations relative to V7R-2E9 | *S. cerevisiae*-expressed equivalent (includes additional E1D mutation) | SEQ ID NO |
|---|---|---|---|---|
| ID-A24U | 37 | R45L, F47W, Q65K, K87R, S88A | ID-A43U | 35 |
| ID-A31U | 44 | E44G, Q65K | ID-A50U | 36 |
| ID-A33U | 46 | E44G, S88A | ID-A52U | 37 |
| ID-A34U | 47 | Q65K, K87R | ID-A53U | 38 |
| ID-A35U | 48 | Q65K, S88A | ID-A54U | 39 |
| ID-A36U | 49 | K87R, S88A | ID-A55U | 40 |
| ID-A38U | 51 | E44G, Q65K, S88A | ID-A57U | 41 |
| ID-A40U | 53 | Q65K, K87R, S88A | ID-A59U | 49 |
| ID-A40U | 53 | R45L, Q65K, K87R, S88A | ID-A62U | 8 |

A particularly noteworthy ICVD was ID-A62U, which includes E1D (for yeast expression, to avoid the possibility of generating a product with a cyclised N-terminal glutamate) and humanisation mutations R45L, Q65K, K87R and S88A. Another particularly noteworthy ICVD was ID-A59U, which includes E1D, Q65K, K87R and S88A. ID-A59U has a pl of 5.1 and a molecular weight of 12.966 kDa (pl and molecular weight calculated using CLC Sequence Viewer).

Example 7: Potency Assays Performed on Humanised V7R-2E9 Variants

The inhibitory potency and efficacy (maximal inhibition) of ID-A40U (produced in *E. coli*) was confirmed in vitro in the IL-7/IL-7R neutralisation ELISA and the IL-7 induced STAT5 phosphorylation assay in human PBMCs. $EC_{50}$ values were generated in Graphpad prism using the ELISA signal blank corrected $A_{450}$ data and 'log(inhibitor) vs. response—Variable slope (four parameters)' to fit curves and generate $EC_{50}$.

The results are shown in Table 7a, alongside comparators.

TABLE 7a

| Construct | IL-7/ IL-7R ELISA $EC_{50}$ nM | IL-7 induced pSTAT5 in hPBMCs $EC_{50}$ nM |
|---|---|---|
| ID-A40U | 0.544 | 1-2 |
| V7R-2E9 | 0.818 | 2.86 |
| mAb829 | 0.8 | 2.6 |

In separate experiments, these same assays were performed on ID-A62U (produced in *S. cerevisiae*) alongside comparators. The results are shown in Table 7b and FIG. 4.

TABLE 7b

| Construct | IL-7/ IL-7R ELISA $EC_{50}$ nM |
|---|---|
| ID-A62U | 0.4 |
| mAb829 | 0.424 |

The ability of ID-A62U to neutralise the L-TSLP/TSLP-R complex binding to IL-7Rα was tested in the manner described above under Example 4, alongside mAb829. The results are shown in Table 7c below. A subtraction was performed on the data set before graphing which normalised to the highest concentration of antibody tested (to overcome a high level of background on the plate).

TABLE 7c

| Construct | TSLP/ TSLPR/ IL-7R ELISA EC$_{50}$ nM |
|---|---|
| ID-A62U | 0.74 |
| mAb829 | 0.99 |

In summary, ID-A62U and ID-A40U were demonstrated to have comparable or greater potency than comparator clinical anti-IL-7R antibody mAb829.

Example 8: Biacore Estimation of ICVD— IL-7R Binding Affinity

The binding kinetics of ID-A40U were compared against the mAb829 clinical antibody in a Biacore study. The IL-7Rα-His$_6$-Fc was coated directly on the Biacore sensor plate (for mAb829 analysis) or captured by an anti-human IgG Fc (for the ICVD analysis), and ICVD/Ab were flowed over the plate to detect binding. ID-A40U had an affinity (Ko) of $7.8\times10^{-11}$ M, and mAb829 had a slightly lower affinity (Ko) of $5.67\times10^{-10}$ M. The results indicate that ID-A40U demonstrates strong binding to the antigen.

Example 9: Cross-Reactivity with IL-7Rα from Toxicological Species

Cross-reactivity of ID-A40U, ID-A59U and ID-A62U binding to IL-7Rα from toxicological species was investigated.

96-well plates were coated with 0.5 µg/mL recombinant human IL-7Rα His$_6$-Fc+5 µg/mL BSA and then blocked. 0.5 nM of ICVD was mixed 1:1 with the test compounds of choice serially diluted in 1% BSA, then incubated for 30 minutes to allow binding before adding to the IL-7Rα coated plates. Following 2 hours incubation, bound ICVD was detected with 50 uL/well ½₀₀₀₀ anti-FLAG-HRP Goat antibody (GeneTex, GTX21238), and the level of neutralisation of ICVD-IL-7Rα binding by the test compounds was determined.

Figure 5:
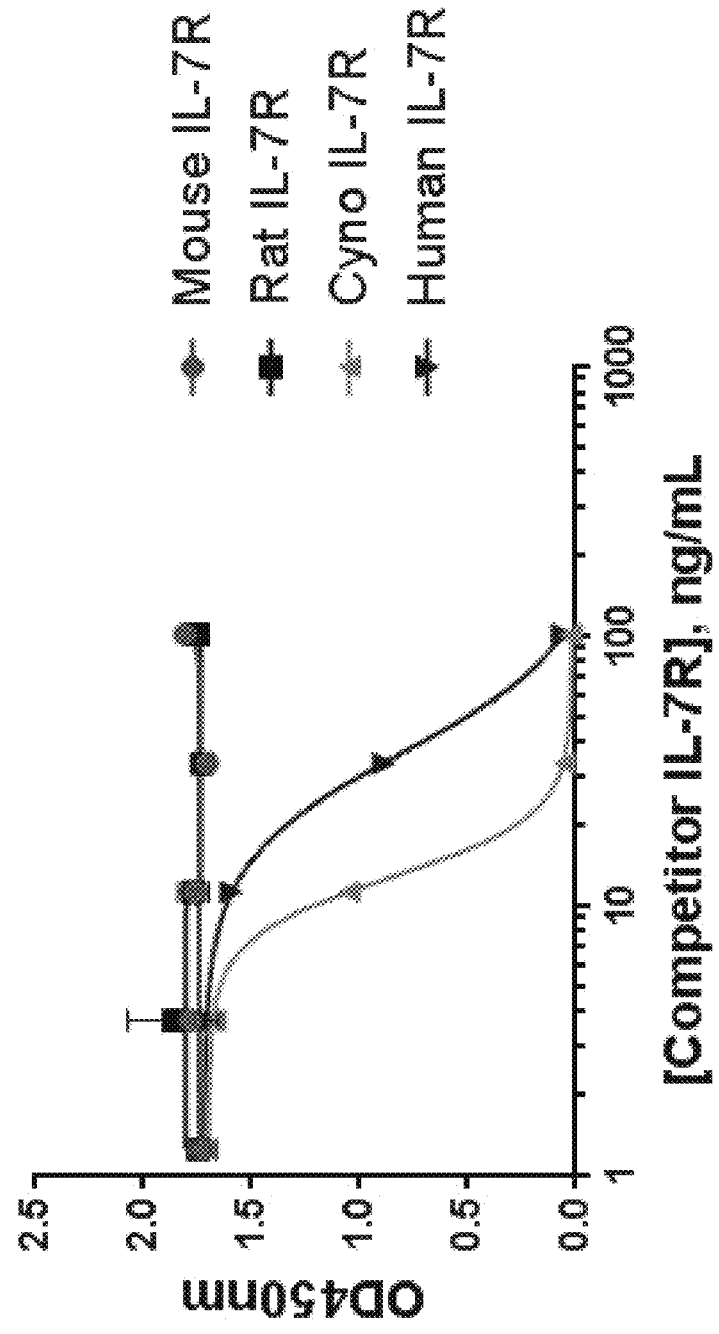
Figure 6:
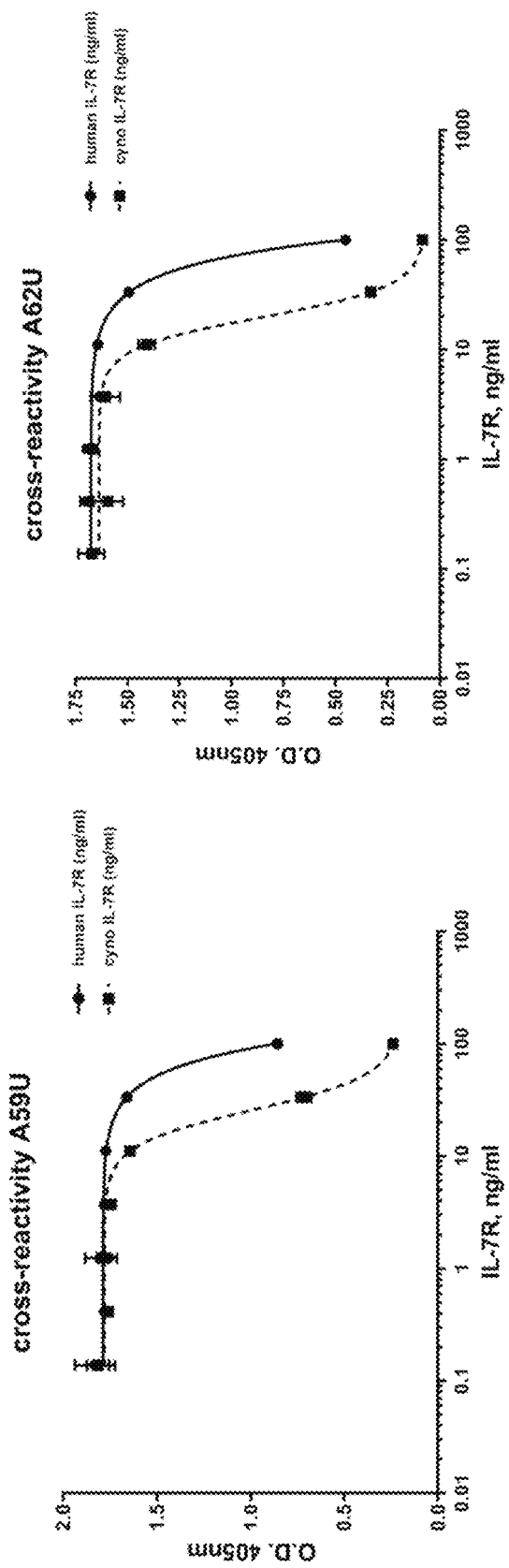
FIG. 6—Cross-reactivity of ID-A59U and ID-A62U with human and cynomolgus IL-7Rα

It was found in this assay that murine IL-7Rα did not interfere with ICVD/IL-7Rα binding indicating that mouse or rat would be unsuitable species for toxicological studies. However, cynomolgus monkey IL-7Rα did interfere with these ICVDs binding to human IL-7Rα (FIGS. 5 and 6), making the cynomolgus monkey a suitable toxicology species for these ICVDs and related ICVDs.

Example 10: Specificity Against Non-Target Cytokines

Figure 7:
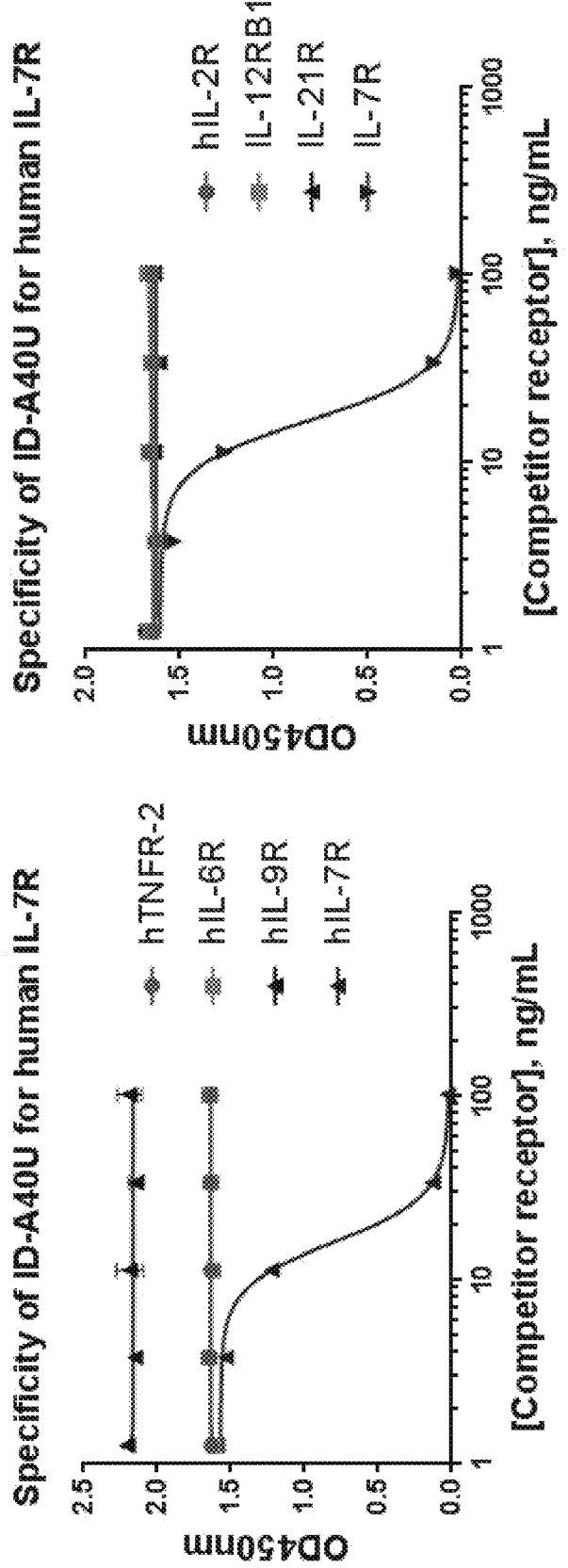
FIG. 7—Specificity of ID-A40U for human IL-7Rα

ID-A40U was tested for selectivity against proteins related to human IL-7Rα, substantially in the manner described above under Example 9. Human IL-12Rβ1 and human IL-12Rβ2 were found to be the most closely related human proteins to IL-7Rα identified using the NCBI BLASTp tool, with a sequence identity with IL-7Rα of 29% and 30% respectively. In a competition IL-7R binding ELISA assay, the hIL-12Rβ1 and a selection of receptors within the IL-7R family (IL-2R, IL-21R, and IL-9R) or not related receptors (TNFR-2 and IL-6R) were tested for their ability to inhibit binding of ID-A40U to human IL-7Rα immobilized on a plate. None of human IL-12Rα1, IL-2R, IL-21R, IL-9R, TNFR-2, or IL-6R interfered with ID-A40U binding to IL-7Rα, while addition of an increasing amount of human IL-7Rα produced a dose-dependent curve (FIG. 7). This indicated that binding of ID-A40U ICVD to off-target molecules would be very unlikely in humans.

Example 11: Resistance to Gastrointestinal Extracts

Ex vivo incubation in intestinal supernatants can predict the stability of ICVDs in the intestinal tract of cynomolgus monkeys and man. The activities of the major small intestinal proteases, trypsin and chymotrypsin, are conserved across mammalian species, whereas proteases present in the large intestine are likely to be produced by host species-specific gut microflora. To generate testing matrices that reflect these two environments, pooled mouse small intestinal supernatants and pooled faecal supernatants were prepared. Both of these matrices are highly digestive towards unselected, un-engineered ICVDs.

It has previously been shown that the ICVD ID-38F has high stability in these matrixes (see WO2016/156465) and that this property was predictive of high stability during transit through the gut for ID-38F.

Figure 8:
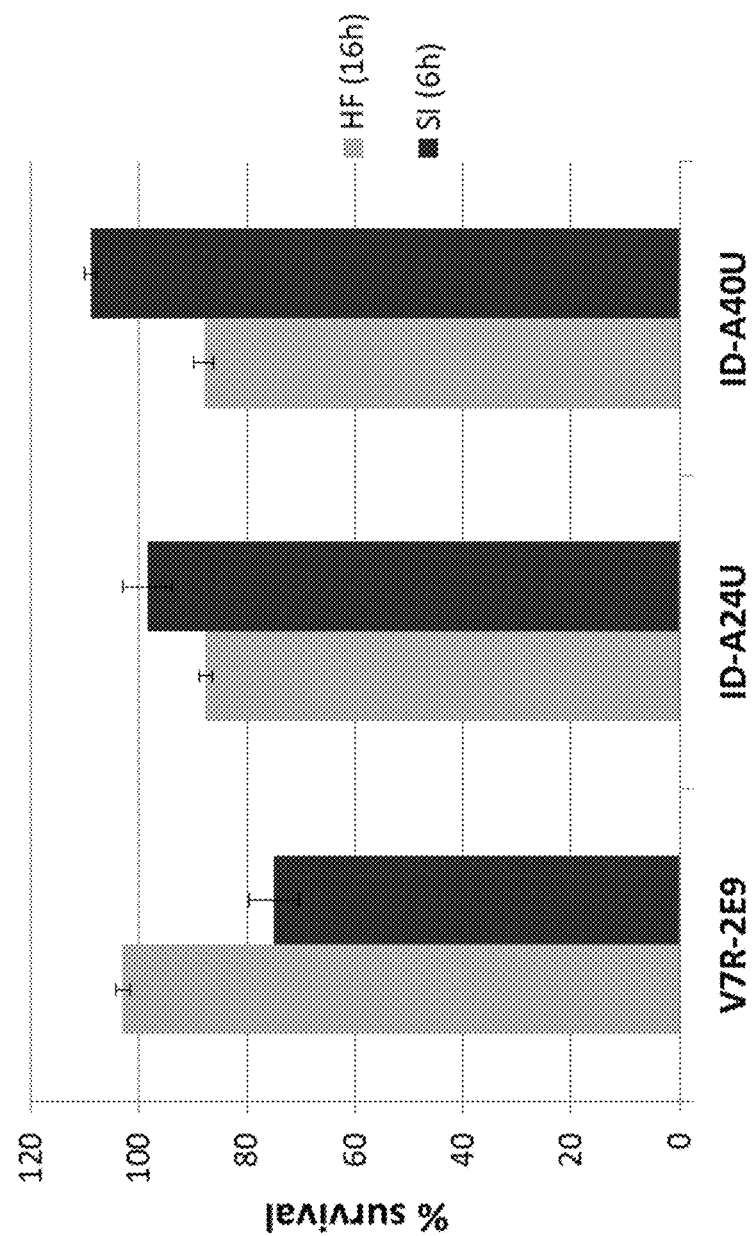
FIG. 8—Percentage survival of V7R-2E9, ID-A24U and ID-A40U in digestive matrices FIG. 9—Percentage stability of ID-A62U and ID-A41U in human faecal supernatant FIG. 10—Digestion by MMPs of etanercept, mAb829 and A40U-F/H FIG. 11—Expected concentration in undiluted faecal supernatants (ID-A24U vs ID-A40U vs ID-38F)

V7R-2E9, ID-A24U and ID-A40U were tested for their survival in gastrointestinal extracts from both murine and human sources. ICVDs were incubated for 6 hours at 37° C. with mouse small intestinal supernatants, and 16 hours with human faecal supernatant. Survival was measured by the IL-7/IL-7R neutralising ELISA. All constructs demonstrated good survival in all digestive matrices tested (FIG. 8, wherein "SI"=mouse small intestinal fluid and "HF"=human faecal supernatant). ID-A40U contains the same functional mutations as yeast-produced ID-A59U.

Figure 9:
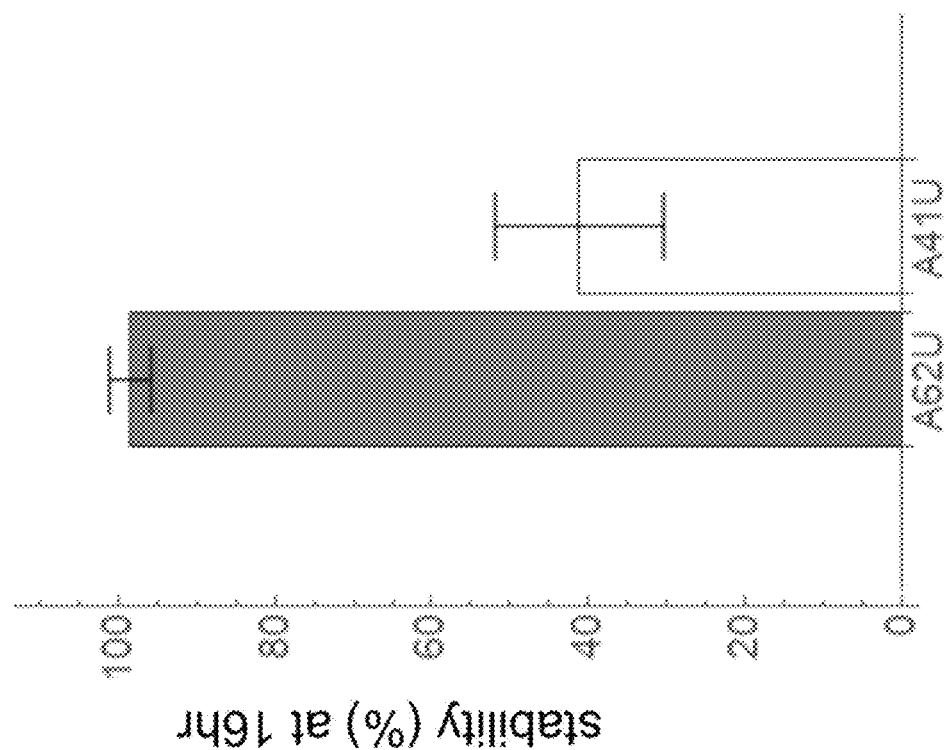

In a separate experiment, ID-A62U was tested for survival in the same human faecal supernatant assay, alongside ID-A41U (an unstable comparator ICVD). ID-A62U displayed approximately 100% survival compared to approximately 40% survival for ID-A41U (FIG. 9).

These were stringent tests involving extended incubation periods. Therefore, any of these ICVDs would be expected to survive very well in the gastrointestinal environment.

Example 12: Resistance to Gastrointestinal Matrix Metalloproteases

Levels of activated matrix metalloproteases (MMPs) are increased in the inflamed mucosa of patients with intestinal bowel disease. These MMPs are able to digest native human IgG and therapeutic agents that contain a human IgG scaffold (Biancheri et al 2015). In the case of the anti-TNFα therapy etanercept, this digestion causes a significant reduction in TNFα neutralising potency. To confirm that ID-A40U is resistant to MMPs, ID-A40U along with mAb829 and Enbrel were detected by Western blotting following incubation for 22 hours at 37° C. in the presence of human MMP3, MMP12 or TCNB buffer. Enbrel and mAb829 were detected by peroxidase-conjugated anti-human IgG specific for Gamma-chains. ID-A40U and TCNB buffer-only controls were detected with pAb 1219 primary Rabbit α-ICVD and secondary HRP-conjugated pAb SwineaRabbit.

Figure 10:
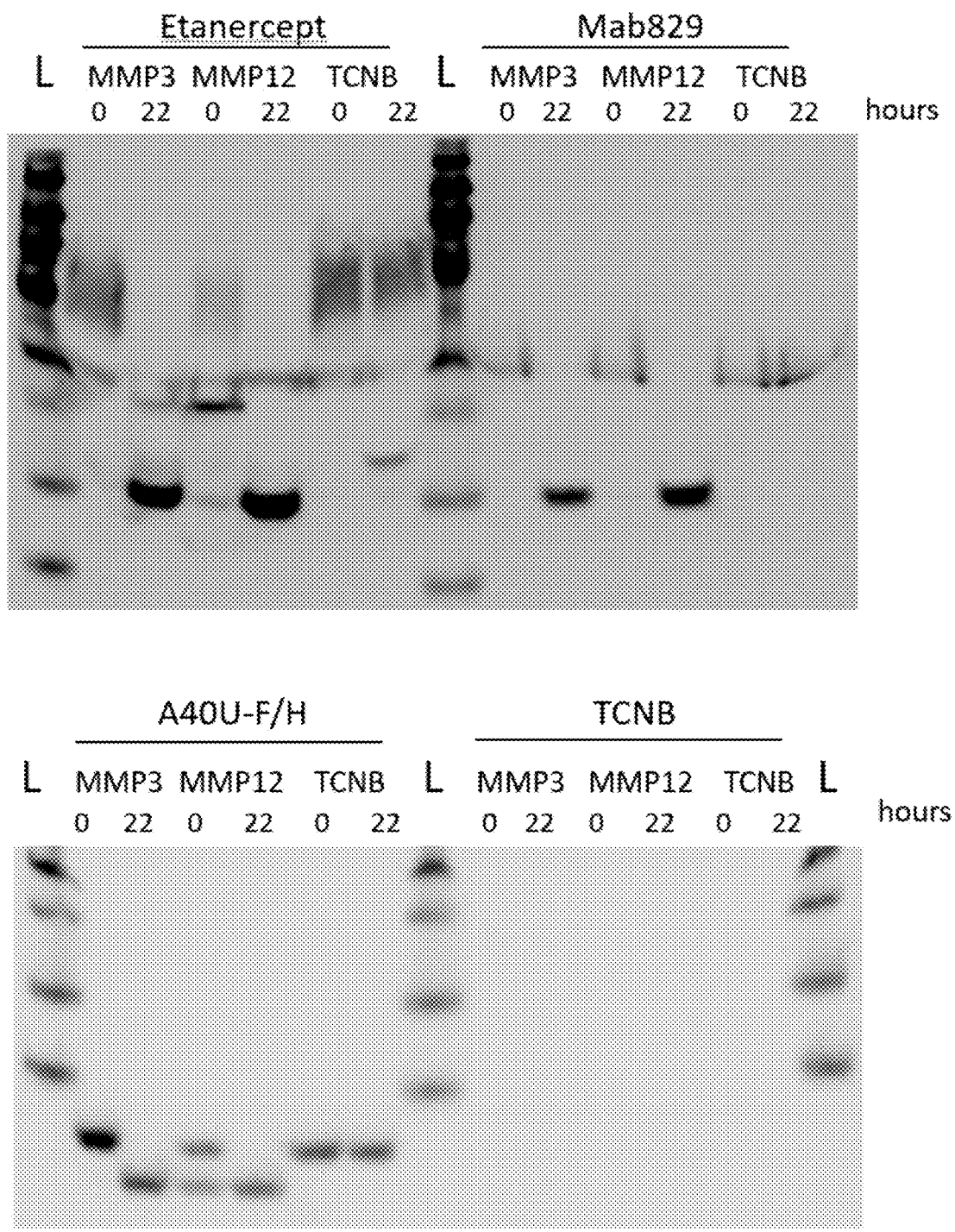
Figure 11:
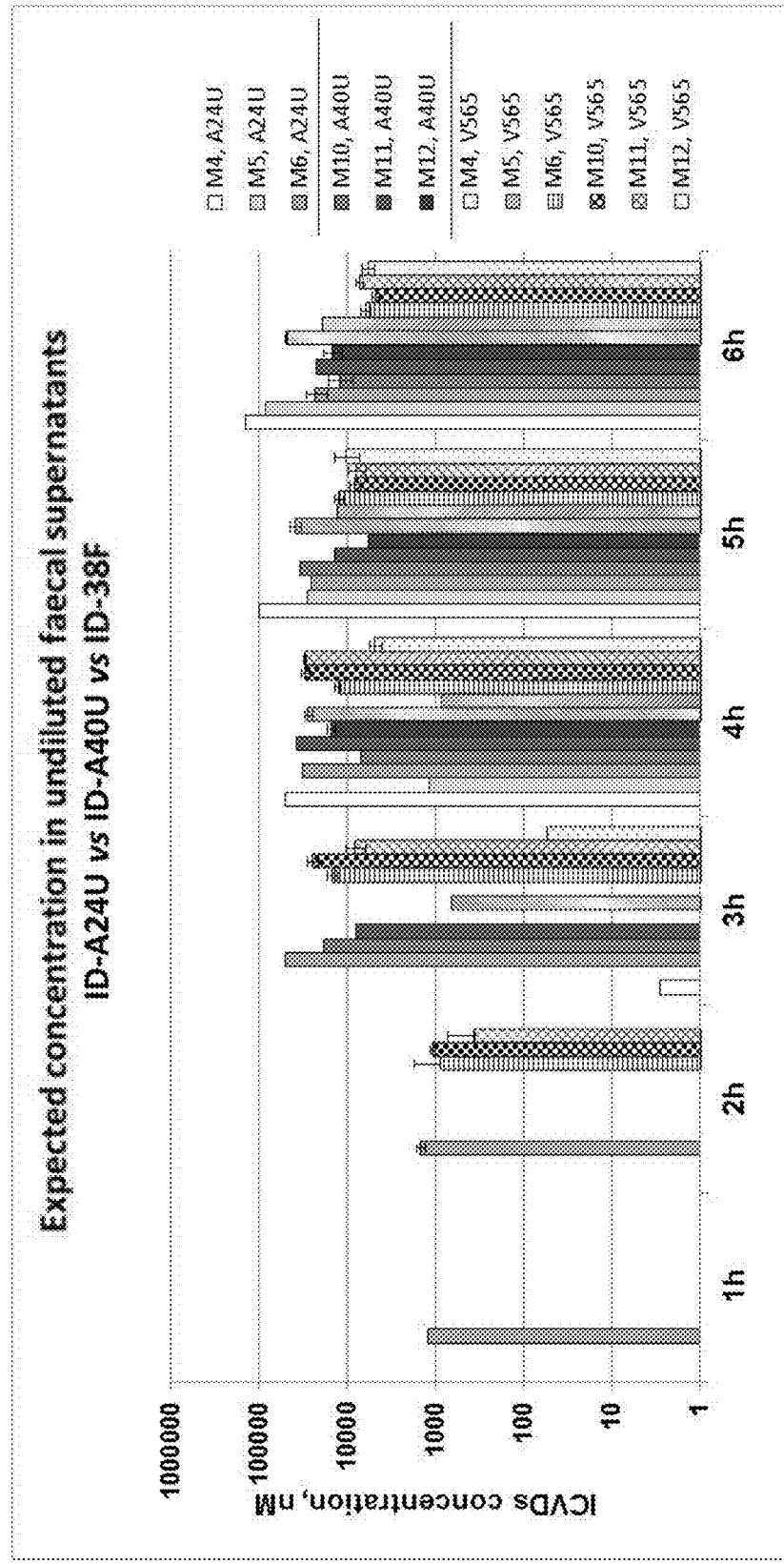
Figure 12:
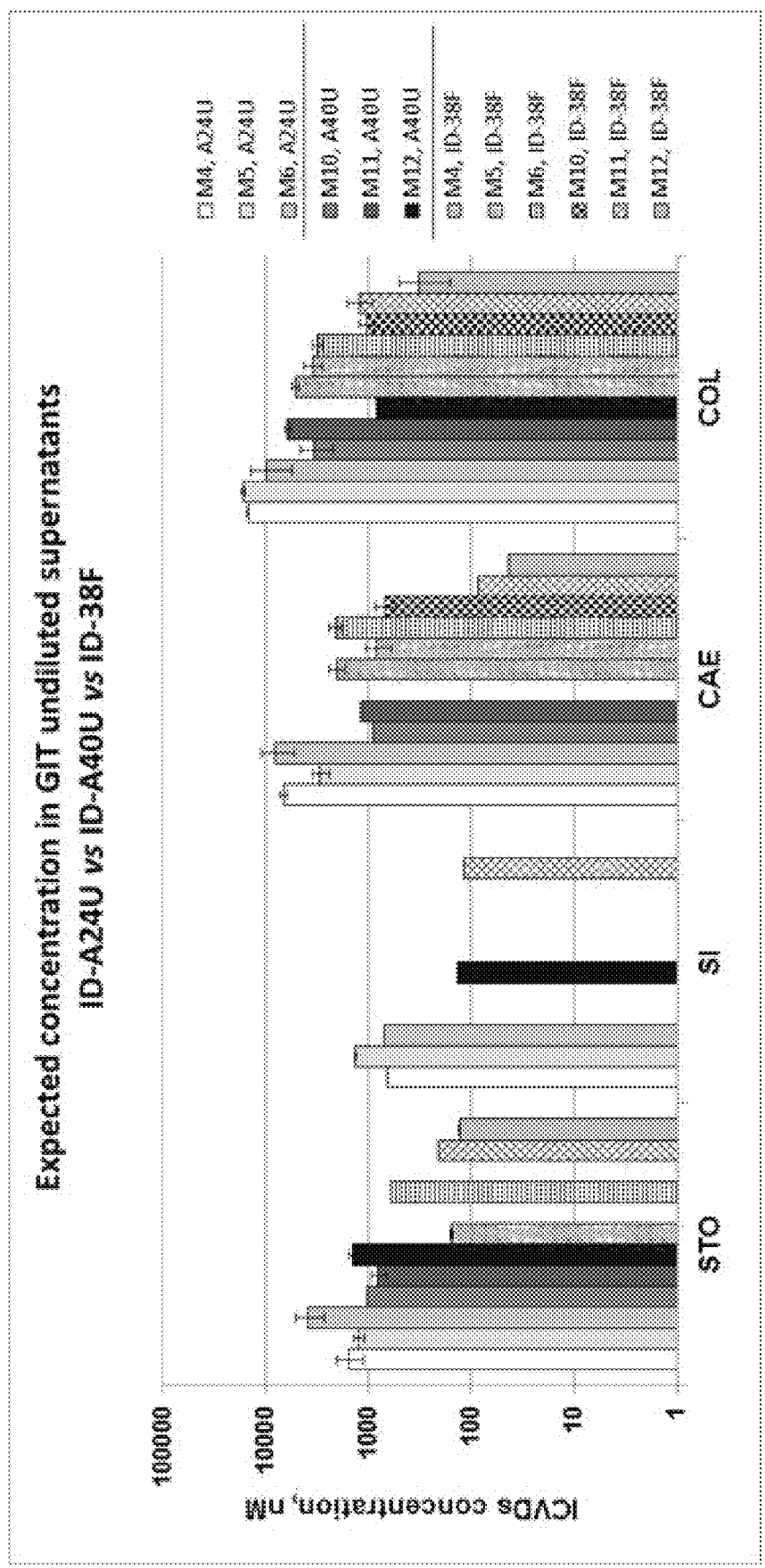
FIG. 12—Expected concentration in GIT undiluted supernatants (ID-A24U vs ID-A40U vs ID-38F)
Figure 13:
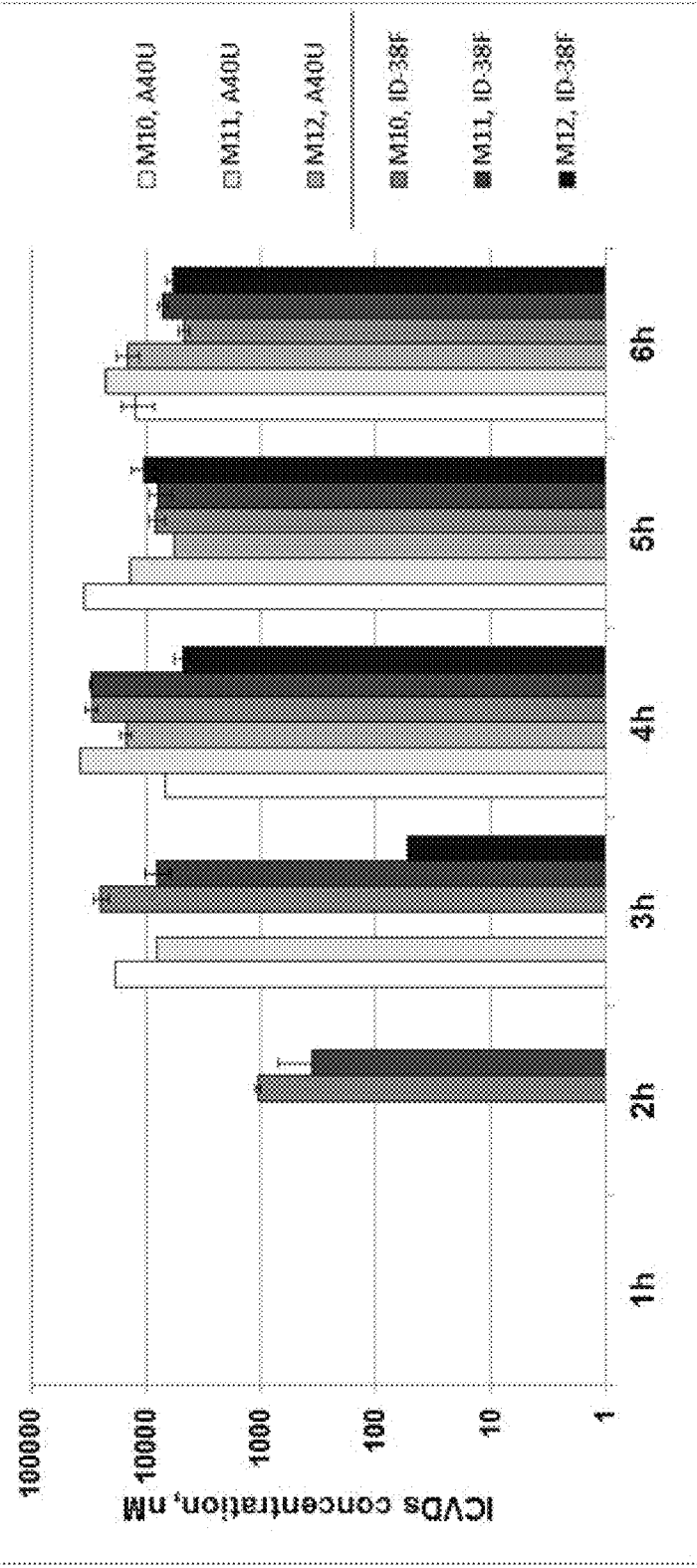
FIG. 13—Expected concentration in undiluted faecal supernatants (ID-A40U vs ID-38F)
Figure 14:
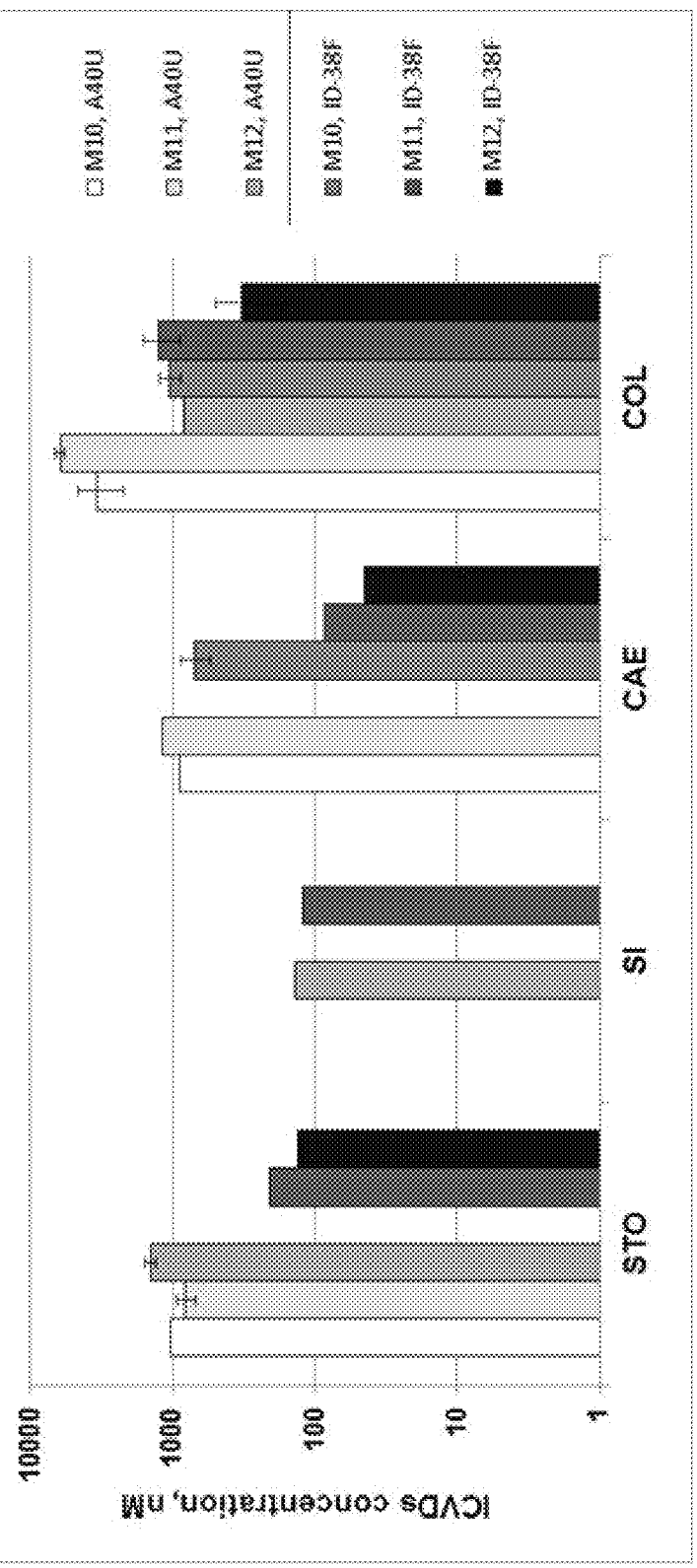
FIG. 14—Expected concentration in GIT undiluted supernatants (ID-A40U vs ID-38F)
Figure 15:
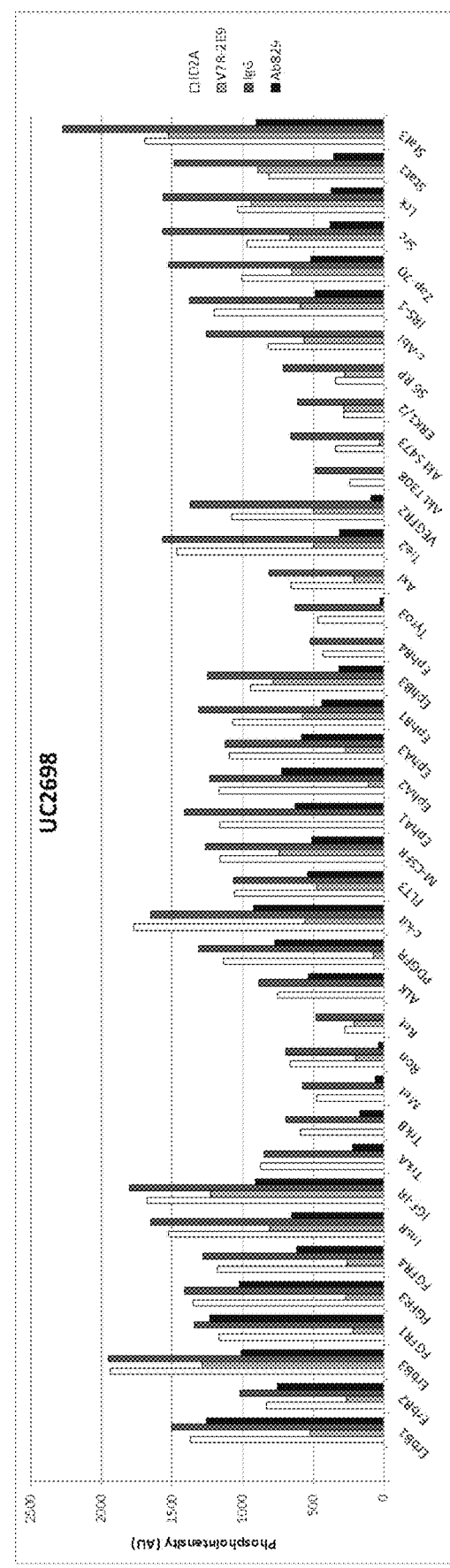
FIG. 15-18—Human IBD tissue protein phosphorylation profiles
Figure 16:
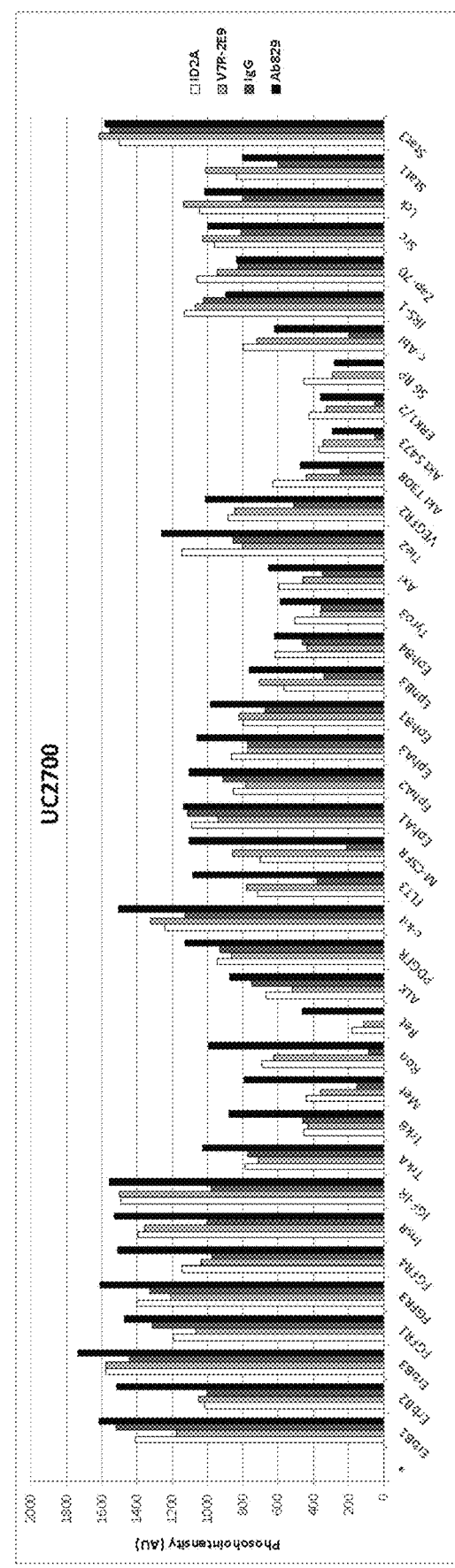
Figure 17:
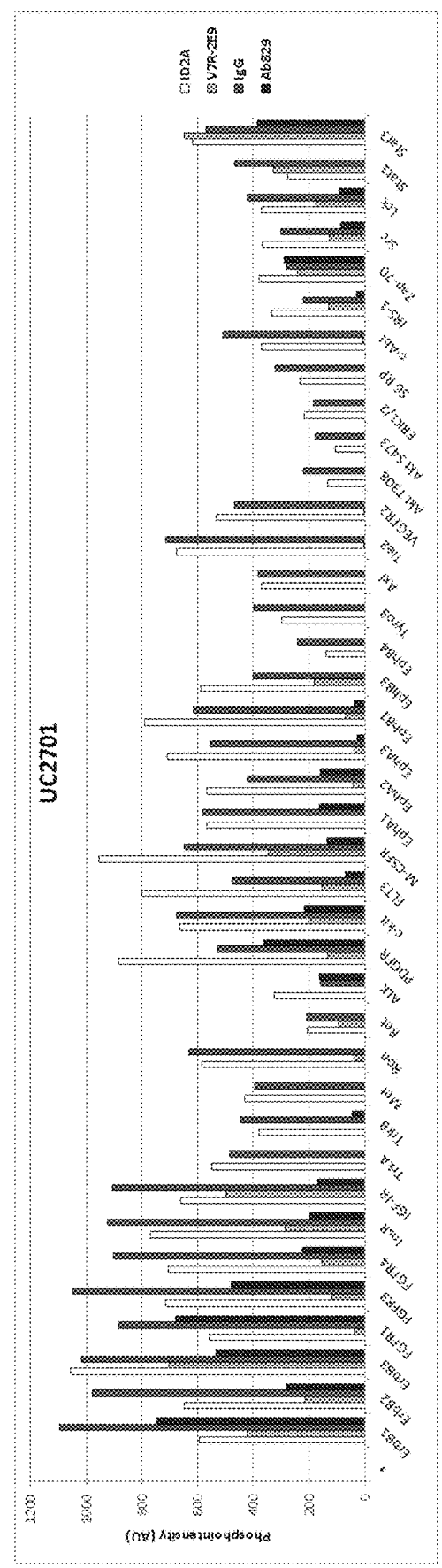
Figure 18:
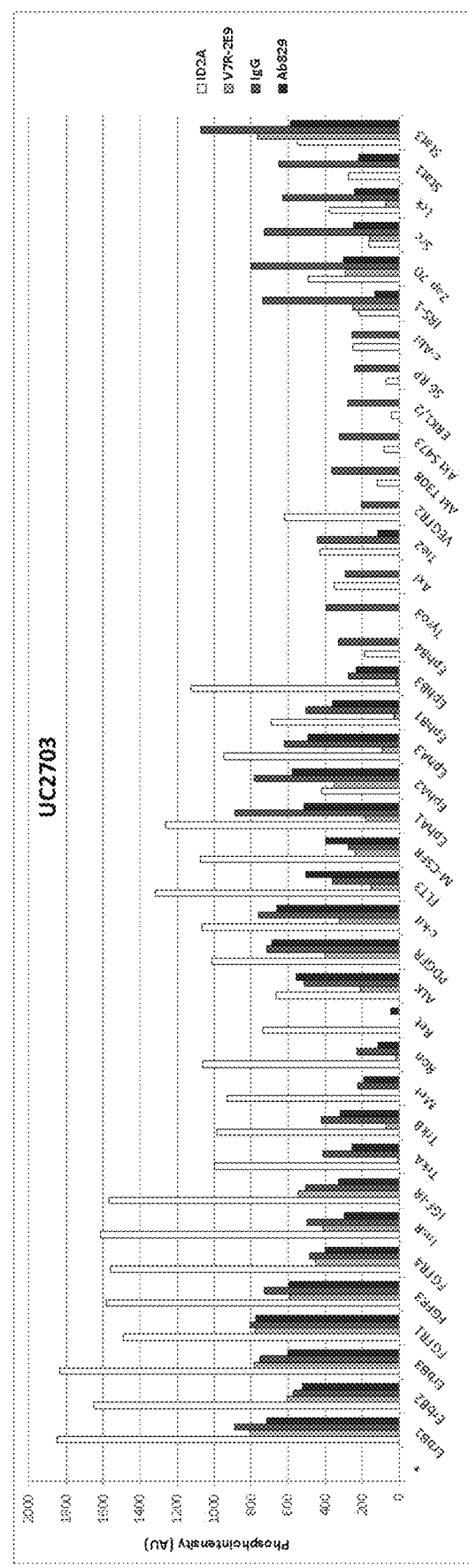
Figure 19:
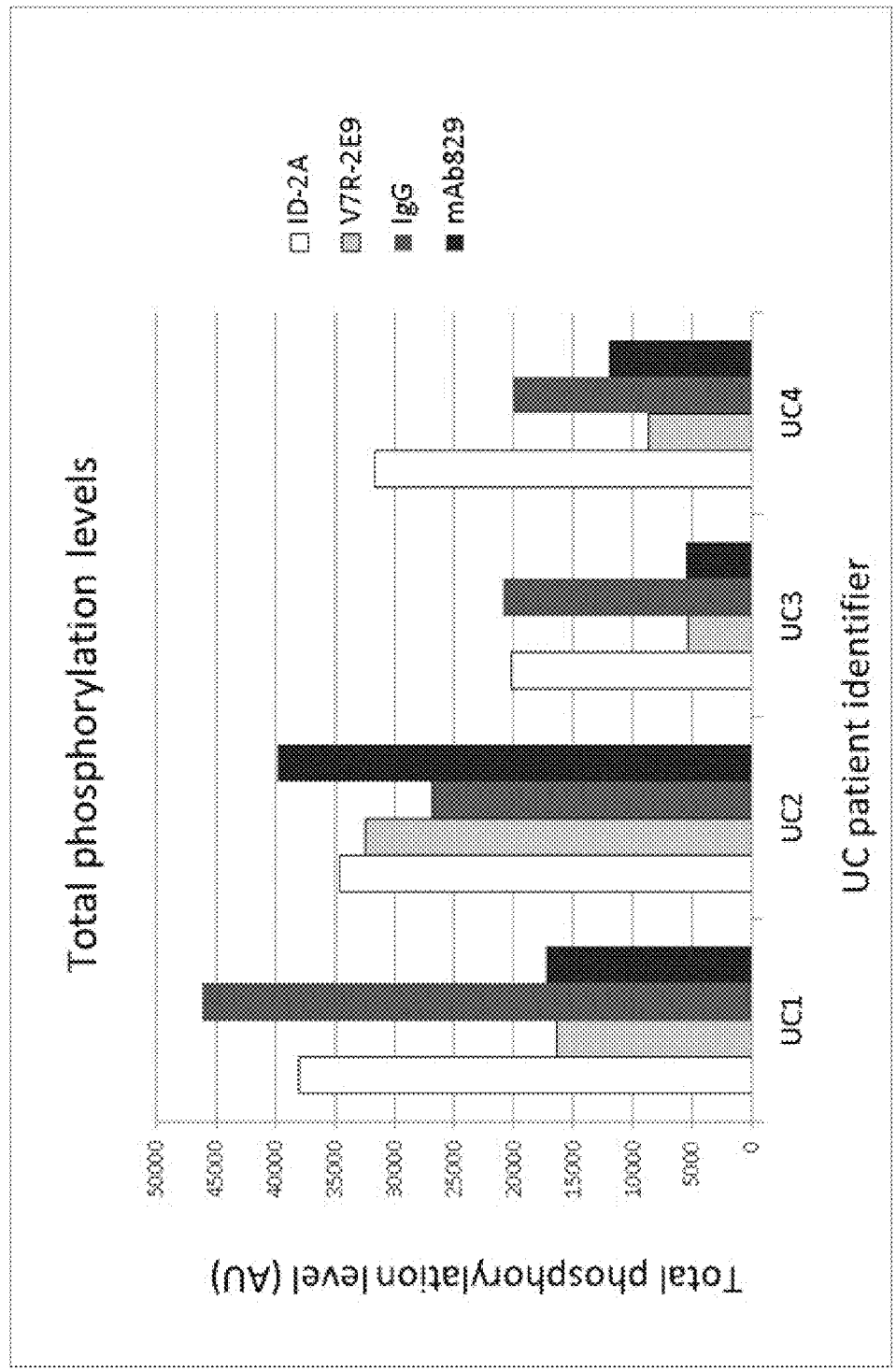
FIG. 19—Total phosphorylation levels

Following incubation, ID-A40U was not digested by the MMPs, as measured by Western blotting (FIG. 10), showing a band with a molecular weight corresponding to the expected full length ICVD (lacking the Flag-His$_6$ tag which is cleaved off during the digestion). However, after the same incubation time, MMP3 and MMP12 digested full-length etanercept and mAb829 to smaller fragments. Following MMPs incubation ID-A40U was shown to be fully potent at neutralising IL-7R, as measured using the IL7/1L-7R functional ELISA. 'F/H' in FIG. 10 denotes the presence of a FLAG/His tag.

Example 13: Transit and Survival in the Mouse Gastrointestinal Tract

Results of in vitro studies described above showed that the optimised V7R-2E9-derivatives were resistant to inactivation by proteases present in a supernatant extract prepared from mouse small intestinal contents. A subsequent study was performed to investigate the stability of ID-A24U and ID-A40U during passage through the gastrointestinal system of the mouse.

Both ID-A24U and ID-A40U were formulated with ID-38F (an anti-TNFα ICVD, see WO2016/156465) in a milk and bicarbonate mixture to protect against denaturation at low pH and digestion by pepsin in the stomach. Following administration of the ICVDs to mice by oral gavage, concentrations of the ICVDs in stomach, small intestine, caecum and colon were determined at 6 hours post-dosing. In addition, the ICVD concentration of faecal pellets collected at hourly intervals was measured.

ID-A24U and ID-A40U were measured in the faeces collected between 4 h and 6 h post-dosing from all mice, with ID-A40U being measured also in the 3 h time point from 2 mice (FIG. 11). ID-A24U was, instead, measured in the faeces collected from mouse 6 (M6) during the first 3 hours indicating that in this mouse the transit was particularly fast in comparison to the other mice.

These results suggest that both ID-A24U and ID-A40U can survive transit through the mouse GI tract. Overall, the transit time of ID-A24U and ID-A40U looks quite similar, with the exception of 1 mouse within each group (M6 and M12). At the time of culling (6 h) most of the ID-A24U and ID-A40U were present in the caecum (CAE) and colon (COL) of all the mice with reasonably high amounts still measured in the stomach (STO) and small intestine (SI). Based on the concentrations calculated taking into account the dilution factor used for the slurries preparation, the expected concentration of ID-A24U and ID-A40U at the time of culling is between 22.7 μM-140 μM and 12 μM-22.5 μM respectively in the faeces (FIG. 11). The expected concentration of ID-A24U in the caecum and colon are between 2.9 μM-8 μM and 9.7 μM-16.5 μM respectively. The expected concentration of ID-A40U in the caecum and colon are between 0.9 μM-1.2 μM and 0.8 μM-6.2 μM respectively (FIG. 12).

The ID-38F used as control in this study was measured at high levels in all the faecal and lower GIT samples as previously observed. Expected concentration of ID-38F at the 6 h time point varied in the 6 mice between 0.04 μM-2.1 μM in the caecum, 0.33 μM-5.1 μM in the colon, and 4.9 μM-48 μM in the faeces. Repeat experiments was performed on ID-A40U and ID-38F. Similar results were obtained (FIGS. 13 and 14).

Overall, these results indicate that ID-A24U and ID-A40U survive well and similarly to ID-38F in transiting though the mice delivering high concentrations of active ICVD to the caecum and colon. This likely reflects the relative stability of each ICVD in these gut compartments previously observed in vitro. ID-A24U and ID-A40U were shown to be stable in the mouse small intestine. It is therefore expected that these and related ICVDs will have high stability in the human GI tract.

Example 14: Human IBD Tissue Studies

A study was conducted to investigate the activity of the V7R-2E9 in a human ex vivo model, reproducing the inflammatory bowel disease tissue environment. V7R-2E9 and controls (ID-2A, an anti *C. difficile* toxin ICVD; mAb829, and IgG1k (a non-IL-7R binding purified human IgG1k isotype control recombinant antibody) were tested in ex vivo cultures for their effects on tissue phosphoprotein levels and the production of inflammatory cytokines using tissue taken from four patients with active ulcerative colitis.

Analysis of tissue lysates on Pathscan phosphoprotein arrays (FIGS. 15-18) showed that in biopsies from three of the four UC patients, V7R-2E9 treatment inhibited the phosphorylation of a substantial proportion of the 39 proteins detected on the array, when compared with the corresponding ID-2A-treated biopsies. mAb829 also inhibited protein phosphorylation levels in biopsies from the same three UC patients and the patterns of inhibition obtained appear to be similar to those achieved with V7R-2E9. A total phosphorylation intensity value for each biopsy was calculated from the intensities of all 39 phosphoproteins on the array. Results presented in FIG. 19 shows that V7R-2E9 and mAb829 inhibited total phosphorylation levels in biopsies from the three responsive UC patients but had little or no effect on total phosphorylation in the biopsies from patient UC2700. This patient had active disease while receiving azathioprine (a T cell inhibitor) as part of their medication, so resistance to T cell directed therapy would be a possible explanation for the lack of response to antibodies (V7R-2E9 and mAb829) that targeted IL-7R-mediated T cell activation.

Analysis of culture media from the patient UC2698, UC2701 and UC2703 biopsies showed that V7R-2E9 treatment also inhibited the production of several cytokines including IL-1β, IL-6, IL-8 and TNFα but was without effect on the production of the anti-inflammatory cytokine IL-10 (data not shown). Consistent with the results of the phosphoprotein analysis, V7R-2E9 did not inhibit the production of pro-inflammatory cytokines in the biopsy cultures of patient UC2700.

In conclusion, antagonism of IL-7R in UC biopsy tissue by V7R-2E9 inhibited the phosphorylation of signalling proteins and the production of cytokines and chemokines that are associated with pro-inflammatory and immunoregulatory pathways. Results demonstrated that the antagonism of mucosal IL-7R+ve T cells by V7R-2E9 (and mAb829) can inhibit inflammatory processes in a model that is closely related to the disease environment.

Example 15: Yeast Productivity in Fermentation Culture

*S. cerevisiae* expressing ID-A59U was inoculated into a 5 litre ethanol-fed fermentation. End of fermentation (EoF) broth supernatant was analysed for ID-A59U concentration by SDS-PAGE and IL-7/IL-7Rα-His6-Fc functional ELISA. SDS-PAGE indicated a high yield of 2 g/L and the functional ELISA confirmed that ID-A59U is fully active in the EoF and the final yield is at least 1.5 g/L. *S. cerevisiae* expressing ID-A62U was inoculated into a 50 mL shake flask expression system. High yields of ICVD were obtained.

Conclusions from Examples Above

Polypeptides benefiting from high potency in cellular assay systems measuring the neutralisation of IL-7Rα activities have been identified, including inhibition of IL-7 and/or L-TSLP binding to IL-7Rα. These polypeptides also benefit in some instances from high stability in the small intestine and/or human faecal supernatant. Humanised derivatives of one particular polypeptide, V7R-2E9, were produced which substantially retained potency, or benefitted from increased potency, compared to unmodified V7R-2E9—while also retaining resistance to intestinal proteases and the ability to be effectively produced in *S. cerevisiae*. The most favourable combination of mutations to V7R-2E9 (R45L, Q65K, K87R, S88A), including the E1D yeast production mutation, is embodied by ID-A62U.

Miscellaneous

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

REFERENCES

The references below are herein incorporated by reference in their entirety.

Arbabi-Ghahroudi et al *FEBS Lett* 1997 414:521-526
Baumgart et al *The Lancet* 2012 380(9853):1590-605
Bjerkan et al *Pharmaceuticals* (Basel). 2016 9(3). pii: E41
Blattler et al *Biochemistry* 1985 24:1517-1524
Chomezynnski and Sacchi *Anal Biochem* 1987 162:156-159
Cianferoni and Spergel *Curr Allergy Asthma Rep.* 2015 15(9):58
Corren et al *N Engl J Med.* 2017 377(10):936-946
Crawley et al *J Immunol.* 2010 184(9):4679-4687
Danese *Gut* 2012 61:918-932
Desmet et al *Nature Communications* 2014 5:5237
Dooms *J Autoimmun.* 2013 45:40-48
Ebersbach et al. *J. Mol. Biol.* 2007 372 (1): 172-185
Ellis et al Br *J Clin Pharmacol.* 2019 85(2): 304-315
Faisst et al *J Virol* 1995 69:4538-4543
Fornasa et al *J Allergy Clin Immunol.* 2015 136(2):413-422
Frenken et al *J Biotech* 2000 78:11-21
Fry & Mackall *Blood* 2002 99(11):3892-3904
Fry & Mackall *J Immunol.* 2005 174(11):6571-6576
Goldberg et al *Nat Rev Gastroenterol Hepatol* 2015 (5):271-283
Goldberg et al *Protein Eng Des Sel.* 2016 29(12):563-572
Green and Sambrook Molecular Cloning: A Laboratory Manual 2012 4th Edition Cold Spring Harbour Laboratory Press
Griffiths et al *Antibodies* 2013 2:66-81
Grundstrom et al *Nucl. Acids Res* 1985 13:3305-3316
Hafler et al *N Engl J Med.* 2007 357(9):851-862
Hamers-Casterman et al *Nature* 1993 363(6428):446-448
Harmsen et al *Gene* 1993 125:115-123
Harmsen et al *Appl Microbiol Biotechnol* 2007 77(1):13-22)
Hendrickson et al *Clin Microbiol Rev* 2002 15(1):79-94
Heninger et al *J Immunol.* 2012 189(12):5649-5658
Hoogenboom et al *Nucl Acid Res* 1991 19:4133-4137
Huse et al *Science* 1989 246 (4935):1275-1281
Johnson et al *Anal. Chem.* 2012 84(15):6553-6560
Kabat et al Sequences of Proteins of Immunological Interest, Fifth Edition U.S. Department of Health and Human Services, 1991 NIH Publication Number 91-3242
Kohler and Milstein *Nature* 1975 256:495-497
Koide and Koide *Methods Mol. Biol.* 2007 352: 95-109
Krehenbrink et al *J. Mol. Biol.* 2008 383 (5):1058-1068
Ling et al *Anal Biochem* 1997 254(2):157-178
Lipovsek *Protein Eng Des Sel.* 2011 24(1-2):3-9
Liu *J Exp Med* 2006 203(2):269-273
Liu et al *Nat Med.* 2010 16(2):191-197 (retraction in: *Nat Med.* 2013 19(12):1673)
McCoy et al *Retrovirology* 2014 11:83
Merchlinsky et al *J. Virol.* 1983 47:227-232
Miethe et al *J Biotech* 2013 163(2):105-111
Muyldermans et al *Protein Eng* 1994 7(9):1129-1135
Muyldermans *Annu Rev Biochem* 2013 82:775-797
Nambiar et al *Science* 1984 223:1299-1301
Nelson et al *Molecular Pathology* 2000 53(3):111-117
Nguyen et al *Adv Immunol* 2001 79:261-296
Nixon and Wood *Curr Opin Drug Discov Devel.* 2006 9(2):261-268
Noti et al *Nat Med.* 2013 19(8):1005-1013
Nygren *FEBS J.* 2008 275(11):2668-2676
Padlan *Mol lmmunol* 1994 31:169-217
Peters et al *Immunol Lett.* 2015 172:124-131
Rimoldi et al *Nat lmmunol.* 2005 6(5):507-514
Rose et al *J Immunol.* 2009 182(12):7389-7397
Roux et al *Proc Natl Acad Sci USA* 1998 95:11804-11809
Sandborn et al *N Engl J Med.* 2007 357:228-238
Sakamar and Khorana *Nucl. Acids Res* 1988 14:6361-6372
Shealy et al *mAbs* 2010 2:428-439
Silverman et al *Nat. Biotechnol.* 2005 23(12):1556-1561
Skerra et al *Science* 1988 240(4855):1038-1041
Skerra et al *FEBS J.* 2008 275 (11): 2677-83
Suderman *Protein Expression and Purification* 2017 134: 114-124
Tanha et al *J Immunol Methods* 2002 263:97-109
Teutsch et al *Eur J Hum Genet.* 2003 11(7):509-515
Thomassen et al *Enzyme and Micro Tech* 2002 30:273-278
Tsilingiri et al *Cell Mol Gastroenterol Hepatol.* 2017 3(2): 174-182
Verma and Eckstein *Annu Rev Biochem* 1998 67:99-134
Verstraete et al *Nat Commun.* 2017 8:14937. doi: 10.1038/ncomms14937
Vetter & Neurath *Therap Adv Gastroenterol.* 2017 10(10): 773-790
Walsh *Immunol Rev.* 2012 250(1):303-316
Ward et al *Nature* 1989 341:544-546
Wells et al *Gene* 1985 34:315-323

The invention claimed is:

1. A VHH that binds to IL-7R, wherein the VHH comprises:
    (a) a complementarity determining region 1 (CDR1) comprising an amino acid sequence as set forth in SEQ ID NO: 1, a complementarity determining region 2 (CDR2) comprising an amino acid sequence as set forth in SEQ ID NO: 2, and a complementarity determining region 3 (CDR3) comprising an amino acid sequence as set forth in SEQ ID NO: 3; or
    (b) a CDR1 comprising an amino acid sequence as set forth in SEQ ID NO: 71, a CDR2 comprising an amino acid sequence of any one as set forth in SEQ ID NOs: 72, 73, 74, or 75, and a CDR3 comprising an amino acid sequence of any one as set forth in SEQ ID NOs: 77 or 78;
wherein the VHH binds IL-7R.

2. The VHH of claim 1, wherein: the CDR1 comprises the amino acid sequence as set forth in SEQ ID NO: 1, the CDR2 comprises the amino acid sequence as set forth in SEQ ID NO: 2, and a complementarity determining region 3 (CDR3) comprising an amino acid sequence as set forth in SEQ ID NO: 3, wherein the VHH binds IL-7R.

3. The VHH of claim 1, wherein: the CDR1 comprises the amino acid sequence as set forth in SEQ ID NO: 71, the CDR2 comprises the amino acid sequence as set forth in any one of SEQ ID NOs: 72, 73, 74, or 75, and a complementarity determining region 3 (CDR3) comprising an amino acid sequence as set forth in any one of SEQ ID NOs: 77 or 78, wherein the VHH binds IL-7R.

4. The VHH of claim 1, wherein the VHH inhibits IL-7 binding to IL-7R.

5. The VHH of claim 1, wherein the VHH inhibits L-TSLP binding to IL-7R.

6. The VHH of claim 1, wherein the VHH comprises an amino acid sequence having 80% or greater sequence identity to SEQ ID NO: 8.

7. The VHH of claim 1, wherein the VHH comprises SEQ ID NO: 8.

8. An VHH that binds to IL-7R comprising SEQ ID NO: 8.

9. A method of treating an autoimmune and/or inflammatory disease comprising administering to an individual in need thereof the VHH of claim.

10. The method of claim 9, wherein the autoimmune and/or inflammatory disease comprises Crohn's disease or ulcerative colitis.

11. A method of treating an autoimmune and/or inflammatory disease comprising administering to an individual in need thereof the VHH of claim 2.

12. The method of claim 11, wherein the autoimmune and/or inflammatory disease comprises Crohn's disease or ulcerative colitis.

13. A method of treating an autoimmune and/or inflammatory disease comprising administering to an individual in need thereof the VHH of claim 3.

14. The method of claim 13, wherein the autoimmune and/or inflammatory disease comprises Crohn's disease or ulcerative colitis.

15. A method of treating an autoimmune and/or inflammatory disease comprising administering to an individual in need thereof the VHH of claim 8.

16. The method of claim 15, wherein the autoimmune and/or inflammatory disease comprises Crohn's disease or ulcerative colitis.

* * * * *

UNITED STATES PATENT AND TRADEMARK OFFICE
CERTIFICATE OF CORRECTION

PATENT NO. : 11,667,719 B2
APPLICATION NO. : 17/752710
DATED : June 6, 2023
INVENTOR(S) : Scott Crowe et al.

It is certified that error appears in the above-identified patent and that said Letters Patent is hereby corrected as shown below:

In the Claims

Column 156, Line 24:
In Claim 8, replace:
"An VHH"
With:
"A VHH".

Column 156, Lines 26-28:
In Claim 9, replace:
"A method of treating an autoimmune and/or inflammatory disease comprising administering to an individual in need thereof the VHH of claim."
With:
"A method of treating an autoimmune and/or inflammatory disease comprising administering to an individual in need thereof the VHH of claim 1.".

Signed and Sealed this
Twenty-third Day of July, 2024

Katherine Kelly Vidal
*Director of the United States Patent and Trademark Office*